US012762975B2

(12) United States Patent
Welch et al.

(10) Patent No.: US 12,762,975 B2
(45) Date of Patent: Oct. 13, 2026

(54) PHYSICAL-VIRTUAL PATIENT SYSTEM

(71) Applicant: UNIVERSITY OF CENTRAL FLORIDA RESEARCH FOUNDATION, INC., Orlando, FL (US)

(72) Inventors: Gregory F. Welch, Longwood, FL (US); Gerd Bruder, Orlando, FL (US); Salam Daher, Clifton, NJ (US); Jason Eric Hochreiter, Cocoa, FL (US); Mindi A. Anderson, Oviedo, FL (US); Laura Gonzalez, Orlando, FL (US); Desiree A. Diaz, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 79 days.

(21) Appl. No.: 18/738,601

(22) Filed: Jun. 10, 2024

(65) Prior Publication Data

US 2024/0331573 A1 Oct. 3, 2024

Related U.S. Application Data

(62) Division of application No. 16/786,342, filed on Feb. 10, 2020, now Pat. No. 12,008,917.

(51) Int. Cl.

*G09B 23/30* (2006.01)
*A61B 34/10* (2016.01)

(Continued)

(52) U.S. Cl.

CPC .............. *G09B 23/34* (2013.01); *A61B 34/10* (2016.02); *H04N 9/3141* (2013.01);

(Continued)

(58) Field of Classification Search

CPC ................................ G09B 23/28; G09B 23/30

See application file for complete search history.

(56) References Cited

U.S. PATENT DOCUMENTS

| | | | |
|---|---|---|---|
| 1,653,180 | A | 12/1927 | Jalbert |
| 2,158,906 | A | 5/1939 | Netter |

(Continued)

FOREIGN PATENT DOCUMENTS

| | | | |
|---|---|---|---|
| CN | 212750132 | U | 3/2021 |
| WO | 2014186853 | A1 | 11/2014 |

OTHER PUBLICATIONS

Aebersold, Michelle et al., "Virtual/Augmented Reality for Health Professions Education Symposium", INACSL Conference, Jun. 19-22, 2019, PP Presentation, 103 pages.

(Continued)

*Primary Examiner* — Kurt Fernstrom

(74) *Attorney, Agent, or Firm* — Timothy H. Van Dyke; Wolter Van Dyke; Davis, PLLC

(57) ABSTRACT

A patient simulation system for healthcare training is provided. The system includes one or more interchangeable shells comprising a physical anatomical model of at least a portion of a patient's body, the shell adapted to be illuminated from within the shell to provide one or more dynamic images viewable on the outer surface of the shells; wherein the system comprises one or more imaging devices enclosed within the shell and adapted to render the one or more dynamic images on an inner surface of the shell and viewable on the outer surface of the shells; one or more interface devices located about the patient shells to receive input and provide output; and one or more computing units in communication with the image units and interface devices, the computing units adapted to provide an interactive simulation (Continued)

for healthcare training. In other embodiments, the shell is adapted to be illuminated from outside the shell.

20 Claims, 30 Drawing Sheets

(51) Int. Cl.

| | |
|---|---|
| ***G09B 23/34*** | (2006.01) |
| ***H04N 9/31*** | (2006.01) |
| ***H04N 23/698*** | (2023.01) |
| *G09B 23/28* | (2006.01) |
| *G09B 23/32* | (2006.01) |

(52) U.S. Cl.

CPC ...... *H04N 23/698* (2023.01); *A61B 2034/107* (2016.02); *G09B 23/285* (2013.01); *G09B 23/303* (2013.01); *G09B 23/32* (2013.01)

(56) References Cited

U.S. PATENT DOCUMENTS

| | | | | |
|---|---|---|---|---|
| 3,053,144 | A | 9/1962 | Harries | |
| 4,076,398 | A | 2/1978 | Galbraith | |
| 4,104,625 | A | 8/1978 | Bristow | |
| 4,375,909 | A | 3/1983 | Bos | |
| 4,978,216 | A | 12/1990 | Liljegren | |
| 5,023,725 | A * | 6/1991 | Mccutchen | G06T 3/08 348/383 |
| 5,221,937 | A | 6/1993 | Machtig | |
| 5,325,473 | A | 6/1994 | Monroe | |
| 6,056,406 | A * | 5/2000 | Park | G03B 37/00 353/74 |
| 6,227,864 | B1 | 5/2001 | Egalandsdal | |
| 6,273,728 | B1 | 8/2001 | Van Meurs | |
| 6,467,908 | B1 | 10/2002 | Mines | |
| 6,527,555 | B1 * | 3/2003 | Storm | G09B 27/08 434/130 |
| 6,644,816 | B1 * | 11/2003 | Perra | G09F 19/18 349/5 |
| 7,229,176 | B2 * | 6/2007 | Onaga | G03B 21/26 353/94 |
| 7,434,943 | B2 * | 10/2008 | Kondo | G06F 1/1601 353/122 |
| 7,996,890 | B2 | 8/2011 | Sucher | |
| 8,113,660 | B1 | 2/2012 | Troyer | |
| 8,256,904 | B2 | 9/2012 | Reichow | |
| 8,328,368 | B2 | 12/2012 | Luciano | |
| 8,517,543 | B2 | 8/2013 | Reichow | |
| 8,936,366 | B2 | 1/2015 | Papaefstathiou | |
| 9,046,758 | B2 * | 6/2015 | Liu | H04N 13/393 |
| 9,300,901 | B2 | 3/2016 | Grundhofer | |
| 9,519,995 | B2 * | 12/2016 | Narukawa | G06T 17/20 |
| 9,679,500 | B2 * | 6/2017 | Welch | G03B 21/00 |
| 10,237,455 | B2 * | 3/2019 | Geerds | H04N 23/51 |
| 10,440,349 | B2 * | 10/2019 | Duggan | H04N 13/282 |
| 10,618,467 | B2 * | 4/2020 | Jeon | G06V 20/58 |
| 10,818,055 | B2 * | 10/2020 | Itoi | G06T 11/60 |
| 11,250,630 | B2 * | 2/2022 | Knipp | H04N 9/3194 |
| 11,871,114 | B2 * | 1/2024 | Cho | H04N 23/698 |
| 2007/0279183 | A1 | 12/2007 | Yang | |
| 2010/0007773 | A1 | 1/2010 | O'Connell | |
| 2010/0275719 | A1 | 11/2010 | Ortmaier | |
| 2012/0038739 | A1 | 2/2012 | Welch et al. | |
| 2012/0045742 | A1 | 2/2012 | Meglan | |
| 2012/0285978 | A1 | 11/2012 | Reichow | |
| 2012/0327201 | A1 | 12/2012 | Kappler | |
| 2014/0272871 | A1 | 9/2014 | Welch | |
| 2015/0037775 | A1 | 2/2015 | Ottensmeyer | |
| 2015/0086955 | A1 | 3/2015 | Poniatowski | |
| 2015/0325148 | A1 | 11/2015 | Kim | |
| 2015/0379901 | A1 | 12/2015 | Welch et al. | |
| 2016/0314712 | A1 | 10/2016 | Grubbs | |
| 2017/0011745 | A1 | 1/2017 | Navaratnam | |
| 2019/0340943 | A1 * | 11/2019 | Jimenez | G06F 3/04895 |
| 2022/0004019 | A1 * | 1/2022 | Lin | G02B 1/14 |

OTHER PUBLICATIONS

Benko, Hrvoje et al., "Sphere: multi-touch interactions on a spherical display", In Proceedings of the 21st annual ACM symposium on User interface software and technology (UIST '08), 2008, ACM, New York, NY, USA, pp. 77-86.
Chauh, Joon Hao et al., "Exploring Agent Physicality and Social Presence for Medical Team Training", Presence, 2013, vol. 22, No. 2, pp. 141-170.
Daher, Salam et al., "Matching vs. Non-Matching Visuals and Shape for Embodied Virtual Healthcare Agents", 2 pages.
Daher, Salam et al., "Optical See-Through vs. Spatial Augmented Reality Simulators for Medical Applications", 2 pages.
Daher, Salam et al., "Preliminary Assessment of Neurologic Symptomatology Using an Interactive Physical-Virtual Head with Touch.", IMSH, Jan. 2016, 1 page.
Daher, Salam et al., "Humanikins: Humanity Transfer to Physical Manikins", 2 pages.
Daher, Salam et al., "The Physical-Virtual Patient Simulator", Simulation in Healthcare, 2020, 7 pages.
Daher, Salam et al., "Physical-Virtual Agents for Healthcare Simulation", IVA, Nov. 2018, Sydney Australia, 8 pages.
Daher, Salam et al., "Physical-Virtual Patient Bed", Aug. 2017, 11 pages.
Daher, Salam, Patient Simulators: the Past, Present, and Future, Jan. 2019, 20 pages.
Daher, Salam et al., "Effects of Social Priming on Social Presence with Intelligent Virtual Agents", IVA 2017, LNAI 10498, pp. 87-100.
The Florida Nurse, Sep. 2017, vol. 65, No. 3, 20 pages.
Gonzalez, Laura et al., Vera Real: Stroke Assessment Using a Physical-Virtual Patient (PVP), 2019 INACSL Conference, 23 pages.
Gu, Jiseong et al., Poster Presentation, UIST Oct. 2011, 2 pages.
Han, Jefferson Y. et al., "Low-Cost Multi-Touch Sensing through Frustrated Total Internal Reflection", UIST, Oct. 2005, pp. 115-118.
Hochreiter, Jason et al., "Cognitive and Touch Performance Effects of Mismatched 3D Physical and Visual Perceptions", IEEE Virtual Reality, Mar. 2018, 8 pages.
Hochreiter, Jason et al., "Optical Touch Sensing on Non-Parametric Rear-Projection Surfaces", 2018 IEEE Conference on Virtual Reality and 3D User Interfaces, Mar. 2018, 2 pages.
Kim, Kangsoo et al., "Revisiting Trends in Augmented Reality Research: A Review of the 2nd Decade of ISMAR (2008-2017)", 16 pages.
Kotranza, Aaron et al., "Virgual Human + Tangible Interface= Mixed Reality Human an Initial Exploration with a Virtual Breast Exam Patient", 8 pages.
Lincoln, Peter et al., "Animatronic Shader Lamps Avatars", 10 pages.
Matsushita, HoloWall"Desigining a Finger, Hand, Body, and Object Sensitive Wall", UIST, 1997, Banff, Alberta, Canada, 2 pages.
Norouzi, Nahal et al., "A Systematic Survey of 15 Years of User Studies Published in the Intelligent Virtual Agents Conference", IVA, Nov. 2018, Sydney, NSW Australia, 6 pages.
Rekimoto, Jun, "SmartSkin: An Infrastructure for Freehand Manipulation on Interactive Surfaces", Letters CHI, 2002, vol. 4, No. 1, pp. 113-120.
Rivera-Gutierrez, Diego et al., "Shader Lamps Virtual Patients: the Physical Manifestation of Virtual Patients", 5 pages.
Roudaut, Anne et al., Touch Input on Curved Surfaces, CHI 2011, May 2011, Vancouver, BC, Canada, 10 pages.
Schubert, Ryan et al., "Mitigating Perceptual Error in Synthetic Animatronics Using Visual Feature Flow", Vision Sciences Society Annual Meeting Abstract, Aug. 2017, 2 pages.
Schubert, Ryan et al., "Adaptive Filtering of Physical-Virtual Artifacts for Synthetic Animatronics", ICAT-EGVE, 2018, 8 pages.

(56) References Cited

OTHER PUBLICATIONS

Villar, Nicolas et al., "Mouse 2.0: multi-touch Meets the Mouse", UIST, Oct. 2009, Victoria British Columbia, Canada, 10 pages.
Wang, Feng et al., "Detecting and Leveraging Finger Orientation for Interaction with Direct-Touch Surfaces", UIST, Oct. 2009, Victoria British Columbia, Canada, 10 pages.
Welch, Greg et al., "Interactive Rear-Projection Physical-Virtual Patient Simulators", 2 pages.
Welch, Gregory et al., "Physical Manifestations of Virtual Patients", Simulation in Healthcare, 1 page.
Wilson, Andrew D. "TouchLight: An Imaging Touch Screen and Display for Gesture-Based Interaction", ICMI, Oct. 2004, State College, Penssylvania, USA, 8 pages.
Bourke, Paul, "Spherical mirror: A new approach to hemispherical dome projection", 2005 ACM 1-59593-201-1/05/0010, pp. 281-284.
Bourke, Paul, "Spherical Mirror: A New Approach to Hemispherical Dome Projection", Proceedings of the 3rd International Conference on Computer Graphics and Interactive Techniques in Australasia and Southeast Asia 2005, Dunedin, New Zealand, Nov. 29-Dec. 2, 2005.
C. Cruz-Neira, D. J. Sandin, T. A. DeFanti, R. V. Kenyon, and J. C. Hart. The CAVE: audio visual experience automatic virtual environment. Commun. ACM, 35(6):64-72, Jun. 1992.
V. Nalwa. A true omnidirectional viewer. Technical report, Bell Laboratories, Holmdel, NJ 07733, Feb. 1996.
J. Underkoffler. A View From the Luminous Room. Personal Technologies, 1(2):49-59, Jun. 1997. Abstract only.

* cited by examiner

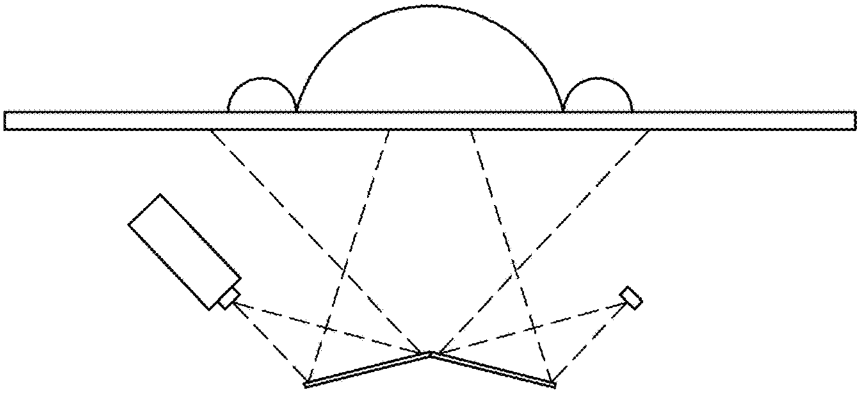
FIG. 8
FIG. 9
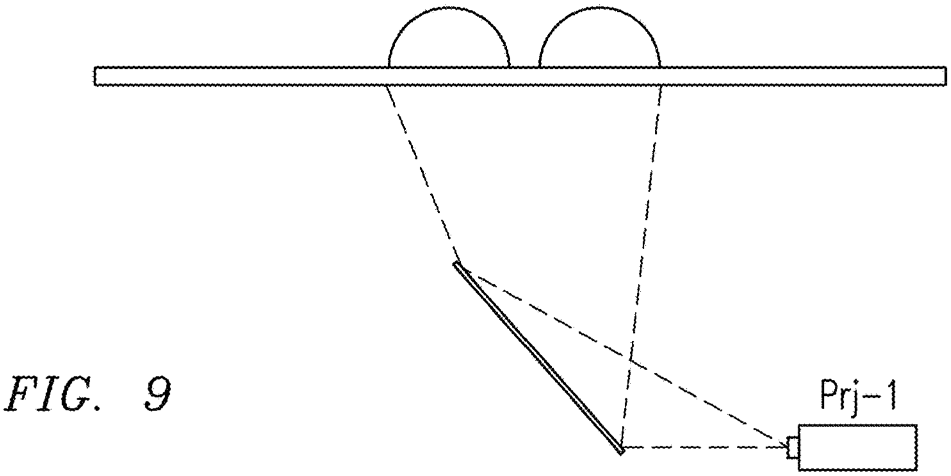
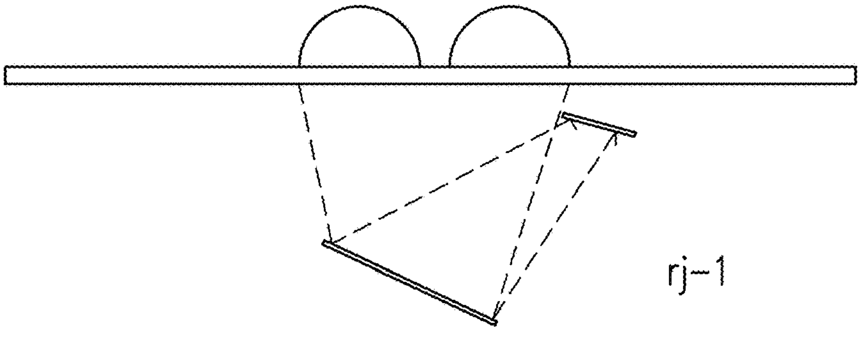
FIG. 10

PHYSICAL-VIRTUAL PATIENT SYSTEM

FIELD OF THE INVENTION

This invention relates to a patient simulator system for healthcare training, and more specifically, to a realistic physical-virtual patient simulator system for healthcare training.

BACKGROUND OF THE INVENTION

There are presently a number of patient simulator systems for training healthcare personnel, including fully screen-based simulated systems and mannequin systems, including robotic Human Patient Simulators (HPS). In the screen-based systems, a computer-based virtual patient is displayed on a screen. The visual appearance could include 2D computer graphics, 3D graphics, stereo, or head-tracked imagery. However, there is typically no physical interaction with anything resembling a real physical patient. The mannequin-based simulators are typically computer controlled/robotic and can be programmed for a range of responses that simulate a variety of healthcare symptoms and problems. They are able to simulate physical symptoms that can be checked such as heart rate, blood pressure, and simulated breathing. The available simulators range from relatively simple and inexpensive mannequins (a.k.a. "manikins") useful for basic "part task" training, such as that disclosed in U.S. Pat. No. 6,227,864. Other available patient simulator mannequins utilize complex computer-controlled systems to provide more realistic environments, as disclosed for example in U.S. Pat. No. 6,273,728. Unfortunately, the mannequin's visual appearance and certain behaviors are often static and unrealistic—there is typically no ability to change such things as the skin color, the skin temperature, the patient race or gender, nor the patient shape/size. Most patient simulators also have no way of sensing the touch (location and force) of the healthcare provider; hence the simulated patient is unable to react to physical contact, neither physiologically nor emotionally.

More realistic mannequins and figures are often used in amusement and theme parks to entertain guests. These devices can use, for example, a film image projected on the face to animate its expression. One technique, known as the front projection technique, involves projecting the film image directly onto the outer surface of the figure's face from a concealed source in front of the face. A second technique, shown in U.S. Pat. Nos. 5,221,937, and 6,467,908, and published Application No. US20120285978, for example, uses back projection that involves projecting the film image, usually by one or more reflectors, onto the back of the figure's face from a remote film source to animate the facial expression of the figure. However, these animated figures do not provide the full functionality and interactivity needed in a healthcare training situation.

Hence, there is a need for patient simulators for healthcare training that combine both physical and virtual realities in systems that are not only customizable to a large number of scenarios but also realistic to provide complete physiological simulation necessary for proper training.

The present invention is designed to address these needs.

SUMMARY OF THE INVENTION

Broadly speaking, the invention comprises an improved system, method, and computer-readable media for a patient simulator for healthcare training that combines physical and virtual realities, hereinafter referred to generally as a Physical-Virtual Patient (PVP) system.

The invention can be implemented in numerous ways, including as a system, a device/apparatus, a method, or a computer readable medium. Several example embodiments of the invention are discussed below.

As a system, an embodiment of the invention includes a translucent or transparent patient shell. Such shells would typically be created from a smooth rigid or semi-rigid material that allows for the formation of projected imagery on the surface, where the shell is also formed to approximate or in some way represent the shape of a real human (or other type of patient, e.g., an animal). The shell may have a fully or partially open back side to allow for illumination from behind, or might be completely closeable such that internal projection can be affected on all of the surfaces. The shell may be secured to a rigid frame or other assembly to allow the frame to be interchangeably mounted to a bed or other fixed system. Alternatively, the frame and associated components may be made to be held and moved independently of any bed or other fixed system. The shell is illuminated from below or inside by one or more image projectors adapted to render dynamic patient imagery onto the underneath or inside of the shell so that the image appears on the surface of the shell in a realistic manner. Various well-known optical components and configurations can be used to, for example, "fold," translate, scale, spread/compress, distort/un-distort the projected imagery. Flat and what can be called "omnidirectional" (e.g., cylindrical, spherical, hemispherical, and pyramidal mirror systems) are just some examples of components used to modify the path or shape of the projected imagery. Some of those same optical components or configurations might be simultaneously or independently used for optical sensing of touch, or other optical effects or needs, as well understood by a person of ordinary skill. A person of ordinary skill in the art would also understand that it is also possible to omit independent specialized optics, and to arrange two or more imaging devices (e.g., projectors or cameras) such that they achieve an "omnidirectional" effect, e.g., physical construction with lenses placed close to each other such that the frusta meet or overlap (typically a small amount). One or more computing units including memory and a processor unit communicate with the projectors and other interactive sensing and output devices to provide the interactive simulation. Interactive sensing and output devices include, but are not limited to, optical touch sensing devices, targeted temperature feedback devices, audio-based tactile devices for creating a sensation of pulse, human/object tracking, and spatial audio components with signal processing capabilities to both recognize real speech (input) and to create a sensation of audible vital signs (output). The system further includes interchangeable human shells and parts of human shells representing body parts capable of being secured to and used with the patient system without having to change out the expensive and sensitive optical, electrical, or other components that remain fixed in the frame/assembly of the patient system. This approach is beneficial for example when the frame/assembly of the patient system is incorporated into a bed, as the human shells could be removed or replaced without disturbing sensitive components mounted inside the bed (underneath the shells).

In a specific embodiment, a patient simulation system for healthcare training is provided, comprising: a shell of a physical anatomical model of at least a portion of a patient's body (e.g., human or animal), the shell adapted to be illuminated from behind or from within the shell to provide one or more dynamic images viewable on the outer surface of the shell; a bed system adapted to receive the shell via a mounting system, wherein the bed system—with or without a rigid frame/assembly, has one or more image units adapted to render the one or more dynamic images viewable on the outer surface of the shell; one or more interface devices located inside, underneath, or around the patient shell to receive input and provide output associated with the patient or people/devices near the patient; and one or more computing units in communication with the image units and interface devices, the computing units adapted to provide an interactive simulation for healthcare training.

Further refinements include wherein the shell is at least in part translucent or transparent for illumination from behind by the one or more image units; wherein the shell includes one or more interchangeable human-shaped shells and interchangeable parts of patient-shaped shells (e.g., human or animal) representing body parts, adapted to be secured via the mounting system to the rigid frame, assembly, or bed system; wherein an underneath surface of the shell consists of a rear projection "screen" material (e.g., a coating such as on a projection screen) to permit better visualization of the one or more dynamic images viewable on the outer surface of the shell; wherein the shell has one or more openings on a back side thereof to allow for unobstructed rendering of the one or more dynamic images by the one or more image units; wherein the shell is an upper longitudinal slice of a prone human figure having a partially or fully open back to allow for unobstructed rendering of the one or more dynamic images by the one or more image units; and wherein the shell has one or more additional separations or flexible portions to allow for movement of the shell on an articulating PVP system.

Aspects of the invention further include wherein the one or more image units render dynamic patient imagery from behind or inside the shell onto an underneath of the shell so that the one or more images viewable on the outer surface of the shell simulate viewable conditions including one or more of skin color, medical condition, and facial expressions.

The one or more interface devices may include one or more sensory devices, interactive devices, human/object tracking devices, and output devices, such as one or more optical touch sensing devices, targeted temperature feedback devices, audio-based tactile sense of pulse devices, and spatial audio components with signal processing to simulate vital signs.

In certain embodiments, the system includes an upper assembly adapted to resemble a standard hospital bed or gurney, and a lower frame or assembly adapted to house the one or more image units, interface devices, and computing units. In other embodiments, the system includes an internal assembly, surrounded by complete enclosed human-shaped shell, where the internal assembly is adapted to support the one or more image units, interface devices, and computing units, for example. The one or more image units include one or more projectors and one or more mirrors coupled to a support in the frame or assembly and arranged with proper alignment, registration, and focus, so that a projected image will properly project onto the underneath surface of the shell and show through on the outer surface of the shell. The plurality of projectors may span the portion of the system that will be occupied by the shell so that each of the plurality of projectors are positioned to cover a different portion of the shell.

As a method, an embodiment comprises implementing one or more patient simulations using the PVP system for healthcare training. The method of the present invention may be implemented in conjunction with a computing device and as part of a computer program product with a non-transitory computer-readable medium having code thereon. The computing device may include at least one processor, a memory coupled to the processor, and a program residing in the memory which implements the methods of the present invention.

Aspects of the invention include a method for implementing one or more patient simulations using a patient simulation system having a shell comprising a physical anatomical model of at least a portion of a patient's body and a frame or assembly (e.g., bed or full human) adapted to receive the shell, the method including: illuminating the shell from behind to provide one or more dynamic images viewable on the outer surface of the shell via one or more image units adapted to render the one or more dynamic images viewable on the outer surface of the shell; interfacing with one or more interface devices located about or within or near the patient shell to receive input and provide output as part of the simulation; and providing an interactive simulation for healthcare training via one or more computing units in wired or wireless communication with the image units and interface devices. In some embodiments, the frame or assembly is omitted and the method includes the illuminating step.

The advantages of the invention are numerous, including cost and visual realism. In terms of cost, because of the interchangeability of the shells with the expensive components remaining fixed in a rigid frame/assembly associated with the system, the system would be flexible in terms of patient's physical characteristics, while remaining relatively inexpensive compared to an HPS. In addition, the system provides very realistic dynamic visual appearances, including "human" patients that can turn and look at you, appear pale or flush, appear to cry, smile, etc., to provide a more realistic experience. The system may be used for a range of civilian and military healthcare training, including physicians, nurses (including, for example, nurse practitioners), healthcare technicians, emergency healthcare technicians, paramedics, administrative staff, and even hospital volunteers. The conventional HPS does not change visual appearance in any way. It cannot change skin color per certain healthcare conditions, cannot simulate wounds graphically under computer control, cannot appear to change gender or race, cannot exhibit live facial expressions (e.g., smile, frown, or look frightened), and cannot move or give the appearance of moving body parts such as heads or limbs.

Accordingly, aspects of the present invention provide an advantage for simulation of a human patient in a way that supports changing appearance (e.g., race and various healthcare symptoms), alterable size (e.g., child or adult), some physiological signals, along with apparent or actual motion of body parts.

Other aspects and advantages of the invention will become apparent from the following detailed description taken in conjunction with the accompanying drawings, illustrating, by way of example, the principles of the invention.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 8 shows a third design example for Torso Projection having a Single Mirror Crossfire Configuration.

FIG. 9 shows a first design example for Legs Projection having Single Mirror Path Folding.

FIG. 10 shows a second design example for Legs Projection having Dual Mirror Path Folding.

DETAILED DESCRIPTION OF THE INVENTION

Figure 1:
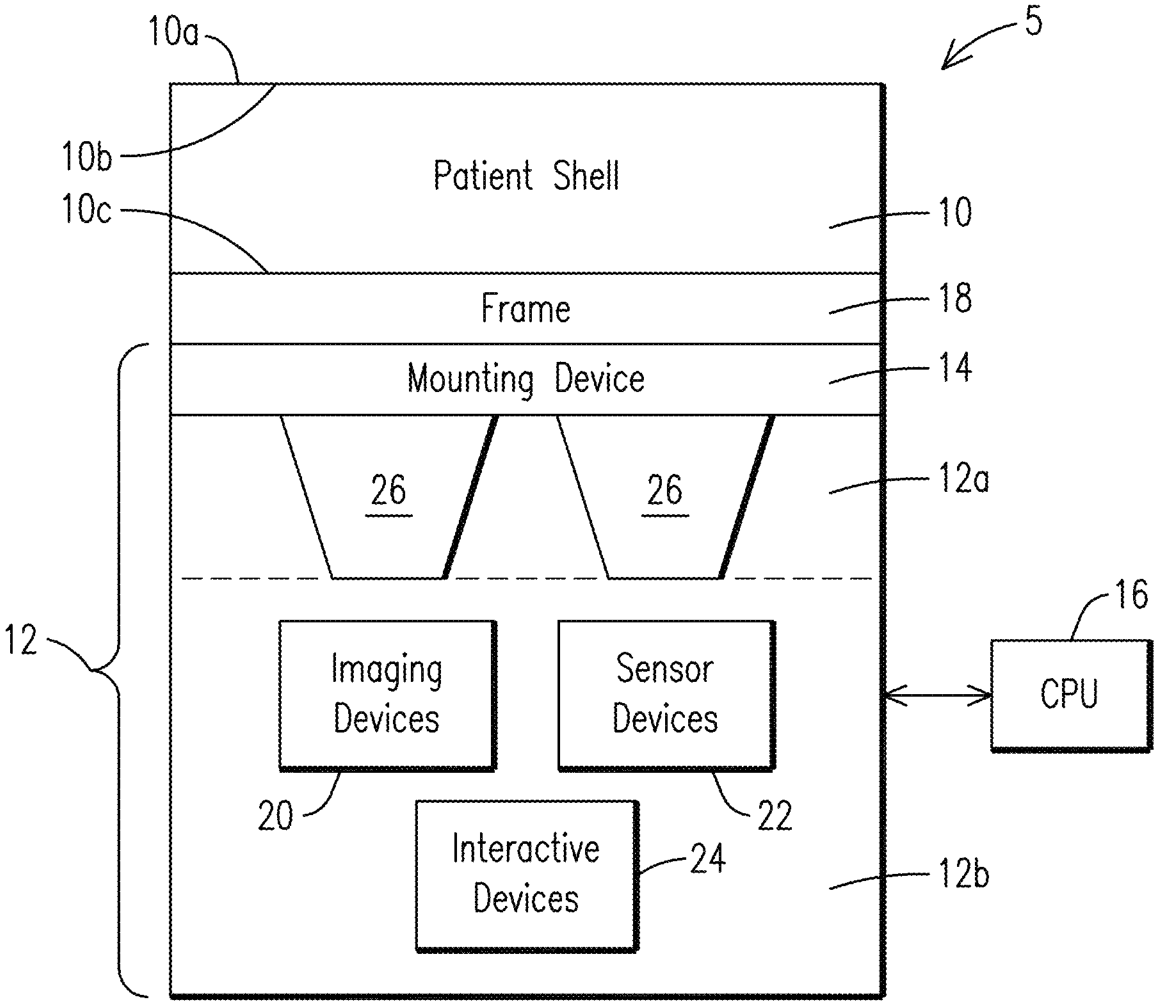
FIG. 1 is a block diagram of an embodiment of the invention.

Referring now to the drawings, the preferred embodiment of the present invention will be described.

Notwithstanding that the numerical ranges and parameters setting forth the broad scope are embodiment-specific approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term ""about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4. Finally, a person of ordinary skill would understand that different embodiments will correspond to different numerical analyses with different numerical results, all subject to at least the caveats listed above.

FIG. 1 shows a block diagram of a patient simulator 5 for healthcare training hereinafter referred to as the Physical-Virtual Patient (PVP) system. The PVP system 5 includes a translucent or transparent patient shell 10 secured to a housing 12. The shell 10 is illuminated from below by one or more image projectors 20 in the housing 12 adapted to render dynamic patient imagery onto the underneath of the shell 10 so that the image appears on the surface of the shell 10 in a realistic manner. One or more computing units 16 including memory and a processor unit communicate with the projectors 20 and other sensory devices 22 and interactive devices 24 to provide the interactive simulation. In some embodiments, the computing unit 16 includes a module 17 that includes one or more instructions for the computing unit 16 to perform one or more operations discussed herein and/or one or more steps of a method 1500 depicted in the flowchart of FIG. 29. In some embodiments, the computing unit 16 is a computer system 1600 as discussed below with respect to FIG. 30 and/or a chip set 1700 as discussed below with respect to FIG. 31 and/or a mobile device 1800 as discussed below with respect to FIG. 32.

Sensory devices 22 and interactive devices 24 include, but are not limited to, optical touch sensing devices, targeted temperature feedback devices, audio-based tactile sense of pulse devices, and spatial audio components with signal processing device to simulate vital signs. The PVP system 5 further includes interchangeable human shells 10 and parts of human shells representing body parts capable of being secured via a mounting device 14 to the housing 12 without having to change out the expensive and sensitive components (20, 22, 24) that remain fixed in the housing 12.

Figure 25:
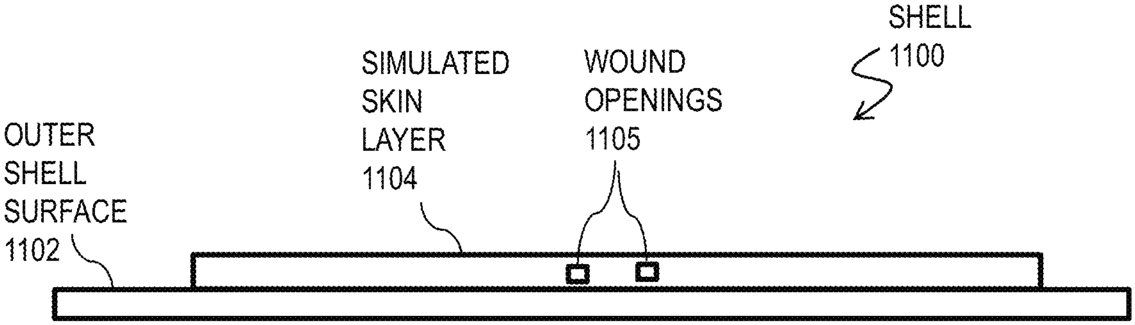
FIG. 25 is an image that illustrates an example of a simulated layer of skin over the outer surface of the shell in FIG. 2, according to an embodiment.

The patient simulator 5 combines physical (e.g., patient shell) and virtual (e.g., imaging, sensory) realities. In some embodiments, the PVP system 5 the housing 12 may take the form of a real (or realistic) hospital bed, modified to include a prone human-shaped mannequin in the form of a shell 10, such as a vacuform (vacuum formed material) patient "shell" that is illuminated from below by one or more image projectors 20 (e.g. digital projectors) that render dynamic patient imagery onto the rear (underneath) of the shell 10. The effect is that nearby humans (e.g., nurses in training, students) can see a dynamic physical-virtual "patient" lying in bed, where the imaging system provides for the patient to exhibit lifelike facial expressions (while talking, etc.), lifelike skin color (e.g., to convey race or symptoms), realistic wounds, etc. FIG. 25 is an image that illustrates an example of a simulated layer of skin 1104 over the outer surface 1102 of the shell 1100 in FIG. 2, according to one embodiment. In some embodiments, the simulated layer of skin 1104 and the outer surface 1102 of the shell collectively display the dynamic images from the image units 20. This might be the case, for example, in embodiments that use projected imagery, and both the outer surface and the simulated skin are semi-translucent/opaque. In another embodiment the outer surface of the shell might emitting light (imagery) such as from a deformable display technology, and the simulated skin would be transparent. In other embodiments, the simulated layer of skin 1104 displays the dynamic images from the image units 20 separate from the outer surface 1102 of the shell 1100 (e.g. the skin layer 1104 is placed in a region corresponding to an opening in the shell 1100, or the shell 1100 is totally transparent (not semi-transparent). In still other embodiments, the sensor devices 22 (e.g. touch sensing devices, temperature sensing devices, etc.) are operatively coupled to the simulated layer of skin 1104. In still other embodiments, the simulated layer of skin 1104 has one or more of a temperature, texture and softness corresponding to a respective temperature, texture and softness of real skin (e.g. the simulated layer of skin 1104 is constantly heated and temperature is held fixed at human body temperature, etc.). In further embodiments, the simulated layer of skin 1104 defines one or more openings 1105 that simulate a wound. In an example embodiment, during the interactive simulated for medical training, the user of the system 5 is instructed to repair the wound opening 1105 (e.g. using a suture, etc.). In some embodiments, the computing unit 16 transmits a signal to an interactive device 24 (e.g. audio device) to audibly instruct the user, such as a guide, to repair the wound opening 1105 with certain medical equipment that is provided and/or may provide verbal instructions and/or feedback.

Projectors 20, when mounted as a rear projection system, allow for materials such as blankets, clothing-like coverings, and various healthcare components or devices to be placed over the physical-virtual patient in the bed 12 and to not interfere with the projected images. The same would be true for the use of emissive deformable displays.

Figure 27:
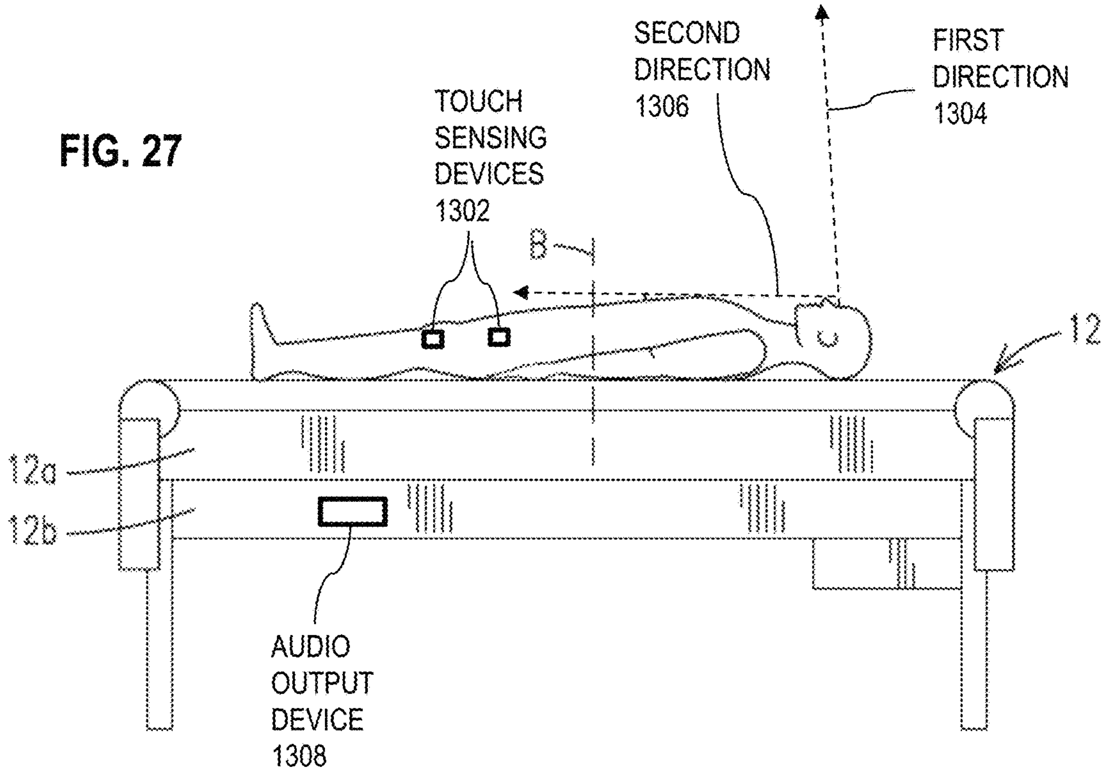
FIG. 27 is an image that illustrates an example of a plurality of touch sensing devices embedded in the outer surface of the shell in FIG. 2, according to an embodiment.

To add to the interactivity and enhance healthcare training simulation, further embodiments of the PVP system also include touch sensing (e.g., from hands or medical devices) via a sensor system 22 for the "skin" (e.g., via various optical approaches), and skin temperature control (e.g., via temperature-controlled air streams directed to the underside of the shell) via interactive devices 24. Further interactive devices 24, such as audio or other active sources (e.g., via speakers under the bed, pointing up toward the shell) may be used to add audible or tactile signals such as a heartbeat or pulse. FIG. 27 is an image that illustrates an example of a plurality of touch sensing devices 1302 embedded in the outer surface of the shell 10 in FIG. 2, according to an embodiment. In an embodiment, the interface devices include the sensory devices 22 such as the touch sensing devices 1302. In one embodiment, the touch sensing devices 1302 generate one or more first signals upon receiving input from an environment of the system (e.g. when a user touches the outer surface of the shell 10 adjacent to the touch sensing device 1302). In this embodiment, the computing unit 16 receives the one or more first signals from the touch sensing devices 1302 and subsequently transmits one or more second signals to the image units 20, where the second signal is based on the received one or more first signals. In one example embodiment, the image units 20 are configured to vary the one or more dynamic images viewable on the shell 10 based on the one or more second signals received from the computing unit 16. In some embodiments, the image units 20 are configured to vary the one or more dynamic images on the shell 10 such that a part of the patient's body (e.g. a virtual part based on a dynamic image) moves from a first position to a second position. In an example embodiment, the part of the patient's body is the eyes and the image units 20 cause the eyes to move from a first direction 1304 (FIG. 27) to a second direction 1306 (e.g. in a direction of the location where the touch occurred). In yet another example embodiment, the part of the patient's body is the mouth and the image units 20 cause the mouth to move from a first position (e.g. closed, open) to a second position (e.g. open, closed), etc. In yet another example embodiment, the part of the patient's body is a physical part of the body (e.g. not a virtual part based on a dynamic image from the image unit 20) and the control unit 16 is configured to transmit the one or more second signal to an interactive device 24 (e.g. motor) to cause the part of the patient's body to move from a first position to a second position (e.g. a tongue in a mouth from a first position inside the mouth to a second position outside the mouth; a joint of the body to move from a first position to a second position, such as an arm to move from a first position to a second position or a leg to kick outward when a user taps the knee, etc.). In such an embodiment the projectors or displays in general could be adapted to move with the moving body part, or the system could track the changing relationship between the projector/display and the moving body part and render the imagery in a "pre-distorted" way that appears correct.

In still other embodiments, an audio output device 1308 (FIG. 27) such as an audio speaker is configured to receive the second signal from the computing unit 16 and is configured to transmit an audio sound (e.g. pain shriek, laugh, cry, etc.) based on the received second signal from the computing unit 16. In an example embodiment, the transmitted audio sound is based on the second signal from the computing unit 16 and the second signal is based on a value of a measured parameter (e.g. pressure) and/or a location of a measured parameter (e.g. weighted more for sensitive areas). In some embodiments, a user can input a desired trainee skill level (e.g. using an input device 1612 in FIG. 30, such as a keyboard, mouse, etc.) where the desired skill level is based on a number of the patient's body parts that are responsive to the touching sensing devices 1302. In still other embodiments, touch sensing devices 1302 can be provided to detect other visual responses (e.g. capillary refill, tug lips, tug eyelids, pupil dilations), and non-touch sensing devices can be used to similarly detect physiology responses (e.g. change of heart rate, pulse, breathing).

Figure 5:
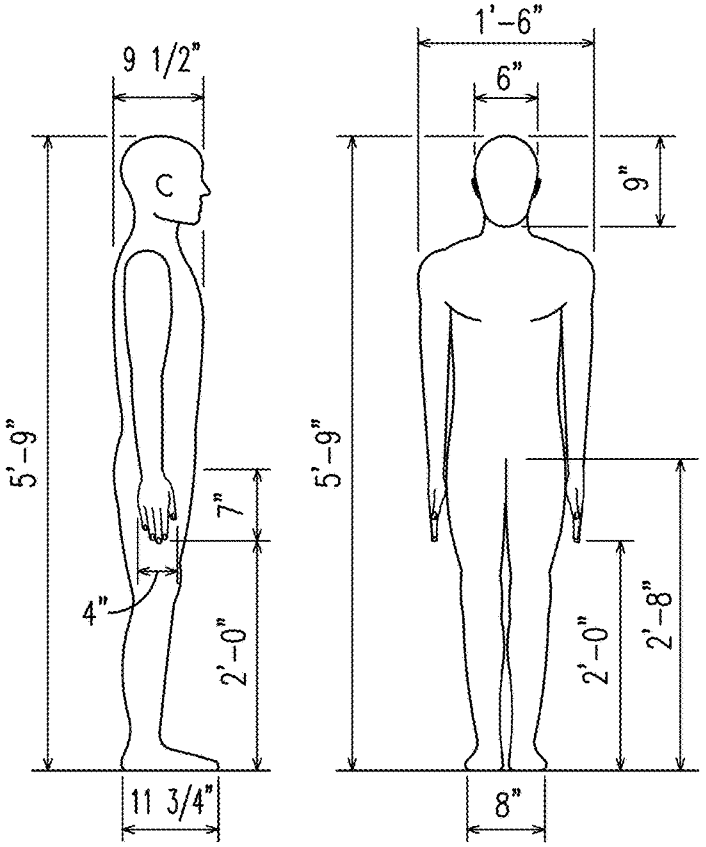
FIG. 5 shows an illustration of example torso dimensions.
Figure 18A:
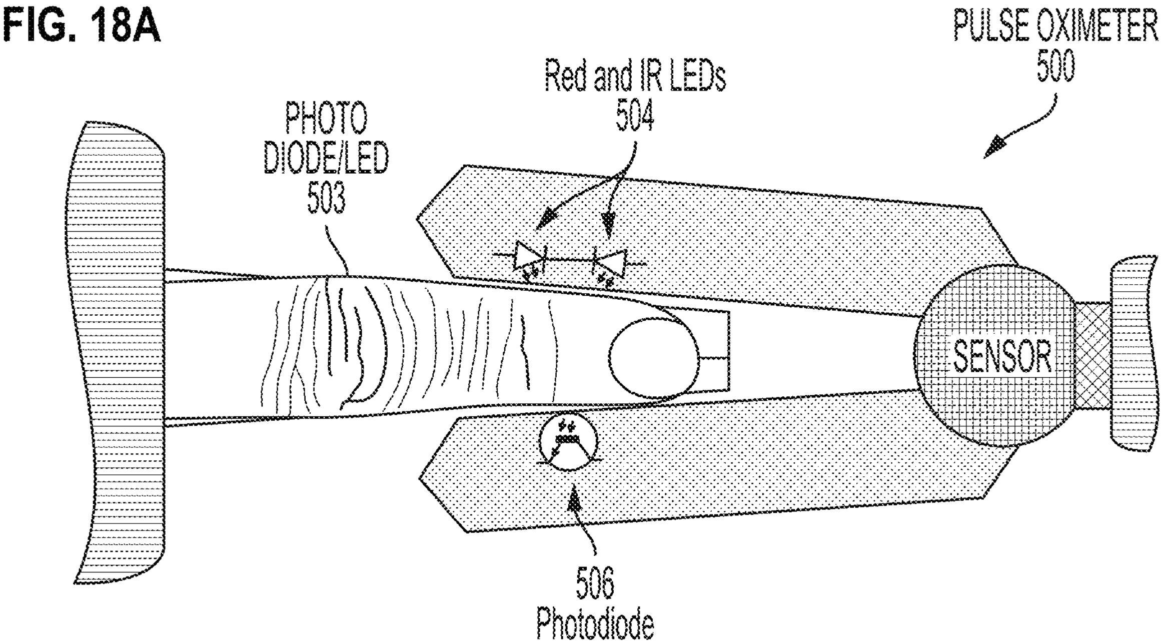
FIG. 18A is an image that illustrates an example of an actively-illuminated finger of the shell of FIG. 5 positioned in an interactive device to measure a physiological parameter, according to an embodiment.

The interactive devices 24, such as targeted temperature feedback devices, audio-based tactile sense of pulse devices, and spatial audio components with signal processing device may be provided to simulate vital signs. In some embodiments, the shell defines a plurality of slots which separate a plurality of joints in the patient's body (e.g. slots that define a plurality of fingers in FIG. 5 and similarly define a plurality of toes). In one embodiment, the interactive devices 24 include a sensor (e.g. pulse oximeter, blood pressure cuff, etc.) to measure a value of a physiological parameter (e.g. pulse, oxygen level, heart rate, blood pressure, etc.) and the joints are configured to operatively connect with the sensor. In some embodiments, the joints do not transmit a signal that is measurable by the sensor. In other embodiments, the joints do transmit a signal that is measurable by the sensor. FIG. 18A is an image that illustrates an example of a finger 502 of the shell of FIG. 5 positioned in a sensor (e.g. pulse oximeter 500) to measure a physiological parameter, according to an embodiment. As appreciated by one skilled in the art, the pulse oximeter 500 includes a pair of red and IR LEDs 504 that transmit radiation and a photodiode 506 to detect an intensity of the radiation transmitted through a finger to measure the pulse and oxygen level in the blood. In this embodiment, the finger 502 includes an internal photodiode/LED 503 which collectively detect and transmit radiation to the photodiode 506 with the appropriate intensity and direction so that the pulse oximeter 500 registers a pulse and oxygen level of a desired value (e.g. normal range). In some embodiments, the internal photodiode/LED 503 transmit radiation so that the pulse oximeter 500 registers an abnormal pulse and/or oxygen level, for purposes of medical training. In other embodiments, other parts of the shell (e.g. arm) can be provided with similar internal components to transmit a signal to a measuring sensor (e.g. blood pressure cuff) to register values of physiological parameters that are within or not within normal range, for example. For example, U.S. Pat. No. 3,868,844A to Klein teaches a dynamic arterial blood pressure simulator comprising a pressure chamber, a flexible member in the wall of the chamber, a cam having a shape proportionate to at least one hypothetical arterial blood pressure cycle, and means for driving the cam to displace the flexible member producing a variable pressure within the chamber. In an example embodiment, the internal components to stimulate the blood pressure signal include a pneumatic air-based system or a servo based mechanical deformation.

Figure 18B:
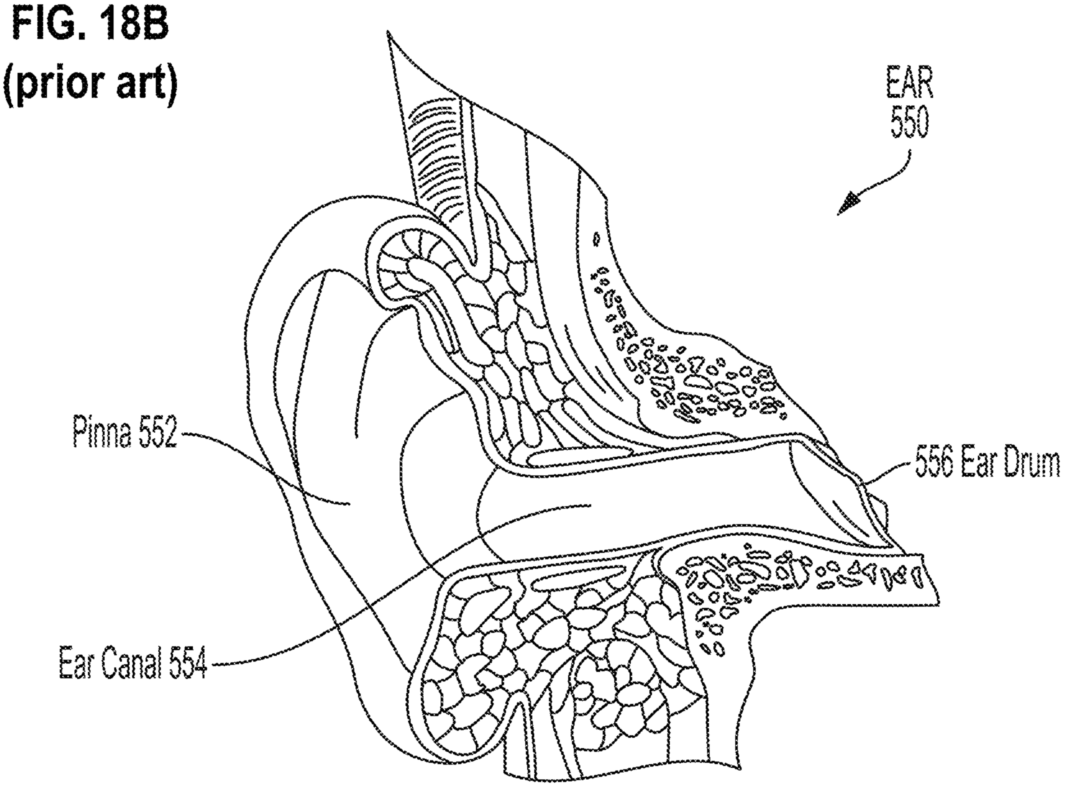
FIG. 18B (prior art)
FIG. 18B is an image that illustrates an example of a conventional orifice in an ear of a human patient.

In another embodiment, the shell 10 defines at least one orifice that receives a virtual overlay representing a natural membrane (e.g. ear drum) and/or attach equipment within the at least one orifice in the interactive simulation. FIG. 18B is an image that illustrates an example of a conventional orifice (car canal 554) in an ear 550 of a human patient. In some embodiments, the shell 10 includes an orifice corresponding to the ear canal 554 and a virtual overlay corresponding to the natural ear drum 556. In an example embodiment, the material used to simulate the ear drum includes transparent opaque material such as Ear Model Soft Silicone provided by Soundlink® (Model number 8541766604). In another example embodiment, U.S. Publication Number 20180315348A1 discloses material that can be used to simulate the ear drum and is incorporated by reference herein. In another example embodiment, the size of the material used to simulate the ear drum would mimic that of a human eardrum which would vary on the size of the patient. In another example embodiment, the size of the material used to simulate the human eardrum would be used in simulated training for assessment and diagnosis of disease processes related to the ear (e.g. otitis media, etc.)

The targeted temperature feedback over the surface of the body provides numerous advantages. The temperature-controlled forced air in select areas of a rear-projection surface, e.g., a human body, uniquely conveys temperature information to users. From a healthcare standpoint (as an example) skin temperature, when combined with visual appearance and behavior, can be an important symptom of shock or fever. The audio-based tactile sense of pulse uniquely uses multiple surface-mounted acoustic emitters (speakers or similar transducers) and associated signal processing to provide a tactile sense of movement at a "phantom" location (a location other than the emitters). This method may be used to simulate the feeling of a pulse in the wrist or neck, for example, without the need for transducers mounted at the exact point of the tactile sense. The separately-mounted spatial audio components and signal processing are uniquely used to provide a sense of a sound emanating from "within" a rear-projection surface, when sensed on the surface. This feature may be used, for example, to simulate a heartbeat and breathing emanating from within the body, heard through a stethoscope placed on the surface of the body (the rear-projection human form/shell). The technique may be used to simulate anomalies such as labored breathing, pneumonia, or heart anomalies (e.g., a valve prolapse).

Figure 28A:
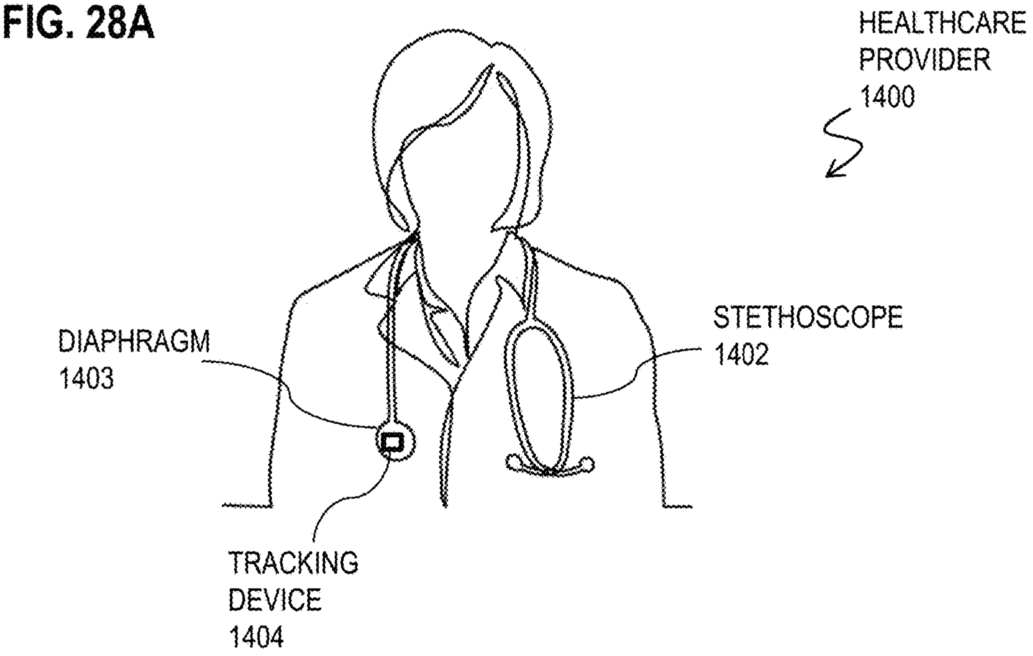
FIG. 28A is an image that illustrates an example of a healthcare provider with a stethoscope and a tracking device mounted to the stethoscope, according to an embodiment.
Figure 28B:
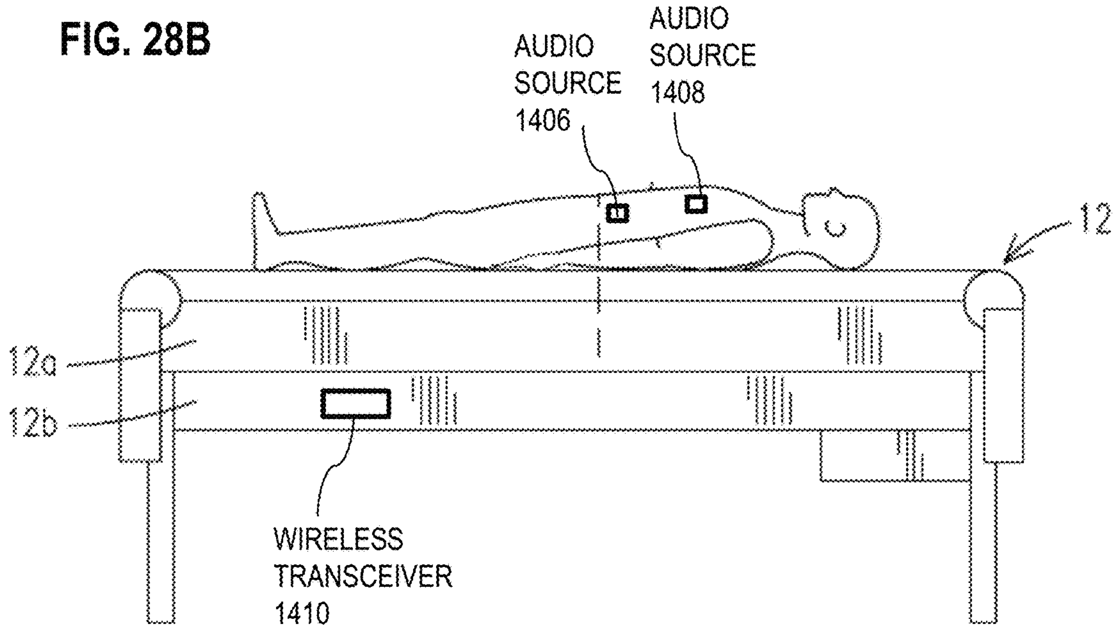
FIG. 28B is an image that illustrates an example of the bed system of FIG. 3 with a wireless transceiver communicatively coupled to the tracking device of FIG. 28A and audio sources in the shell, according to an embodiment.

FIG. 28A is an image that illustrates an example of a healthcare provider 1400 with a stethoscope 1402 and a tracking device 1404 mounted to the stethoscope, according to an embodiment. FIG. 28B is an image that illustrates an example of the bed system 12 of FIG. 3 with a wireless transceiver 1410 communicatively coupled to the tracking device 1404 of FIG. 28A and audio sources 1406, 1408 in the shell, according to an embodiment. In these embodiments, the interactive devices 24 of the system 5 include the tracking device 1404 and/or the wireless transceiver 1410 and/or the audio sources 1406, 1408. In an embodiment, the wireless transceiver 1410 is communicatively coupled to the tracking device 1404 to receive a first signal indicating a location of the stethoscope (e.g. diaphragm 1404) and further communicatively coupled to the one or more audio sources 1406, 1408 to transmit a second signal to a respective audio source 1406, 1408 to cause the respective audio source to transmit an audio signal. In an example embodiment, the audio signal is configured to be detected by the medical equipment (e.g. stethoscope 1402) and indicate a normal or abnormal condition in the patient's body. In an example embodiment, the audio source 1406 positioned at the first location (e.g. abdomen) is configured to transmit an audio signal when the stethoscope 1404 is positioned at the first location (e.g. placed on the abdomen) and/or the audio source 108 positioned at the second location (e.g. chest) is configured to transmit an audio signal when the stethoscope is positioned at the second location (e.g. placed on the chest). In still other embodiments, multiple audio sources may be positioned in the same area (e.g. multiple audio sources for multiple regions of the chest or abdomen, etc.). In still other embodiments the audio signal transmitted by the audio source 1406 is different than the audio source 1408 (e.g. configured to simulate audio sounds of abdomen (bowel, stomach) and chest, respectively, detected by the stethoscope). Although the stethoscope is discussed in this embodiment, in other embodiments other medical equipment may be used (e.g. pulse oximeter, blood pressure cuff, etc.) and non-audio signals may be transmitted to non-audio sources (e.g. IR sources, haptic sources, etc.) so that the medical equipment detect the signal from the source as within or not within normal range (e.g. depending on the training parameters).

Figure 17:
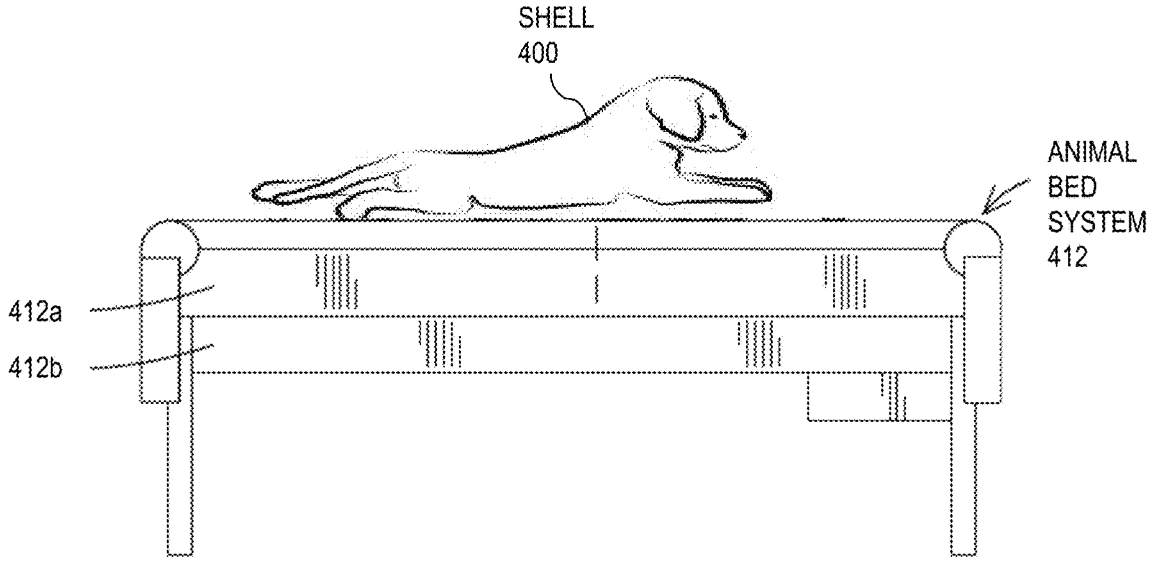
FIG. 17 is an image that illustrates an example of a shell of a non-human patient, according to an embodiment.

The shell 10 may be comprised of variations of shapes of humans, or non-human shapes, to accommodate "synthetic animatronics"—the use of computer graphics to convey the appearance of multiple and/or changing postures such as head (e.g., turning the head), or limbs (e.g., rotating the hand/arm). Because the image projectors 20 are located in the bed system 12 underneath the shell 10, a variety of shells 10 may be provided to allow for a wide range of patient simulators 5 without the increased cost and complexity of having imaging projectors 20 and electronics (e.g., sensor system 22, interactive devices 24, CPU 16) in each simulator. To that end, a variety of such patient shells 10 may be substituted/exchanged on the bed system 12, to allow, for example, different sized humans (e.g., thin or heavy, adult or child) or missing limbs (e.g., from an accident or amputation). This substitution may be accomplished, for example, by mounting via a suitable mounting device 14 the patient shells 10 in uniformly sized rigid frames that can be locked into place in the bed 12. Other suitable mounting devices 14 are also contemplated herein, such as brackets, fasteners, coupling members that allow for securely mounting and interchanging the patient shells 10. The rear-projection human form uniquely employs interchangeable human bodies and body parts. This feature will accommodate different genders, ages, and healthcare conditions. Examples include a child (small body), an obese person, and an amputee. Among other advantages, this approach offers a lightweight and simple (no attached electronics) approach to rapidly changing the simulated physical-virtual patient. The human shell forms themselves can be relatively inexpensive and robust. The expensive and sensitive components remain fixed under the bed system. FIG. 17 is an image that illustrates an example of a shell 400 of a non-human patient (e.g. dog) used with the bed system of FIG. 3, according to an embodiment. In some embodiments, the shell 400 comprises the physical anatomical model of a portion of a non-human patient's body (e.g. body of an animal), the shell adapted to be illuminated to provide one or more dynamic images on the outer surface of the shell. In an example embodiment, the non-human patient is an animal and the computing unit 16 is adapted to provide the interactive simulation for veterinary training (e.g. transmits one or more signals to the image units 20 to project dynamic images corresponding to the anatomy of the animals, where the dynamic images are sized so to project over an area corresponding to the size of the animal's body, etc.).

Other combinations/variations of imaging systems and techniques, used in lieu of or in addition to the imaging system 20 include the use of Shader Lamps-front (top) projection onto a static mannequin, the use of flexible displays (e.g., OLED), and the like, especially in retrofit situations. For example, front/top projection onto a robotic Human Patient Simulator (HPS) would add to the complete physiological simulation afforded by typical HPS units. Other retrofit techniques may be used to support synthetic animatronics, skin temperature changes, or touch sensing. FIG. 22 is an image that illustrates an example of the bed system of FIG. 3 with a front projection device 902 (projecting downward) and a head mounted display 906 worn by a user 904 to view the dynamic images, according to an embodiment. In an embodiment, the image units 20 include at least one front projection device 902 that is mounted above the shell 10 and is configured to render the one or more dynamic images viewable on the shell from above downward onto the shell. In another embodiment, the head mounted display 906 is communicatively coupled to the one or more computing units 16 and/or the image units 20 and/or the interface devices so that the head mounted display 906 is configured to display one or more of the shell 10 and the one or more dynamic images viewable on the shell. In an embodiment, the head mounted display 906 is an augmented reality (AR) headset which projects one or more virtual dynamic images on the real outer surface of the shell 10 in a frame of reference viewable by the user 904 through the head mounted display 906. In an example embodiment, the AR headset 906 projects some of the dynamic images (e.g. organs 803 in FIG. 21A) onto the outer surface of the shell 10 and the image units 20 in the lower assembly 12*a* project other dynamic images (e.g. venous system 802 in FIG. 21A) onto the outer surface of the shell 10. In an example embodiment, if occlusion between physical and virtual body parts or devices is the dominant factor, images would be preferred to come from the image units 20 in the lower assembly 12*a* since it preserves natural line of sight. In another example embodiment, the AR headset 906 is used for anything requiring virtual 3D imagery that could be "detached" from the patient's body, e.g., blood on the patient/wound imaged with the image units 20, but for blood dripping on the floor, images from the AR headset 906. In another example embodiment, front projection from the front projection device 902 can have superior image quality in some cases. On the flip side, front projection makes touch sensing more difficult. In an embodiment, the front projector is used to project different appearances onto opaque parts of the patient simulator (like painted wounds), otherwise the underneath projector is used. In still other embodiments, the one or more dynamic images are displayed by the head mounted display 906 based on a display characteristic assigned to a part of the patient's body. In an example embodiment, the display characteristic indicates that the one or more interface devices (e.g. sensory devices 22) provide output from the part of the patient's body. In another example embodiment, the display characteristic indicates whether the part of the patient's body is a real part viewable in real space or a virtual part only viewable in the frame of reference viewable by the user through the head mounted display 906.

In another embodiment, the AR headset 906 is configured to project the one or more virtual dynamic images of the virtual part such that the virtual part is shifted within the frame of reference to align with the shell 10 comprising the physical anatomical model of the portion of the patient's body. In this embodiment, the module 17 of the computing unit 16 features one or more instructions so that the virtual images are shifted within the frame of reference of the headset 906 so to align with the shell 10. In an example embodiment, optical marker tracking (e.g. c3aresys) is one example of such a method.

Figure 22:
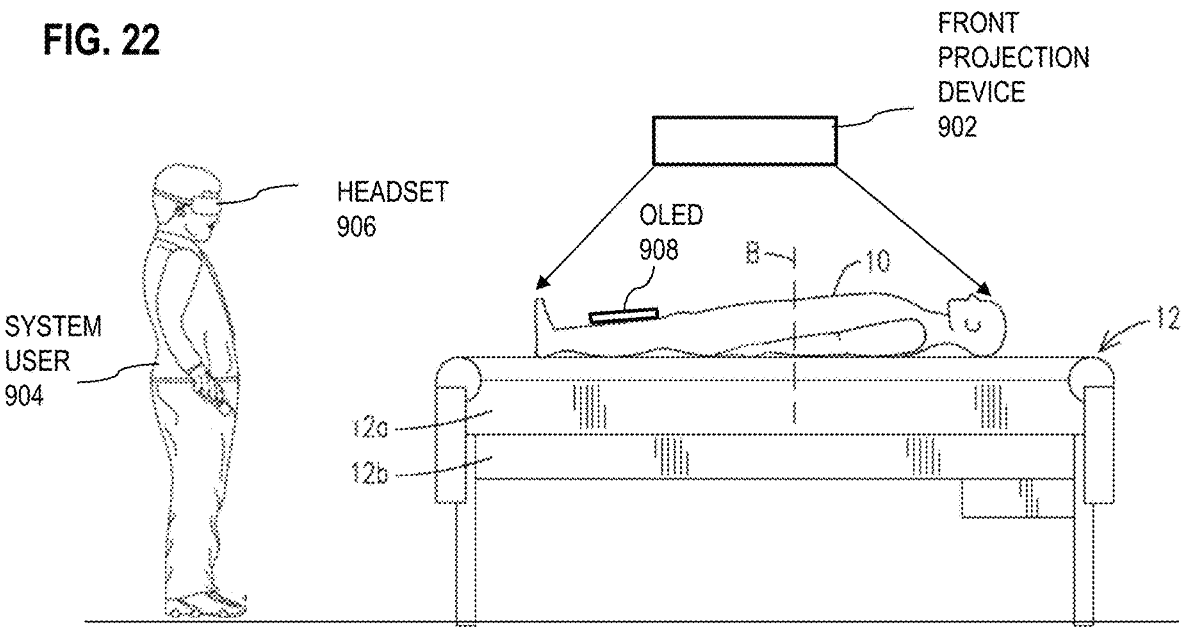
FIG. 22 is an image that illustrates an example of the system of FIG. 3 with a front projection device and a head mounted display worn by a user to view the dynamic images, according to an embodiment.
Figure 23:
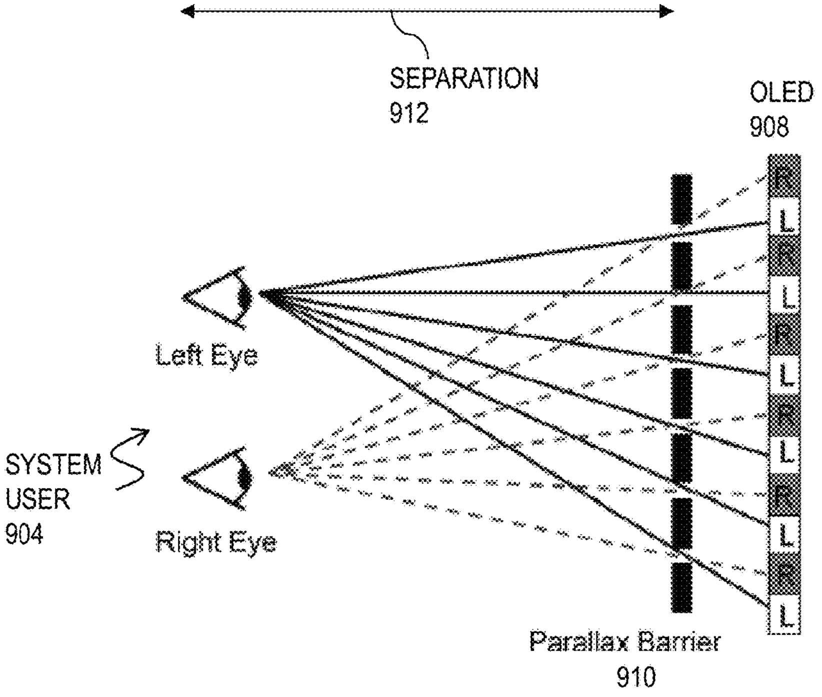
FIG. 23 is an image that illustrates an example of a ray diagram from an optical source to left and right eyes of a user through a parallax barrier to provide an autostereoscopic display, according to an embodiment.

Additionally, in an embodiment, FIG. 22 depicts a flexible display (OLED 908) positioned on the outer surface of the shell 10, wrapped around corresponding to the shape of the shell (body part). The emissive display would provide an alternate means to achieve imagery on the surface of the shell. Additionally, a flexible display could also be embedded into the surface of the shell, again formed in a manner such that it corresponds to the shape of the shell (body part). Furthermore, autostereoscopic mechanisms could provide the effect of stereo imagery seen by nearby viewers. FIG. 23 is an image that illustrates an example of a ray diagram from an optical source (e.g. OLED 908) to left and right eyes of a user 904 through a parallax barrier 910 to provide such an autostereoscopic display (ASD), according to an embodiment. In an embodiment, the user 904 is positioned at a fixed separation 912 from the parallax barrier 910 and thus in an example embodiment, the parallax barrier 910 provides the ASD for a number of pre-computed fixed spots (e.g. with fixed separation 912) next to the bed system 12. In an example embodiment, stereoscopy is employed (e.g., shuttering, anaglyphic) with or without head tracking. As would be understood by a person of ordinary skill, these and other stereo vision approaches would allow a user, wearing the appropriate glasses, to see virtual imagery appearing above or below the outer surface 1102 of the shell. In a further example embodiment, the outer surface of the shell 10 is actuated to match the simulated 3D movement (e.g. movement/deformation). In an example embodiment, there is various advantages and disadvantages for using the OLED or autostereoscopic as opposed to the augmented AR. Specifically, using the OLED requires no glasses, provides mono imagery, permits multiple users, has no occlusions, provides a physical object to touch but as disadvantages adds additional expense and increases the complexity of the shell. Similarly, the autostereoscopic provides advantages of not requiring glasses, providing stereo imagery, but includes disadvantages of limited eye movement and limited multiple users.

In an example embodiment, the shell 10 is made to serve as a rear projection screen in the form of a 3D figure of a human. The shell 10 may be molded from a translucent moldable material, such as plastic. In accordance with an embodiment, shell 10 comprises vacuformable material. A number of suitable vacuformable materials may be chosen such as acrylic, butyrate, and PETG (glycol-modified polyethylene terephthalate) which is a copolyester that may be a clear amorphous thermoplastic. The underneath surface 10*b* of the shell 10 may be coated with a rear projection screen material to permit better visualization of the image through to the top surface 10*a* projected by imaging system 20, and/or better optical sensing of touch through to the top surface 10*a* via the sensor system 22.

One or more openings may be provided on the back 10*c* of the shell 10 to allow for better projection of images by the imaging system 20 in the bed system 12 onto the underneath surface 10*b*. Alternatively, part, most, or the entire back side 10*c* of the shell 10 may be removed, such that the shell 10 comprises an upper longitudinal slice (e.g., approximately ½) of a prone human figure having a partially or fully open back 10*c*. The edge of the open back 10*c* of the shell 10 may be secured to a frame 18 or other rigid support device, so that the frame 18 can then be easily, securely, and interchangeably mounted to a corresponding mounting device 14 of the bed system 12.

Figure 2:
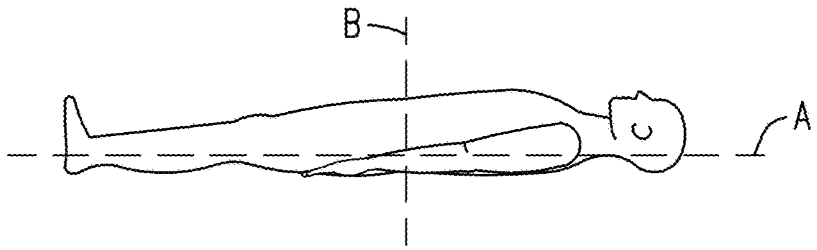
FIG. 2 is an illustration of a shell of an embodiment of the invention.

For example, a human shaped vacuform "shell" 10 can be obtained from a provider who produces special effects for theme parks, museums, trade shows and special events (e.g., People VisionFX of Roselle, NJ). In order to better provide for imaging and interactivity, the vacuform "shell" 10 may be sliced from head to toe longitudinally (line A of FIG. 2) opening the back side 10*c* to allow projection of the images through the opening, as shown in FIG. 2. It may also be separated at the waist (line B of FIG. 2) to allow for movement (e.g., bending at the waist) or other separations may be provided for movement of other body parts. The shell 10 with the cut-away back side 10*c* may then be mounted on a frame 18 or similar device that can be secured into place on the bed system 12. Proper mounting and placement of the shell 10 with respect to the bed system 12 and imaging system 20 comprise proper alignment, registration, and focus of the projected image onto the underneath surface 10*b* of the shell 10. Alignment and registration marks may be provided on the shell or as part of the frame 18 and/or mounting system 14.

The projectors 20 (e.g., digital projectors) that render dynamic patient imagery onto the underneath 10*b* of the shell 10 are designed and properly placed to project through the open back 10*c* of the shell 10. The projectors 20 may be placed in respective/corresponding openings 26 in the upper 12*a* and lower 12*b* bed mattress support areas. The sliced shell 10 may be mounted rigidly to a rectangular or similarly shaped frame 18 that that will mate with (attach to) a corresponding mounting device (e.g., frame) 14 on the bed system 12. The frame 14 may include a rigid "fill" material (e.g., plastic) that extends from the frame 14 to the shell 10.

Figure 19A:
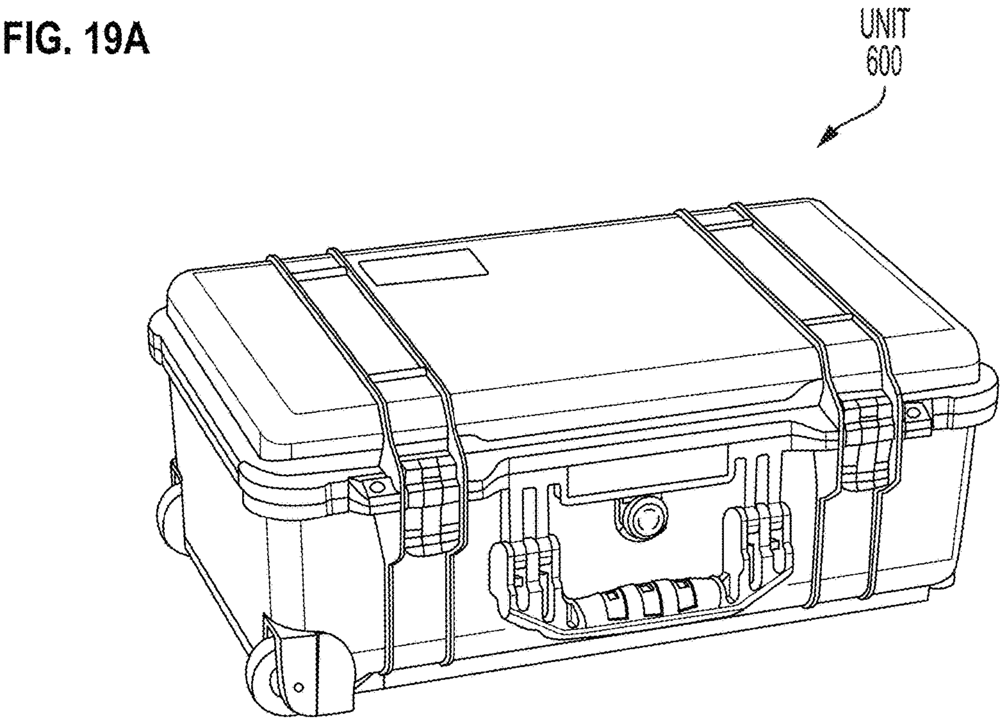
FIG. 19A is an image that illustrates an example of a mobile compact unit that houses the system of FIG. 3, according to an embodiment.
Figure 19B:
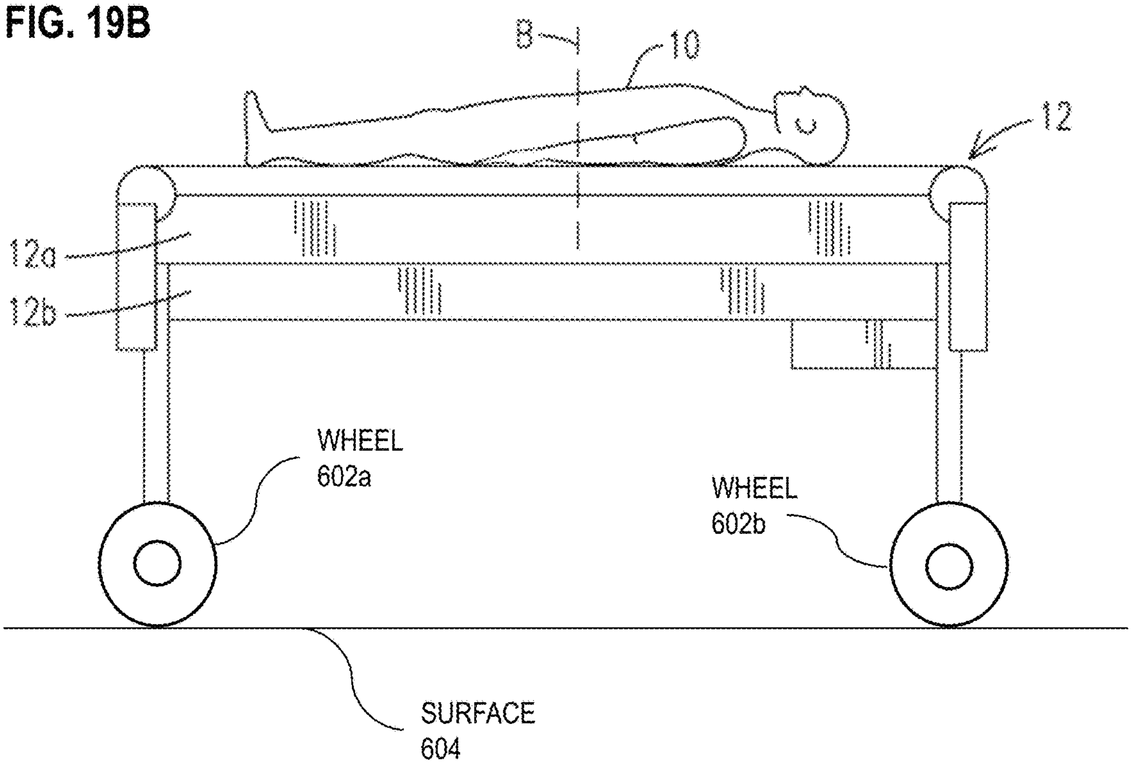
FIG. 19B is an example that illustrates an example of a mobile bed system assembled from the mobile compact unit of FIG. 19A, according to an embodiment.

In an example embodiment (see FIG. 3), the bed system 12 includes an upper assembly 12*a* and a lower assembly 12*b*. The upper assembly 12*a* may resemble a standard hospital bed or gurney. The lower assembly houses the electronics (e.g., imaging system 20, sensor system 22, and interactive devices 24). It may be specifically manufactured or retrofitted from a standard hospital bed (e.g., a POCKET NURSE® Full Electric Hospital Bed, of Monaca, PA). In certain embodiments, the hospital bed can be modified to allow only one point of articulation at/across the "waist" or knee, for example, with all other articulation restricted mechanically. Height adjustment may be maintained/allowed. When retrofitting, the mattress support area in the upper assembly 12*a* is cut/modified to provide one or more openings 26 through which the imaging system 20 can project imagery from below onto the underside 10*b* of the shell 10. Opening(s) 26 are placed and sized to properly project the imagery from the imaging system 20 through the mounting device 14 onto the underneath 10*b* of the shell 10. The opening(s) 26 cut in support area may be placed and sized to mate with the frame 18 of the shell 10 using a corresponding frame or similar mount 14. FIG. 19A is an image that illustrates an example of a mobile compact unit 600 that houses the bed system of FIG. 3, according to an embodiment. FIG. 19B is an example that illustrates an example of a mobile bed system 5 assembled from the mobile compact unit 600 of FIG. 19A, according to an embodiment. In an embodiment, the system 5 is configured to be converted from a mobile compact unit 600 to a bed system 5 positioned on wheels 602*a*, 602*b* that are configured to move over a surface 604 (e.g. floor of a hospital or medical unit or training area to perform the medical training). In another embodiment, the unit 600 encloses the shell 10 and the image system 20 and interface devices 20, 22, 24 positioned below the shell 10 in the bed system 5. In still other embodiments, the mobile unit 600 can be converted not only into the bed system 5 but into a room with a plurality of interior surfaces that are free-standing or linked together for support, and together represent walls that define the room that holds the bed system 5. These walls can serve as projection surfaces to allow the rendering of realistic environmental artifacts, different scene locations, a caregiver/parent, etc. surrounding the bed systems 5. Thereby, making a portable CAVE-like structure. (See [4] C. Cruz-Neira, D. J. Sandin, T. A. DeFanti, R. V. Kenyon, and J. C. Hart. The CAVE: audio visual experience automatic virtual environment. Commun. ACM, 35 (6): 64-72, June 1992, which is incorporated by reference herein.) In this embodiment, the system further comprises a plurality of interior surfaces defining an enclosure (e.g. room or portable) to position the bed system 5. The plurality of interior surfaces and the bed system 5 are enclosed within the mobile compact unit 600. In this embodiment, the mobile compact unit 600 is configured to be converted into the enclosure and the bed system positioned within the unit 600. A person of ordinary skill would understand that the same mobile compact unit 600 could be used to contain a PVP that is not in a bed, is an animal, etc.

Figure 20:
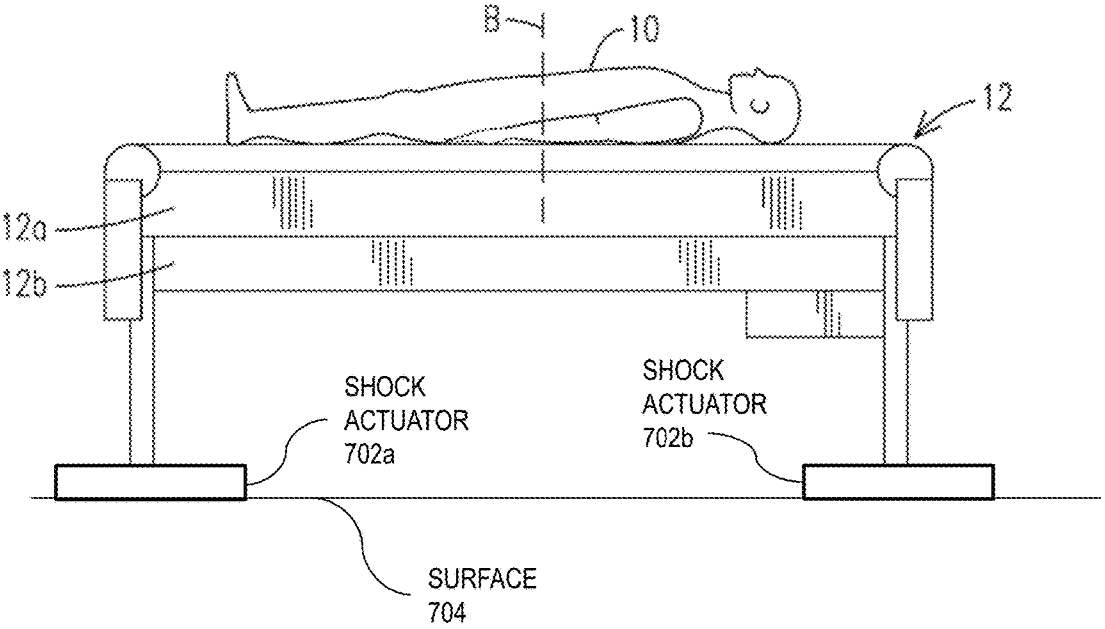
FIG. 20 is an image that illustrates an example of a bed system with a plurality of shock actuators to mount the bed system to a surface, according to an embodiment.

The lower assembly 12*b* is designed to support and house the electronics (e.g., imaging system 20, sensor system 22, interactive devices 24, CPU 16). In an embodiment, a platform such as a strong horizontal "shelf" or other mounting structure may be rigidly affixed to the upper and lower bed portions, mounted to the underside of the bed. The chosen support arrangement may allow for lateral, horizontal and vertical adjustments of the electronics. For flexibility and customization, the platform may be in the form of an "optical breadboard" (metal "pegboard") such as those manufactured by Thorlabs Inc. of Newton, New Jersey, that will permit repositioning of electronics, projectors, cameras, mirrors, etc. Rigid, passive, or active vibration damping may also be provided. FIG. 20 is an image that illustrates an example of a bed system with a plurality of shock actuators 702*a*, 702*b* made from rubber or other materials with elastic effect to mount the bed system 5 to a surface 704, according to an embodiment. In an embodiment, the system 5 is mounted to a surface (e.g. interior surface of an airplane) by a shock absorber 702*a*, 702*b* configured to absorb at least a portion of an induced force from the surface in a direction of the system (e.g. turbulence during the flight for in-flight nurse training). In yet another embodiment, the system 5 is mounted to a surface by a shock inducer 702*a*, 702*b* configured to induce a force in a direction from the surface to the system 5 to simulate an induced force from a moving surface (e.g. to simulate turbulence experience in an airplane, etc.). This advantageously permits the medical training to incorporate realistic scenarios such as air travel conditions (e.g. medical transport training). In an example embodiment, the shocker actuator 702*a*, 702*b* includes any shock inducer appreciated by one of ordinary skill in the art such as a monotube gas shock absorber. The design may accommodate folded optics arrangement with projectors and cameras below so they can be mounted horizontally on the optical breadboard, and the imagery can be reflected to the underside of the vacuform shell 10, as well as omnidirectional cameras and projectors.

Alternatively, the design may include "sleds" (mounting units) for projectors, cameras, and mirrors so that they can be moved around on the optical breadboard, and clamped down when in place. Sleds for projectors may provide a mechanism to mount wide angle adapters for projectors (such as wide-angle conversion lens that fit in front of the projector's standard lens allowing a projection image that is 50% larger than the projector's standard lens at the same distance (e.g., the SSC065 Mini ScreenStar Wide Angle Converter (0.65x) by Navitar, Inc. Rochester, New York). Adjustability of the optical sleds (mirrors, cameras, projectors) may include one or more of the following: translate in 2D on the optical breadboard, rotate about an axis coming out of the breadboard perpendicular, tilt up and down out of the plane of the breadboard. sleds/mounts may be used for mirrors.

The imaging system 20 provides the virtual effects for a more realistic experience. A wide variety of projectors may be used to obtain these effects. The imaging may be aligned, registered, stabilized, and controlled using image processing software (e.g. module 17 in computing unit 16) in a controller or CPU 16 in communication with the imaging system 20. Computer generated graphics may be used to create one or more images for projection. A media controller (separate from or part of CPU 16) may be operable to control media supplied to the imaging system 20 via communication means (e.g., wired/wireless) and therefore, projection of a particular image/image stream. Media may be retrieved from a plurality of stored and/or dynamically generated media, suitable for the particular training exercise.

The imaging system 20 comprises one or more projectors coupled to a support platform (via breadboard) in the lower assembly 12*b*. The platform provides a rigid support such that once the shell 10 and projector(s) of the imaging system 20 are arranged with proper alignment, registration, and focus, and the optical components are sufficiently calibrated (e.g., the geometric and photometric parameters), the projected image will properly project onto the underneath surface 10*b* of the shell 10 and show through on to the top surface 10*a* of the shell 10. An example projector includes the AAXA M2 micro projector from AAXA Technologies of Tustin, CA, which can be used with an adapter (e.g., a Vivitar adapter) for WFOV (Wide Field Of View). LED projectors may be chosen for reliability, consistency, short throw, non-critical resolution, lighting, etc. Since the human shell 10 can have different images projected on different parts thereof, a plurality of projectors may be used. The projectors can be arranged to have projector overlap on the "shell" surface (which may be minimal).

Figure 13:
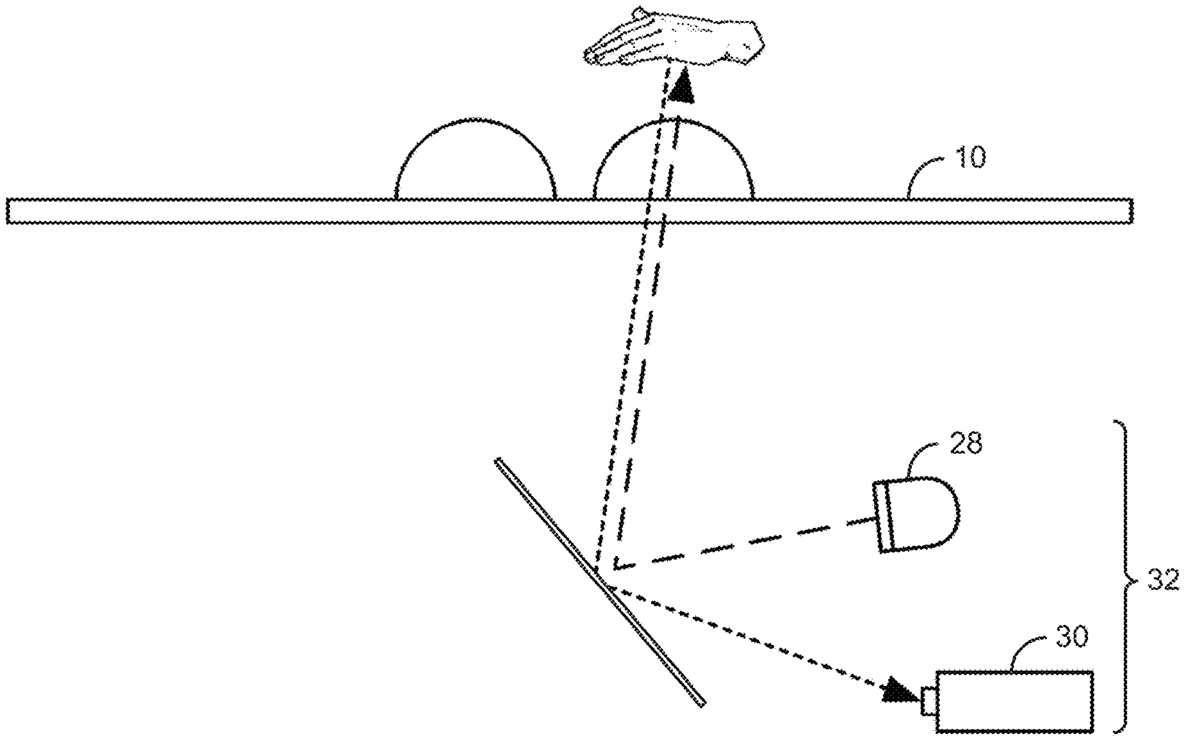
FIG. 13 shows a design example for an optical touch sensing device employing a mirror to achieve a folded optical path.
Figure 14:
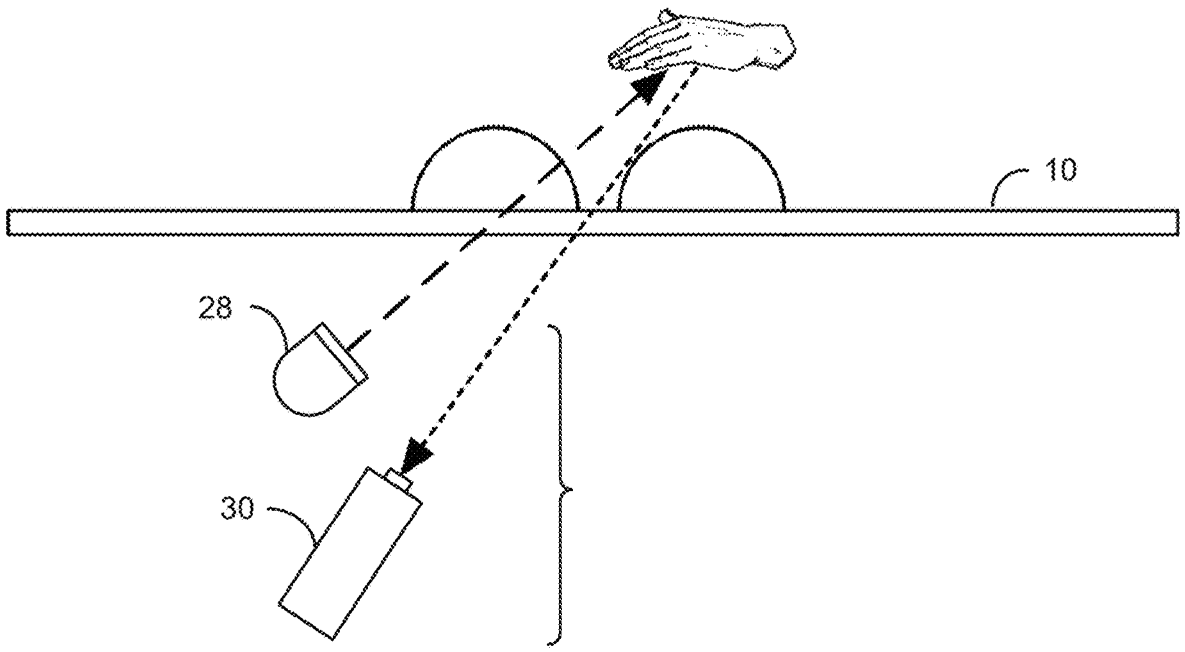
FIG. 14 shows a design example for an optical touch sensing device with a direct (not folded) optical path.

For the purpose of touch sensing for the simulator, the sensor system 22 may provide for camera-based optical touch technology, such as optical touch sensing device 32, to detect the presence of a touching object, including traditional infrared, waveguide infrared, vision-based, LCD In-cell Optical, or the like (see FIGS. 13 and 14). In an embodiment, the interface devices includes one or more sensors 32 to detect a presence of an object (e.g. hand) within a proximate distance of the outer surface of the shell 10. In one embodiment, the sensor 32 is an optical touch sensing device configured to detect one of a hand of a user within the proximate distance of the outer surface of the shell and a gesture of the hand of the user. In an example embodiment, the sensor 32 is configured to detect hovering and associated mid-air gestures (e.g., 3D pinch, tap, grasp). In yet another example embodiment, the sensor 32 is a pressure sensor that is configured to detect and/or measure a level of pressure during touch (e.g., using optical IR touch sensing or Velostat-like materials). The term "camera" 30 is used in optical touch to designate an assembly that typically includes a housing, image sensor, cable, lens, and IR filter. Depending on the system architecture, a camera 30 may also include an IR light source (for retro-reflective systems) and an image processor. Advantages of certain features include this body-specific optical touch sensing over the entire human body form and its unusual topology. Specifically, the system employs novel multiple overlapping infrared light sources and image forming cameras to cover and decode touch over a non-parametric surface, with shape discontinuities and occlusions, such as occurs with a touch surface in the shape of the human body.

Figure 34A:
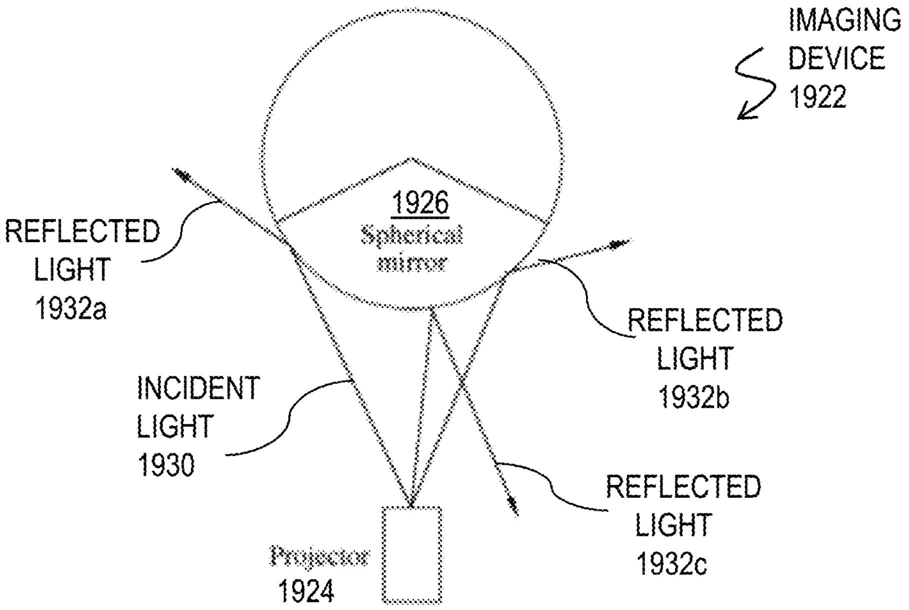
FIG. 34A is a schematic diagram that illustrates an example of a top view of an imaging device of FIG. 33B within the shell, according to an embodiment.
Figure 34B:
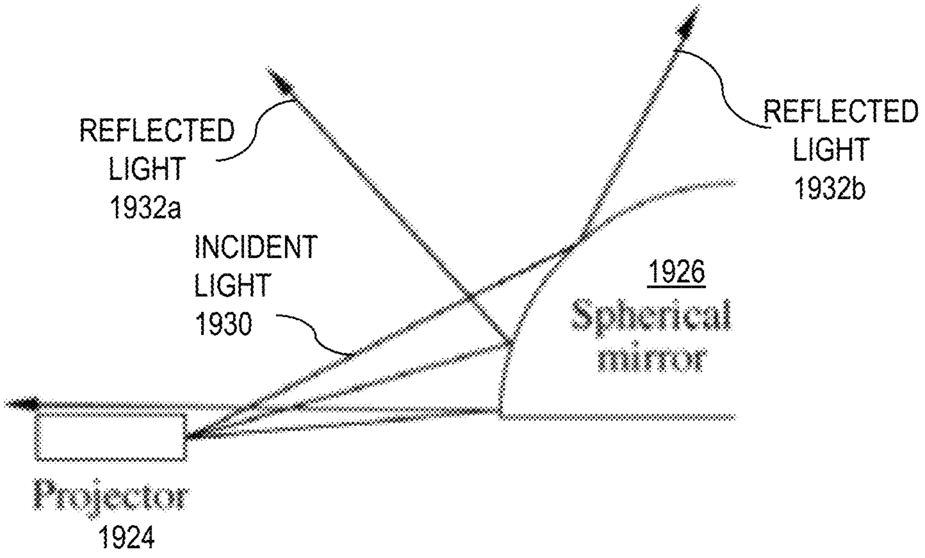
FIG. 34B is a schematic diagram that illustrates an example of a side view of an imaging device of FIG. 33B within the shell, according to an embodiment.
Figure 34C:
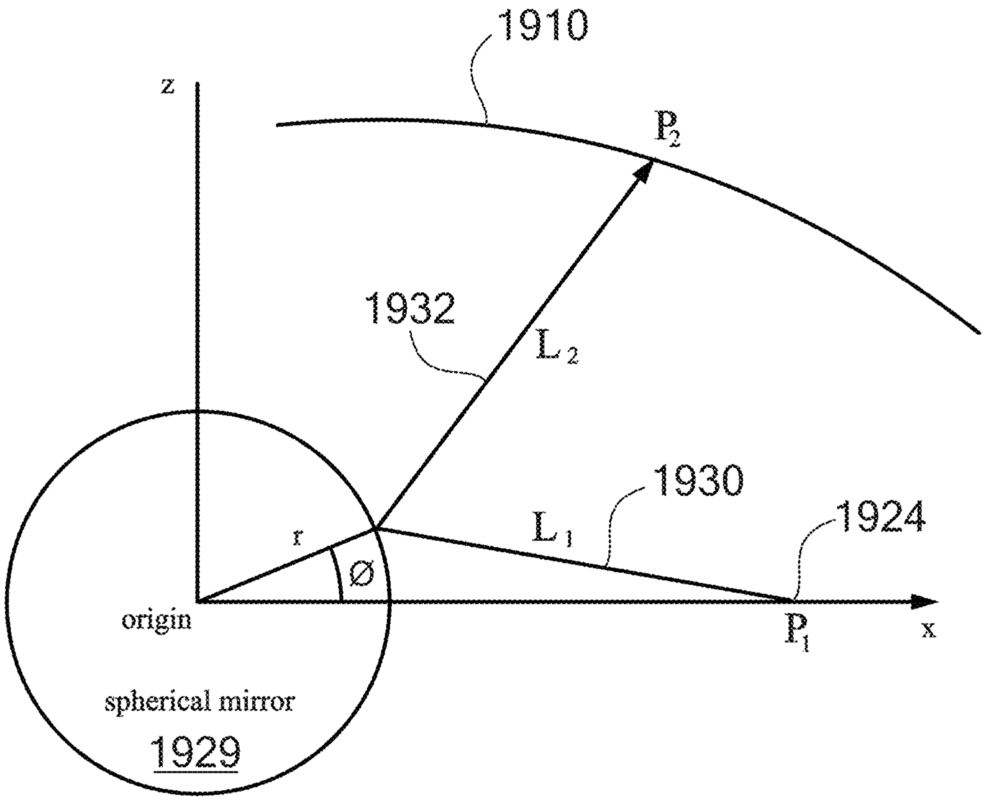
FIG. 34C is a schematic diagram that illustrates an example of a ray diagram of the imaging device of FIGS. 34A-34B projecting light onto the inner surface of the shell, according to an embodiment.
Figure 34D:
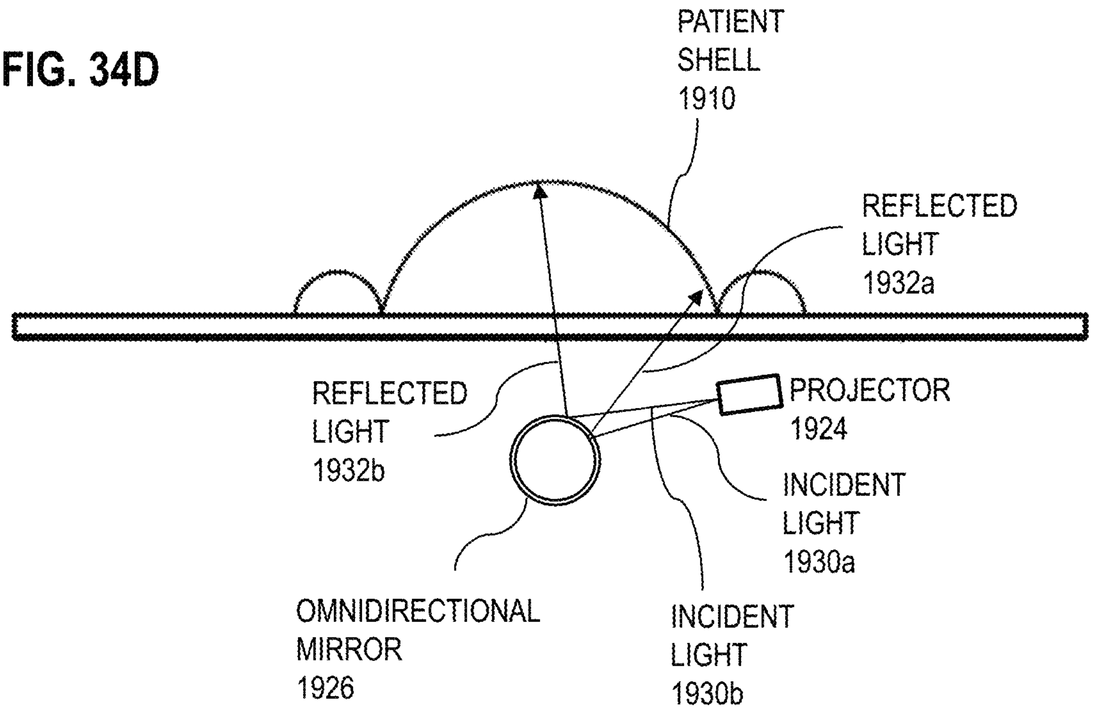
FIG. 34D is a schematic diagram that illustrates an example of a cross-sectional end view of a plurality of omnidirectional imaging devices of the system of FIG. 3, according to an embodiment.
Figure 34E:
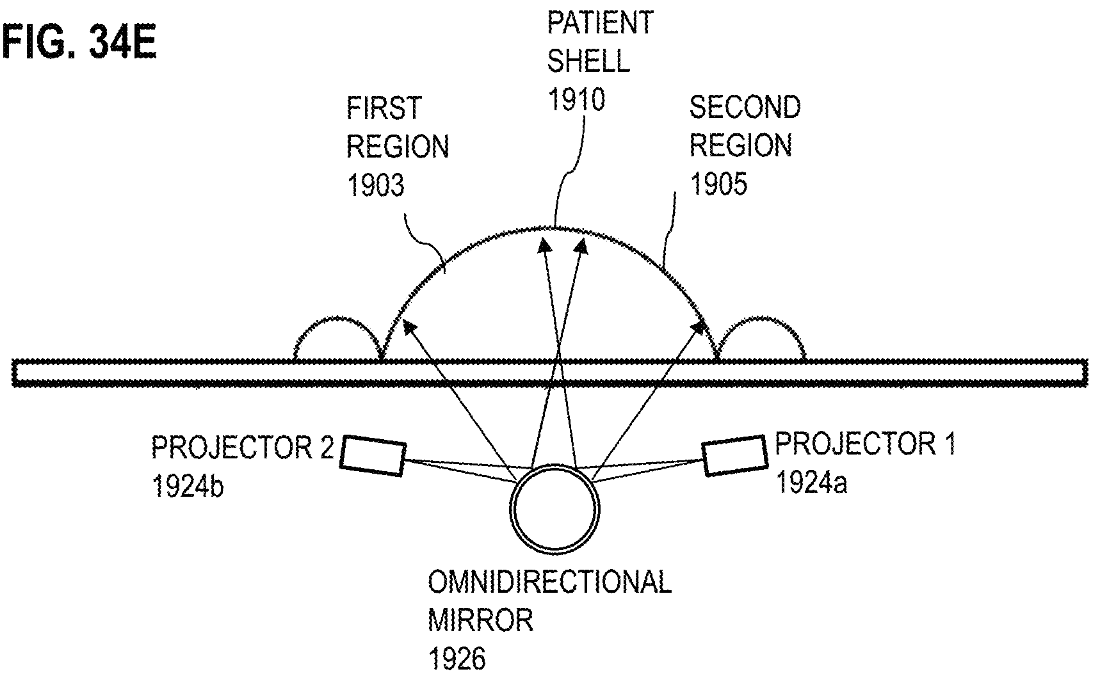
FIG. 34E is a schematic diagram that illustrates an example of a cross-sectional end view of a plurality of omnidirectional imaging devices of the system of FIG. 3, according to an embodiment.

In other embodiments, the sensor device 22 and/or optical touch sensing device 32 includes omnidirectional optical devices, as defined below. FIG. 34G is a schematic diagram that illustrates an example of a cross-sectional end view of a plurality of omnidirectional interactive devices of the system of FIG. 3, according to an embodiment. In an embodiment, FIG. 34G depicts an optical touch sensing device where an omnidirectional mirror 1926 is positioned to reflect light received from a hand 1939 moved in close proximity to the shell 1910 and the reflected light is subsequently directed into a camera 1938. In this embodiment, the camera 1938 subsequently processes the omnidirectional image of the hand 1939 to detect a presence of the hand 1939. Although a hand 1939 is depicted, the sensor device 22 can be utilized to detect the presence of any object. FIG. 34H is a schematic diagram that illustrates an example of a cross-sectional end view of a plurality of omnidirectional interactive devices of the system of FIG. 3, according to an embodiment. The arrangement of FIG. 34H is similar to the arrangement of FIG. 34G, with the exception that an omnidirectional projector 1924 is included in the arrangement of FIG. 34H to direct light on the omnidirectional mirror 1926 which is subsequently reflected by the hand 1939 back to the omnidirectional mirror 1926 and into the camera 1938 after which the hand 1939 is detected.

Although FIGS. 34G-34H depict an optical touch sensing device with omnidirectional imaging devices, in other embodiments, such an optical touch sensing device can be positioned within the patient shell 1910. FIG. 34I is a schematic diagram that illustrates an example of a cross-sectional end view of a plurality of omnidirectional interactive devices of the system of FIG. 33A, according to an embodiment. In an embodiment, a 360 degree camera 1940 is mounted within the shell 1910 and is configured to capture omnidirectional images that indicate a presence of the hand 1939 within a proximate distance of the shell 1939.

For example, in an embodiment, the camera units may be mounted in the bed system 12, with distinct optical paths from the projectors (e.g., folded optical paths). Each camera unit may comprise a pair of cameras arranged with a cold mirror such that IR light only is passed to one camera (e.g., used for touch sensing), and visible light (only) is passed to the other camera (e.g., used for calibration of the visible projector imagery), where the latter may use an IR cut filter on the camera. Mirrors may be used for folding projector and (if desired) camera unit optical paths. The camera arrangement may use mirror units that already mate with the optical breadboard, and accommodate different sized mirrors. The underside of the bed may include a form of IR illumination source to illuminate (IR) the underneath 10*a* of the human shell 10 for the purpose of touch sensing of the sensor system 22. An example of touch sensing using a spherical display prototype that has touch-sensing capabilities with an infrared camera that shares the optical path with the projector without shadowing or occlusion problems is described in "Sphere: A Multi-Touch Interactive Spherical Display" by Benko, Wilson and Balakrishnan (See research.microsoft.com), incorporated herein by reference. The IR light 28 would preferably emanate from near the cameras 30 (or a comparable optical path, so that reflected light returns to the camera), cover the area imaged by the camera, and be sufficiently bright to illuminate close objects on the opposite side—the outside/top/upper part 10*a* of the shell 10. For example, IR ring lights may be used provided the distance/range is sufficient (see FIGS. 11-12).

The invention provides a novel overall systems/methods for training healthcare professionals that combines the visual and physical shape to afford dynamic visual patient appearance (e.g., behavior, emotion, symptoms or pathology); body-specific optical touch sensing over the entire human body form and its unusual topology; interchangeable human bodies and body parts to accommodate, for example, different genders, ages, and healthcare conditions; targeted temperature feedback over the surface of the body; a tactile sense of pulse; and aural senses of a heartbeat and breathing (including anomalies for both).

The following is an example PVP system 5, with reference to FIGS. 4-10. The dimensions used herein are examples only. The actual dimensions would be adjusted to accommodate the actual components and shell size.

Example Projector Specifications: Aaxa M2 Projector. Measurements (W×D×H): 132×125×47 mm. At 68.5" distance, image was 34" wide and 26" tall (without conversion lens). At 68.5" distance, image was 50" wide and 38" tall (with conversion lens). Throw Ratio:

$$R = \frac{d}{w} = \frac{1}{2\tan\left(\frac{\alpha}{2}\right)} \quad R = \frac{d}{w} = \frac{1}{2\tan\left(\frac{\alpha}{2}\right)}$$

where α is the horizontal/vertical projection angle, d is the distance from the projector to the surface, and W is the width or height. There can be a vertical offset, so the bottom of the projected images lines up with center of lens.

Example Camera Specifications: Basler Ace acA2000-50gc. Measurements (W×D×H): 29×42×29 mm. 2048×1088 pixel @ 50 fps. Gigabit Ethernet interface with PoE. Interchangeable C-mount lenses should support a variety of mounting distances.

Figure 4:
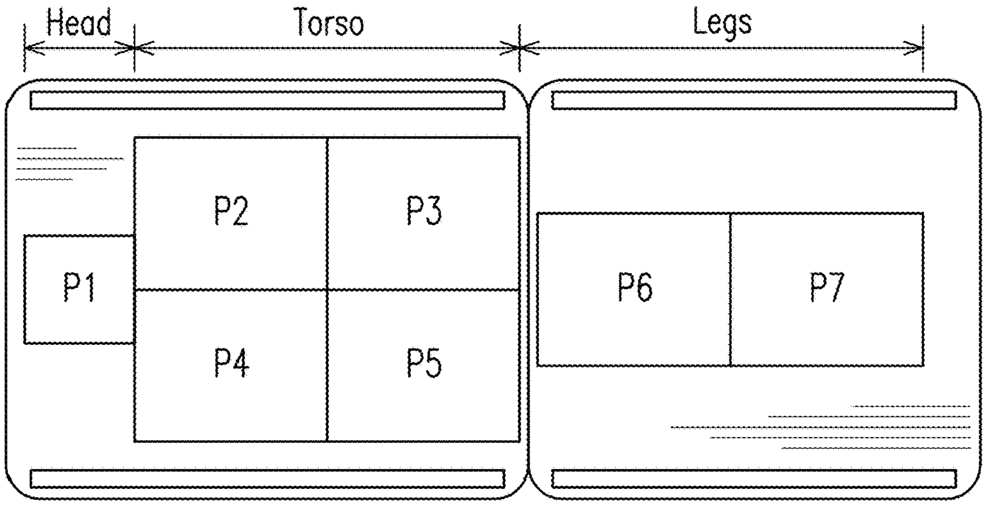
FIG. 4 shows a top-view sample layout of the placement of the projectors of the imaging system of an embodiment of the invention.

Example Projector Placement and Configuration: FIG. 4 shows a rough layout, in the top-view, of the proposed placement. In this example, seven projectors (P1 to P7) span the portion of the bed surface that will be occupied by the patient "shell" 10. Specifically, P1 covers the head, P2 through p5 cover the torso, and P6, P7 cover the legs. Since the bed 'articulates,' projectors P1 through P5 are mounted accordingly so they remain 'static' with respect to the articulated top half of the bed. In order to achieve the above-mentioned design, two different configurations are contemplated. The design is divided into 'Torso' and 'Legs' for convenience. The 'head' design is not highlighted herein, but may be very similar to those proposed for legs or torso.

Example Torso with Average Human Measurements: (See FIG. 5) Shoulder width: approximately 18"=457.2 mm; Chest height (above mattress): approximately 4.5"=114.3 mm; Torso height: approximately 30"=762 mm. For a design with 4 projectors covering the complete torso, horizontal image width at the torso is approximately 15"=381 mm; vertical image height is approximately 11.28"=286.5 mm.

Figure 6:
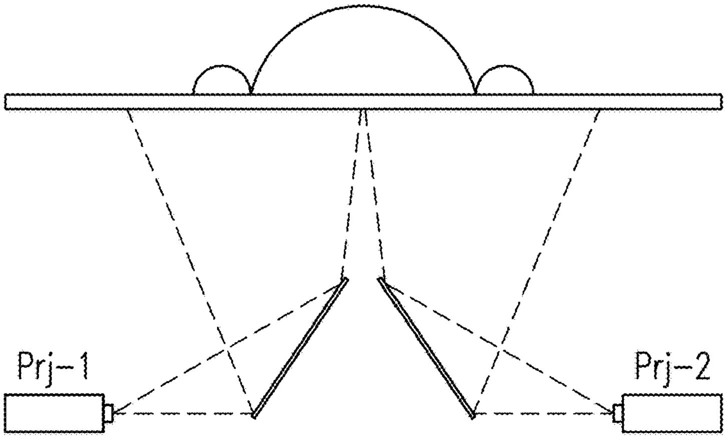
FIG. 6 shows a first design example for Torso Projection having a Single Mirror Path Folding.

FIG. 6 shows a first design example design for Torso Projection having a Single Mirror Path Folding (Design 1). The throw ratio of the projectors makes it difficult to achieve a direct projection without dropping them well beneath the surface of the bed. As a result, it was decided to use mirrors to fold the path of the projection, thereby allowing us to mount the projectors closer to the bed surface. FIG. 6 shows an example 'to-scale' version of the projection. The projectors are mounted horizontally facing inward under the outer edges of the bed, with mirrors on the inside to achieve the desired projection as shown. The measurements are shown in the following table:

TABLE 1

Single Mirror Path Folding (Design 1)

| Projector Pair | Projector height (from base of bed surface) | Mirror Distance (from projector) | Mirror Dimension (length) | Mirror Angle |
|---|---|---|---|---|
| 1 (P4, P5) | 420.5 mm (16.5") | 250 mm (9.84") | 217.7 mm (8.54") | 56° |
| 2 (P2, P3) | 420.5 mm (16.5") | 250 mm (9.84") | 210.5 mm (8.28") | −56° |

Figure 7:
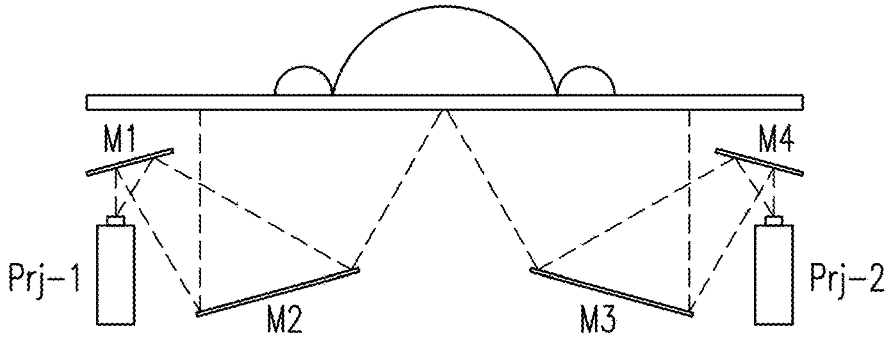
FIG. 7 shows a second design example for Torso Projection having a Dual Mirror Path Folding.

FIG. 7 shows a second design example design for Torso Projection having a Dual Mirror Path Folding. This design involves the use of two mirrors to fold the path of the projection, thereby allowing mounting of the projectors even closer to the bed surface. FIG. 7 shows an example 'to-scale' version of the projection. The projectors are vertically facing upward mounted under the outer-edges of the bed, with mirrors as shown to achieve the desired projection as shown. The measurements are shown in the following table:

TABLE 2

Dual Mirror Path Folding (Design 2)

| Projector Pair | Projector height (from base of bed surface) | Mirror Distance (from projector) | Mirror Dimensions (length) | Mirror Angle |
|---|---|---|---|---|
| 1 (P4, P5) | 282.5 mm (11.1") | M1: 76 mm (2.99") | M1: 112.5 mm (4.42") M2: 223.5 mm (8.79") | M1: 16° M2: 16° |
| 2 (P2, P3) | 282.5 mm (11.1") | M3: 76 mm (2.99") | M3: 112.5 mm (4.42") M4: 215.9 mm (8.5") | M3: −16° M4: −16° |

FIG. 8 shows a third design example for Torso Projection having a Single Mirror Crossfire Configuration. This design uses the projectors in a "cross-fire" configuration, i.e. each projector illuminates the torso side that is laterally opposite to the projector's mounting position. FIG. 8 shows an example 'to-scale' version of the projection. This placement leaves a greater buffer zone from the projectors to the edge of the bed, potentially allowing a future placement of the patient shell closer to one side of the bed. The measurements are shown in the following table:

TABLE 3

| Single Mirror Crossfire Configuration (Design 3) | | | | |
|---|---|---|---|---|
| Projector Pair | Projector height (from base of bed surface) | Mirror Distance (from projector) | Mirror Dimensions (length) | Mirror Angle |
| 1 (P4, P5) | 284.8 mm (11.21") | 163 mm (6.42") | 137.1 mm (5.4") | 14° |
| 2 (P2, P3) | 284.8 mm (11.21") | 163 mm (6.42") | 133 mm (5.24") | −14° |

FIG. 9 shows a first design example for Legs Projection having Single Mirror Path Folding. FIG. 10 shows a second design example for Legs Projection having Dual Mirror Path Folding. Two projectors may be used to cover the legs. The vertical image width at the torso may be about 12" ~=300 mm; the horizontal image height may be about 15" ~=392 mm. The same designs as those used for the torso can be used here.

Example Camera Unit and IR Illumination Placement and Configuration: The exact placement of the cameras (camera units) and associated cold mirrors, IR illumination, etc. may be determined based on the chosen shell and projector configuration. The following are two possibilities in regard to camera placement: (1) Placing them in-line with the projectors, looking into the mirrors at the projected image. This would use 7 cameras. (2) Mount them between the mirrors looking upwards. The placement of the mirrors may take the desired camera positions into account in order to not obstruct their view. Generally, the whole body could be covered by 3 cameras. To quantify the required lens focal lengths, the best and worst case can be considered for covering the complete torso with one upward-facing camera (possibility 2). Smaller focal lengths of the lens will increase the magnitude of non-linear distortions towards the edges of the image. This may result in a reduced peripheral resolution and more complicated calibration procedures. The following table lists the focal lengths for the lenses and possible models that fulfill these requirements

TABLE 4

| Camera Unit Placement: | | | |
|---|---|---|---|
| Mounting Distance | Desired image width/height at distance | Required Lens Focal Length | Lens Model |
| 282.5 mm (11.02") | 762 × 457.2 mm | 3.24 mm | Fujinon FE185C086HA 2.7 mm F/1.8 |
| 420.3 mm (16.55") | 762 × 457.2 mm | 4.85 mm | Pentax C30405KP 4.8 mm F/1.8 |

In an embodiment, omnidirectional imaging devices can be utilized instead of the imaging devices of FIGS. 6-9. FIG. 34D is a schematic diagram that illustrates an example of a cross-sectional end view of a plurality of omnidirectional imaging devices of the system 5 of FIG. 3, according to an embodiment. In FIG. 34D/34E/34G/34H the omnidirectional imaging devices are shown outside the shell, as variations of FIGS. 6-9 and FIGS. 13-14. In an embodiment, a projector 1924 is provided that outputs incident light 1930*a*, 1930*b* which is reflected off an omnidirectional mirror 1926 into a cone of reflected light 1932*a*, 1932*b* to project an image onto the shell 1910. Unlike the arrangements of FIGS. 6-9, the imaging devices (projector 1924, omnidirectional mirror 1926) are omnidirectional imaging devices, as defined below. FIG. 34E is a schematic diagram that illustrates an example of a cross-sectional end view of a plurality of omnidirectional imaging devices of the system 5 of FIG. 3, according to an embodiment. The arrangement of FIG. 34E is similar to the arrangement of FIG. 34D with the exception that the arrangement of FIG. 34E includes two projectors 1924*a*, 1924*b* mounted on opposite sides of the omnidirectional mirror 1926. In an embodiment, incident light 1930 from the first projector 1924*a* is reflected off the omnidirectional mirror 1926 to project an image in a second region 1905 of the shell 1910, whereas incident light 1930 from the second projector 1924*b* is reflected off the omnidirectional mirror 1926 to project an image in a first region 1903 of the shell 1910 that is distinct from the second region 1905. A person of ordinary skill in the art will be familiar with the possibility of, and methods for correcting, nonlinear imagery distortions on the regions of 1903 and 1905, resulting from the omnidirectional mirror. A person of ordinary skill in the art will also be familiar with methods for blending such distorted imagery in regions of overlapping projected imagery.

In some embodiments, one or more of the imaging devices 20, sensor devices 22 and/or interactive devices 24 of FIG. 1 are positioned within or enclosed by the shell 10. In these embodiments, the frame 18 and/or mounting device 14 and/or housing 12 of the system 5 are omitted. FIG. 33A is a block diagram of one example of a system 1900 including a shell 1910 with imaging devices 1920 enclosed by the shell 1910, according to an embodiment. In one embodiment, the system 1900 is self-contained (e.g. contained within the patient shell 1910). In still other embodiments, the shell 1910 has sensor devices 1922 enclosed by the shell 1910 and/or interactive devices 1924 enclosed by the shell 1910. The respective imaging devices 1920, sensor devices 1922 and/or interactive devices 1924 are similar to the imaging devices 20, sensor devices 22 and interactive devices 24, with the exception of the differences discussed herein. Additionally, the shell 1910 is similar to the shell 10 discussed previously, with the exception of the differences discussed herein. In one embodiment, the shell 1910 features one or more aspects of the shell discussed with respect to FIGS. 15-32 to the extent those features are not mutually exclusive with the shell 1910 that encloses one or more of the imaging devices 1920, sensor devices 1922 and/or interactive devices 1924.

Figure 33A:
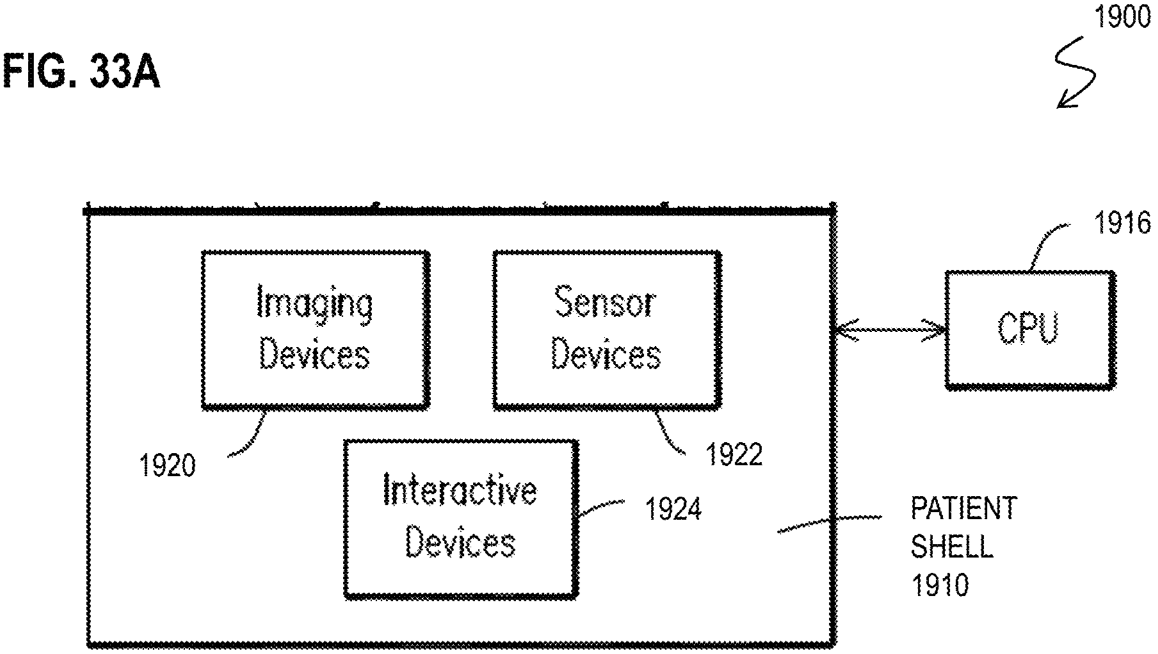
FIG. 33A is a block diagram of one example of a system including a shell with imaging devices enclosed by the shell, according to an embodiment.
Figure 33B:
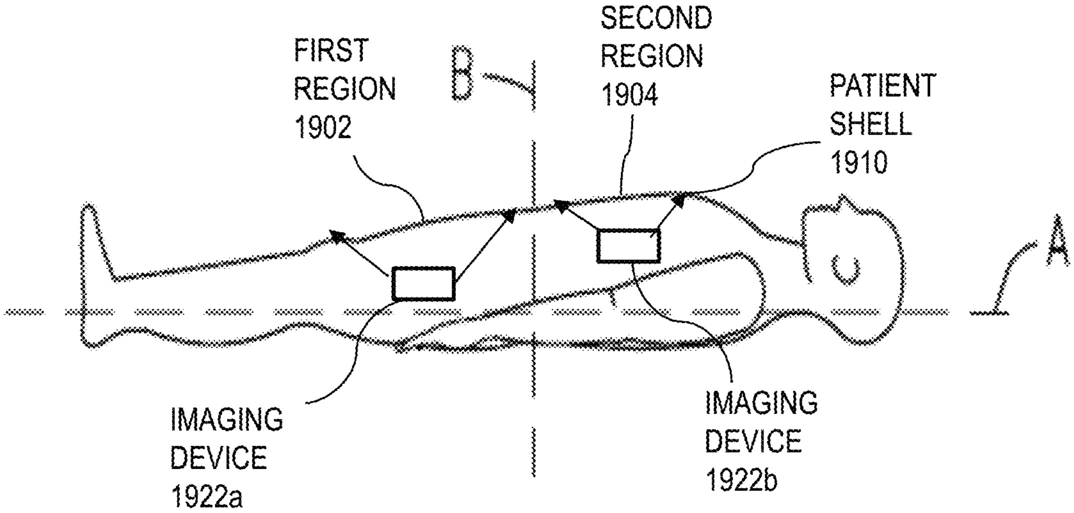
FIG. 33B is a schematic diagram that illustrates an example of a cross-sectional side view of a plurality of imaging devices enclosed by the shell of FIG. 33A, according to an embodiment.

FIG. 33B is a schematic diagram that illustrates an example of a cross-sectional side view of a plurality of imaging devices 1922*a*, 1922*b* enclosed by the shell 1910 of FIG. 33A, according to an embodiment. In one embodiment, a first imaging device 1922*a* projects an image on a first region 1902 (e.g. abdomen region) of the shell 1910 (e.g. projects the image on an inner surface of the shell 1910 so that the image is viewable by a user from the outer surface of the shell 1910). In another embodiment, a second imaging device 1922*b* projects an image on a second region 1904 (e.g. chest region) that is different from the first region 1902. Although the shell 1910 of an adult subject is depicted in FIG. 33B, in other embodiments, the shell of an infant (e.g. baby) is provided with internal imaging devices. One advantage of the embodiment of FIGS. 33A-33B is that no frame or mounting device is required to the project the image that is viewable from the outer surface of the shell 1910. This permits a greater flexibility in terms of the usage of the shell in different contexts of scenarios.

Figure 33C:
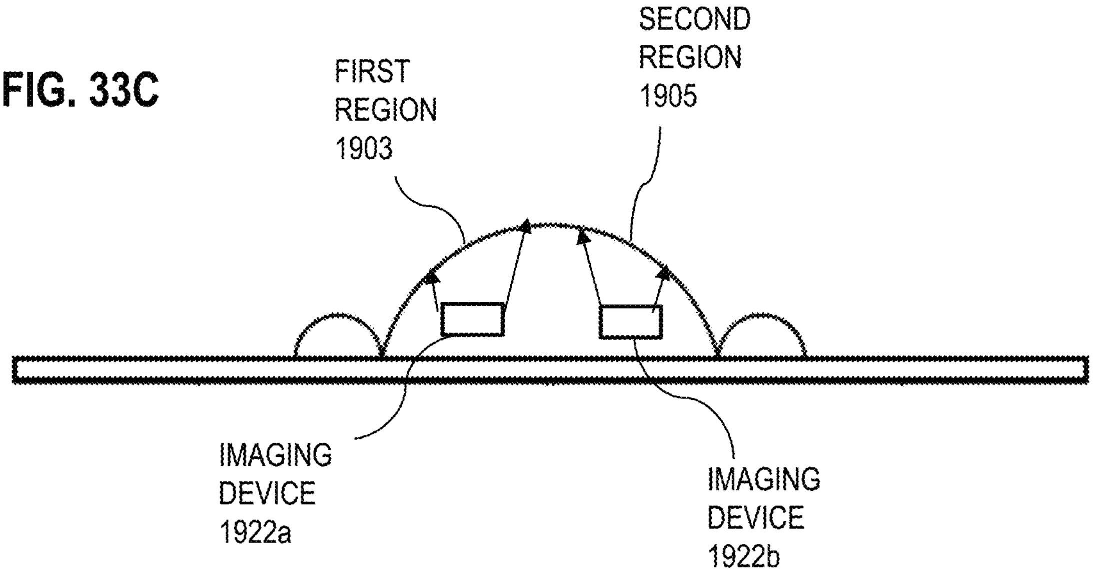
FIG. 33C is a schematic diagram that illustrates an example of a cross-sectional end view of a plurality of imaging devices enclosed by the shell of FIG. 33A, according to an embodiment.

FIG. 33C is a schematic diagram that illustrates an example of a cross-sectional end view of a plurality of imaging devices 1922*a*, 1922*b* enclosed by the shell 1910 of FIG. 33A, according to an embodiment. In the embodiment of FIG. 33C the first imaging device 1922*a* projects an image on a first region 1903 (e.g. left side) of the shell 1910 whereas the second imaging device 1922*b* projects an image on a second region 1905 (e.g. right side) of the shell 1910. In some embodiments, a combination of the imaging devices of FIG. 33B and FIG. 33C can be utilized so that images can be projected on the inner surface of the shell 1910 in both a left and right region of the shell 1910 (FIG. 33C) and two regions along a length of the subject 1910 (FIG. 33B).

In one embodiment, the imaging devices include an "omnidirectional" imaging device, which includes one or more characteristics are discussed herein. In one embodiment, a person of ordinary skill in the art would understand the concept of "omnidirectional" imaging devices (e.g. cameras or projectors) that are typically achieved by the addition of wide field-of-view optics (e.g. lenses or mirrors) to conventional imaging devices, or by mechanically locating the optical components of the imaging devices near each other such that they capture (or project) from approximately the same location, while "looking out" in different directions. When multiple individual cameras are used in a single imaging device, the (multiple) single-camera images are typically aligned with each other and "stitched together" into a single omnidirectional image. A person of ordinary skill in the art would further understand that because the omnidirectional imagery is composed from one or more conventional cameras, the resulting omnidirectional images would resemble those of conventional cameras, e.g., they would typically be rectangular, even though the angular mapping of image pixels to rays emanating from the omnidirectional device (e.g., each specified as azimuth/yaw and elevation/pitch angles) is typically not regular. For example, an omnidirectional image might be organized and represented in a rectangular fashion (e.g., having rows and columns) and yet comprise some pixels that were imaged near the top or "pole" of a hemispherical mirror and are angularly dense (e.g. the pole is very small), and some pixels that were imaged near the "equator" and angularly sparse (e.g. the equator is relatively large). In an example embodiment, the omnidirectional images are transmitted and received from the imaging devices 1920 and the CPU 1916 and/or the CPU 1916 is configured to process the omnidirectional images as discussed herein. As such, in one embodiment, omnidirectional images—once assembled (e.g. if created from multiple cameras) would be handled (e.g. by the CPU 1916—captured, recorded, transferred, etc.) the same as conventional images. Omnidirectional projectors could be used to project dynamic imagery all around a point inside an enclosed shell 1910, for example, and multiple overlapping omnidirectional cameras might be used to cover the entire interior of the shell—much like multiple overlapping conventional projectors can be used. Just as with conventional projectors, omnidirectional projectors could be used for calibration of the cameras or other optical components, and for presenting the appearance of the patient on (all over) the shell. Omnidirectional cameras could be used to capture dynamic imagery of the shell all around a point inside an enclosed shell, for example, and multiple overlapping omnidirectional cameras might be used to cover the entire interior of the shell-much like multiple overlapping conventional cameras can be used. Just as with conventional cameras, omnidirectional cameras could be used for calibration of the projectors or other optical components, and for touch sensing on the shell.

A person of ordinary skill in the art will be familiar with the design and support of various omnidirectional camera approaches, from at least as early as 1996 when Vic Nalawa at Bell Laboratories wrote a technical report on the subject. (see [5], V. Nalwa. A true omnidirectional viewer. Technical report, Bell Laboratories, Holmdel, NJ 07733, February 1996 which is incorporated by reference herein.) In one embodiment, plexiglass or other hard and clear plastic can be used to support a camera above an omnidirectional mirror. In an embodiment, the camera itself will be seen in the middle of the image (e.g., a small artifact). In some embodiments, a human-shaped frame (e.g., metal frame) could be used to join two or more shell pieces to create a complete human (or other) body as in FIG. 34J and FIG. 34K. In an embodiment, projectors, cameras, and/or omnidirectional components could be affixed to the frame. A person of ordinary skill in the art will understand that as long as power can be achieved inside such a complete human shell, there are a variety of ways to generate and acquire imagery using the internal projectors and cameras (e.g. through the use of wireless technology, where the CPU 1916 is in wireless communication with the imaging devices 1920). In still other embodiments, the CPU 1916 can be in wired communication with the imaging devices 1920 (e.g. cable directed through small openings in the shell 1910 between the CPU 1916 and respective omnidirectional components). In another embodiment, a person of ordinary skill in the art would also appreciate that the unit could be powered by internal rechargeable batteries that are recharged through a variety of means, including possibly inductive methods.

In one example embodiment, the imaging device 1922 is made omnidirectional by including a spherical mirror and a projector, as disclosed in [1] and [2], which are both incorporated by reference herein. FIG. 34A is a schematic diagram that illustrates an example of a top view of an imaging device 1922 of FIG. 33B within the shell 1910, according to an embodiment. In an embodiment, the imaging device 1922 includes an optical source that generates an optical signal and one or more optics (e.g. lens, mirror) that are reflective and/or refractive that direct the optical signal over the appropriate region (e.g. first region or second region as depicted in FIGS. 33B, 33C). In some embodiments, the optical source is a projector 1924 that is similar to the projector disclosed in [1] and [2] with the exception that the size of the projector is scaled so to fit within the shell 1910. In another example embodiment, the optic includes an omnidirectional mirror 1926 that is similar to the spherical mirror disclosed in [1] and [2] except scaled to be used within the shell 1910. The transmission and redirection of the light from the projector 1924 to the omnidirectional mirror 1926 and to the inner surface of the shell 1910 is similar to the transmission and redirection discussed in [1] and [2] for hemispherical domes, with the exception that the scale is adjusted based on the interior of the shell 1910. As depicted in FIG. 34A incident light 1930 from the projector 1924 is reflected by the spherical mirror 1930 as reflected light 1932*a*, 1932*b*, 1932*c* in various directions so that the collective reflected light 1932 projects the image to the region 1902 or 1904 (FIG. 33B) or the region 1903 or 1905 (FIG. 33C). FIG. 34B is a schematic diagram that illustrates an example of a side view of an imaging device 1922 of FIG. 33B within the shell 1910, according to an embodiment. FIG. 34C is a schematic diagram that illustrates an example of a ray diagram of the imaging device 1922 of FIGS. 34A-34B reflecting light 1932 onto the inner surface of the shell 1910, according to an embodiment. The ray diagram of FIG. 34C depicts the projector 1924 (P1) that transmits the incident light 1930 (along line L1) and is reflected as reflected light 1932 (along line L2) to generate the image (at point P2) on the inner surface of the shell 1910 (which is subsequently viewable from the outer surface of the shell 1910.

Figure 34F:
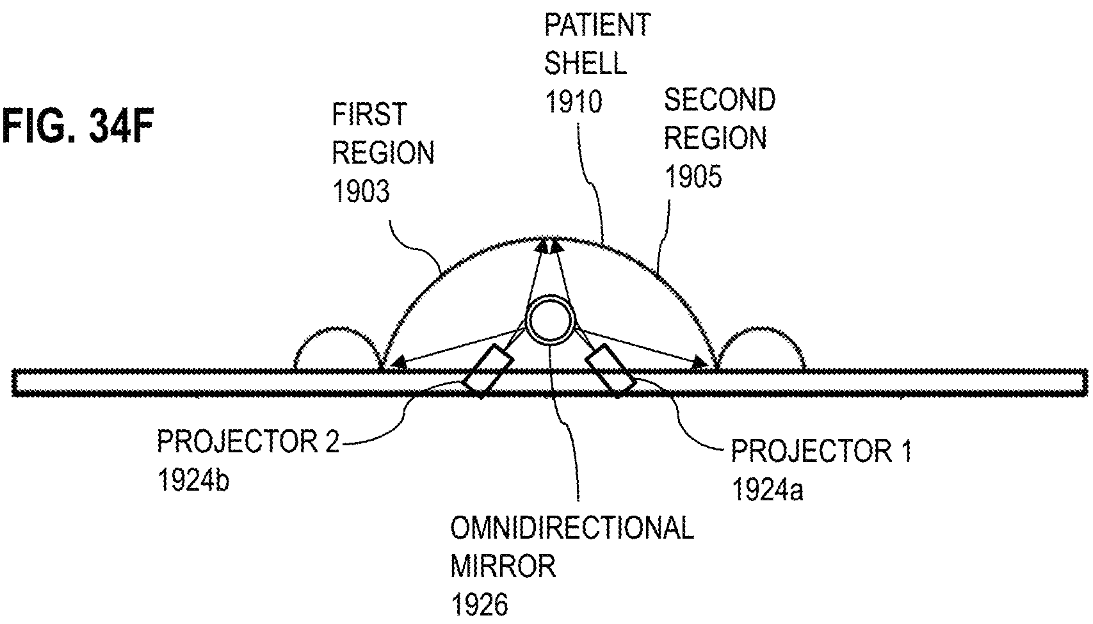
FIG. 34F is a schematic diagram that illustrates an example of a cross-sectional end view of a plurality of omnidirectional imaging devices of the system of FIG. 33A, according to an embodiment.
Figure 34G:
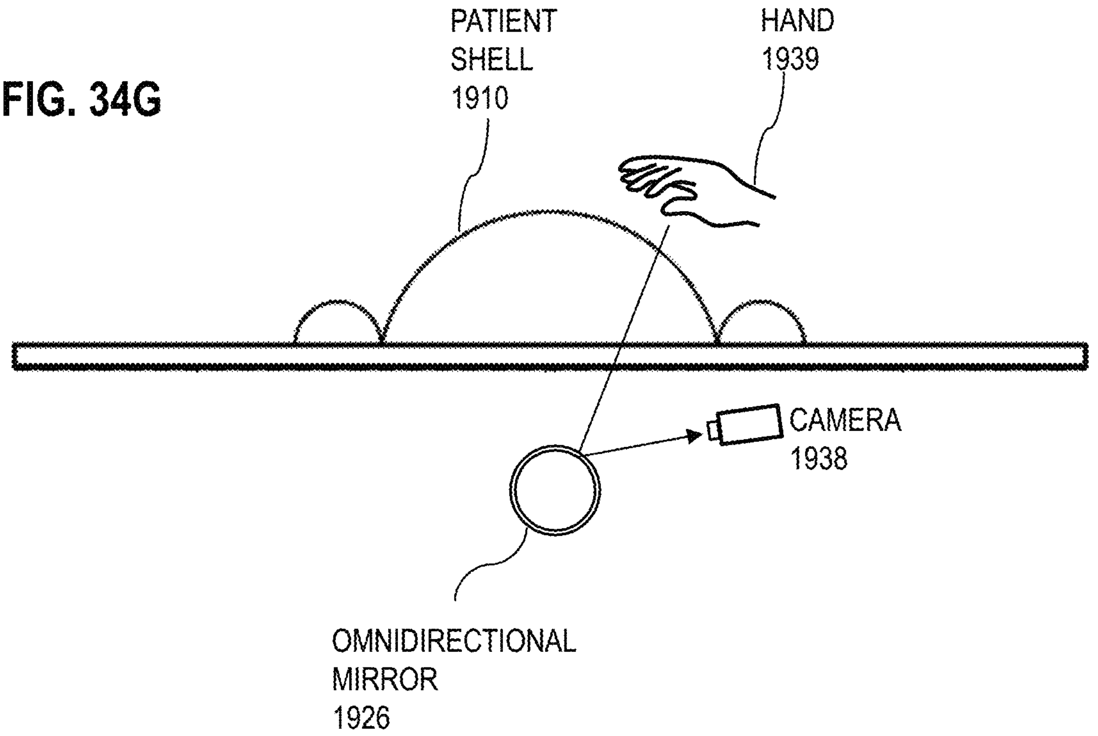
FIG. 34G is a schematic diagram that illustrates an example of a cross-sectional end view of a plurality of omnidirectional interactive devices of the system of FIG. 3, according to an embodiment.
Figure 34H:
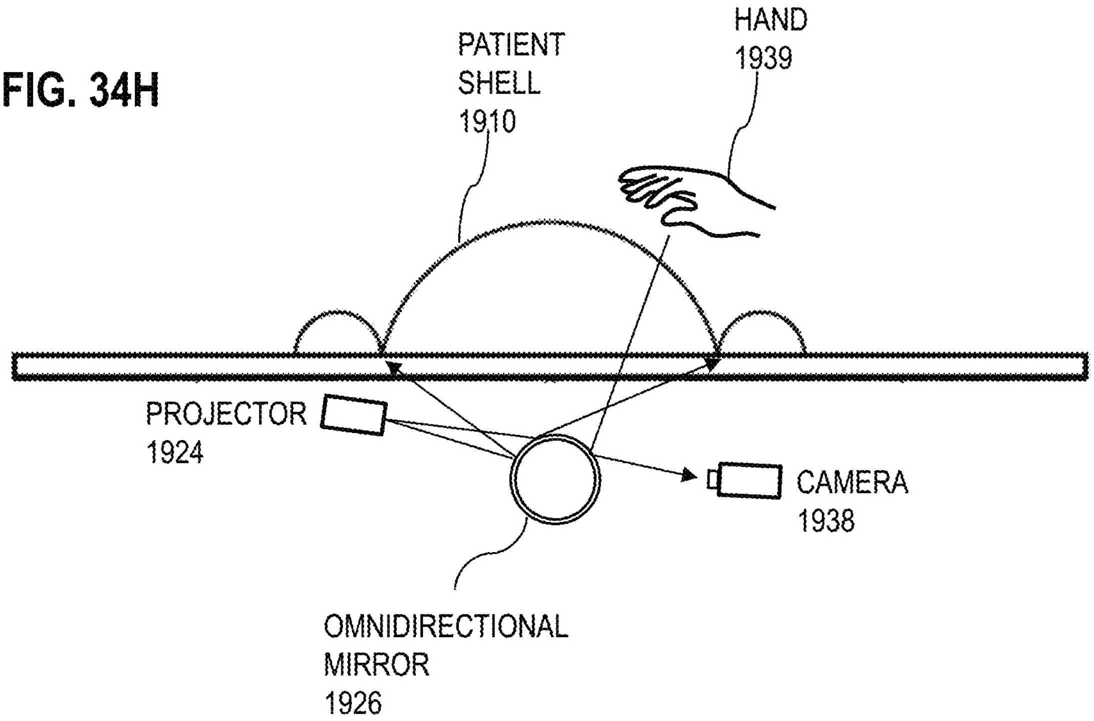
FIG. 34H is a schematic diagram that illustrates an example of a cross-sectional end view of a plurality of omnidirectional interactive devices of the system of FIG. 3, according to an embodiment.
Figure 34I:
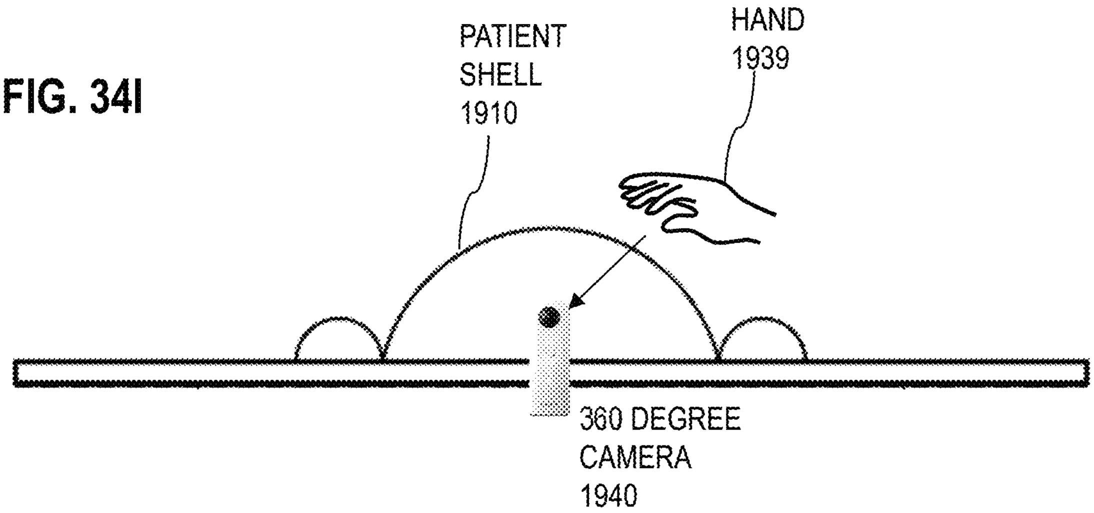
FIG. 34I is a schematic diagram that illustrates an example of a cross-sectional end view of a plurality of omnidirectional interactive devices of the system of FIG. 33A, according to an embodiment.

FIG. 34F is a schematic diagram that illustrates an example of a cross-sectional end view of a plurality of omnidirectional imaging devices of the system of FIG. 33A, according to an embodiment. In an embodiment, the arrangement of FIG. 34F includes an omnidirectional mirror 1926 mounted within the shell 1910 (e.g. using any means appreciated by one skilled in the art) and a pair of projectors 1924*a*, 1924*b* mounted within the shell 1910 (e.g. using any means appreciated by one skilled in the art). In one embodiment, incident light 1930 from the projector 1924*b* is reflected off the omnidirectional mirror 1926 and projects an image along the shell 1910 in a first region 1903. In another embodiment, incident light 1930 from the projector 1924*a* is reflected off the omnidirectional mirror 1926 and projects an image along the shell 1910 in a second region 1905 that is adjacent and/or different than the first region 1903. A person of ordinary skill in the art will be familiar with the possibility of, and methods for correcting, nonlinear imagery distortions on the regions of 1903, resulting from the omnidirectional mirror. A person of ordinary skill in the art will also be familiar with methods for blending such distorted imagery in regions of overlapping projected imagery.

Figure 34J:
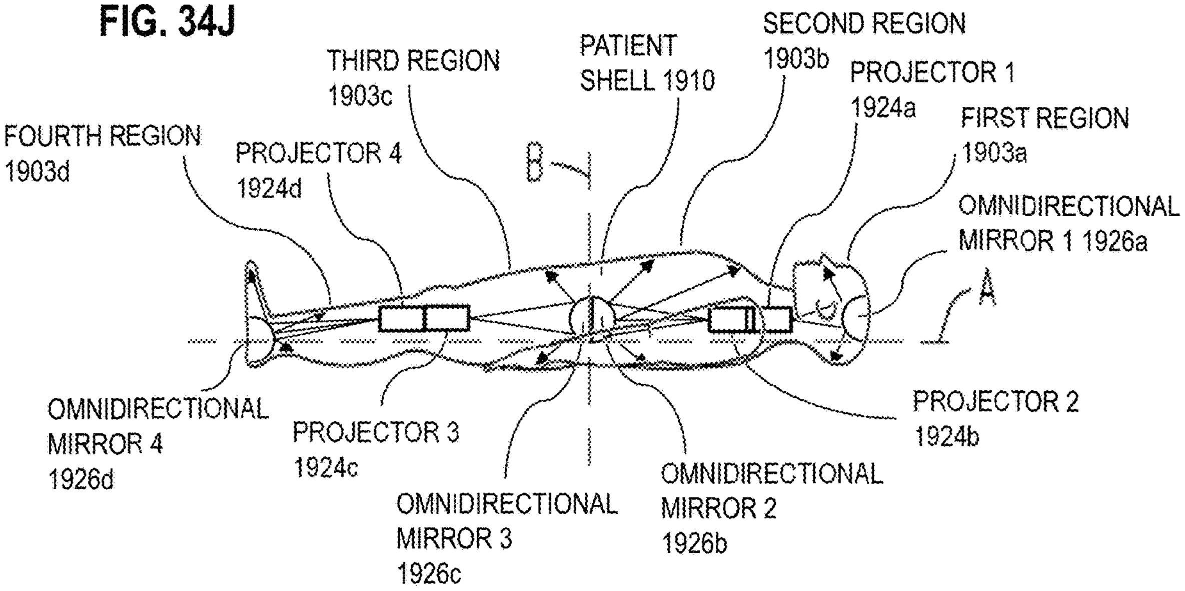
FIG. 34J is a schematic diagram that illustrates an example of a cross-sectional side view of a plurality of omnidirectional imaging devices contained within the shell of the system of FIG. 33A and FIG. 34F, according to an embodiment.
Figure 34K:
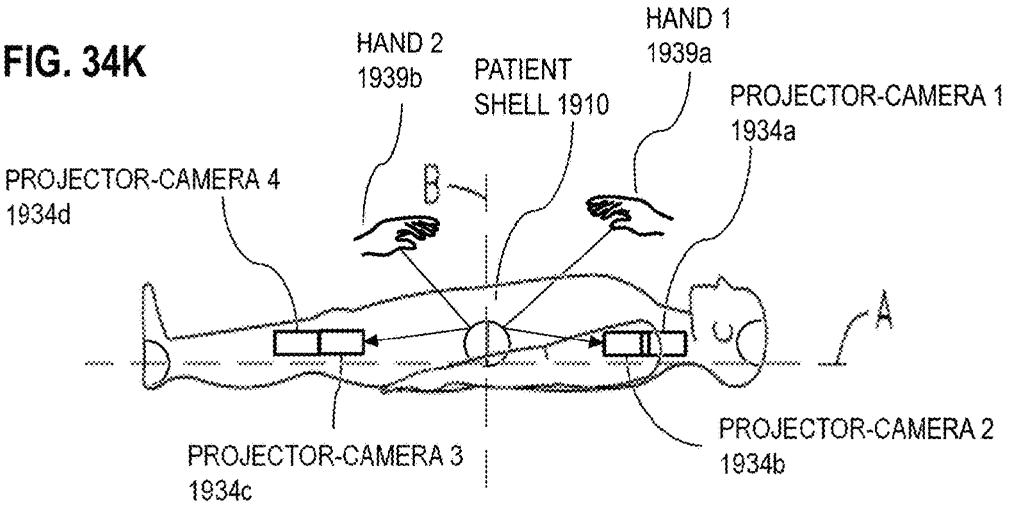
FIG. 34K is a schematic diagram that illustrates an example of a cross-sectional side view of a plurality of omnidirectional imaging devices contained within the shell of the system of FIGS. 33A and 34J, according to an embodiment.

FIG. 34J is a schematic diagram that illustrates an example of a cross-sectional side view of a plurality of omnidirectional imaging devices enclosed within the shell of the system of FIG. 33A and FIG. 33B, according to an embodiment. In an embodiment, the arrangement of FIG. 34J includes four omnidirectional mirrors 1926*a*, 1926*b*, 1926*c*, and 1926*d* mounted within the shell 1910 (e.g. using any means appreciated by one skilled in the art) and four projectors 1924*a*, 1924*b*, 1924*c*, and 1924*d* mounted completely within a surrounding shell 1910, possibly comprised from multiple shell pieces arranged and supported to form a complete surrounding shell (e.g., using any means appreciated by one skilled in the art). In one embodiment, a first pair of omnidirectional projectors 1924*a*, 1924*b* are positioned in a first region (e.g. upper region) of the shell 1910, where the projectors 1924*a*, 1924*b* are configured to direct light in opposite directions. In one example embodiment, the projectors 1924*a*, 1924*b* are connected (e.g. rear end of projector 1924*a* connected to rear end of projectors 1924*b*). In another embodiment, a second pair of omnidirectional projectors 1924*c*, 1924*d* are positioned in a second region (e.g. lower region) of the shell 1910, where each projector 1924*c*, 1924*d* are configured to direct light in opposite directions. In another embodiment, a first pair of omnidirectional mirrors 1926*a*, 1926*b* are provided in the first region (e.g. upper region) and are spaced apart so that the first pair of projectors 1924*a*, 1924*b* are positioned between the spaced apart omnidirectional mirrors 1926*a*, 1926*b* and/or are configured to direct light at the respective omnidirectional mirrors 1926*a*, 1926*b*. In another embodiment, a second pair of omnidirectional mirrors 1926*a*, 1926*b* are provided in the second region (e.g. lower region) and are spaced apart so that the second pair of projectors 1924*c*, 1924*d* are positioned between the spaced apart omnidirectional mirrors 1926*c*, 1926*d* and/or are configured to direct light at the respective omnidirectional mirrors 1926*c*, 1926*d*. Although four omnidirectional mirrors and four projectors are mounted within the shell 1910 in FIG. 34J, in other embodiments less or more than four omnidirectional mirrors and/or less or more than four projectors can be mounted within the shell 1910. In one embodiment, incident light from a first projector 1924*a* (e.g. positioned within a neck of the shell 1910) is reflected off a first omnidirectional mirror 1926*a* (e.g. positioned within a head of the shell 1910) and projects an image along the shell 1910 in a first region 1903*a* (e.g. one or more images of facial features of the shell 1910 or features along the top or back of the head). In another embodiment, incident light from a second projector 1924*b* (e.g. positioned within an upper torso region or chest region of the shell 1919) is reflected off a second omnidirectional mirror 1926*b* (e.g. positioned in a central region such as an abdomen region of the shell 1910) and projects an image along the shell 1910 in a second region 1903*b* (e.g. chest and/or back region of the shell 1910) that is adjacent and/or different than, but might overlap, the first region 1903*a*. In another embodiment, incident light from a third projector 1924*c* (e.g. positioned within a lower region such as adjacent a knee region of the shell 1910) is reflected off a third omnidirectional mirror 1926*c* (e.g. positioned within the central region of the shell 1910) and projects an image along the shell 1910 in a third region 1903*c* (e.g. thigh and/or buttock region of the shell 1910) that is adjacent and/or different than, but might overlap, the second region 1903*b*. In another embodiment, incident light from a fourth projector 1924*d* (e.g. positioned within the lower region) is reflected off a fourth omnidirectional mirror 1926*d* (e.g. positioned within a foot region of the shell 1910) and projects an image along the shell 1910 in a fourth region 1903*d* (e.g. leg region and/or foot region of the shell 1910) that is adjacent and/or different than, but might overlap, the third region 1903*d*.

A person of ordinary skill in the art will be familiar with the concept of projector-camera systems ("procam systems") as the practice of pairing a projector with a camera that is either mounted proximal to the projector, or possibly mounted inside the projector. A person of ordinary skill in the art will appreciate that in the latter instance, the camera and projector can share some portion of a collinear optical path to the omnidirectional mirror, as described and prototyped for example by John Underkofler in his Luminous Room. (See [6] J. Underkoffler. A View From the Luminous Room. Personal Technologies, 1 (2): 49-59, June 1997, which is incorporated by reference herein) In an embodiment related to that depicted in FIG. 34J, the arrangement of FIG. 34K includes four projector-camera units 1934*a*, 1934*b*, 1934*c*, and 1934*d*, each paired with an omnidirectional mirror as depicted in the arrangement of FIG. 34J. A person of ordinary skill in the art will appreciate that the projectors and cameras can be used simultaneously for rendering imagery onto the shell regions 1903*a*, 1903*b*, 1903*c*, and 1903*d* as depicted in FIG. 34J, and sensing touch as described herein. Additionally, in another embodiment, the omnidirectional mirrors 1926*b*, 1926*c* of FIGS. 34J-34K can be used to detect the presence of nearby objects (e.g. hand 1939*a* and/or hand 1939*b*) based on reflection of incident light from the nearby objects which is directed to the projector-cameras 1934*a*, 1934*b*, 1934*c*, 1934*d*.

In other example embodiments, the imaging device 1922 is an omnidirectional degree (e.g. 360 degree) camera, that operates using technology similar to Fullview® cameras (www.fullview.com) and/or Insta360® cameras (http://www.instal360.com) and/or Viar360® cameras (viar360.com) and/or Ozo® cameras (www.ozo.nokia.com).

For example, in other example embodiments, the imaging device 1922 is a hemispherical projector (e.g. a specific form of an omnidirectional projector), that operates using technology similar to Newtonian® 3 projector manufactured by Go Dome of Houston Texas (www.go-dome.com/dome-products/newtonian-projection-system-2/) and/or Go-Vex® projector manufactured by Go Dome of Houston Texas (www.go-dome.com/dome-products/newtonian-projection-system-2/go-vex/) and/or Go-Frame® projector manufactured by Go Dome of Houston Texas (www.go-dome.com/dome-products/newtonian-projection-system-2/go-frame/) and/or a fisheye lens or spherical lens as disclosed by [3] which is incorporated by reference herein. As indicated above, the imagery for such an omnidirectional projector would be much the same as a conventional projector, except that the angular mapping of pixels would be irregular, with the angular density varying along the surface of the sphere as discussed above. A person of ordinary skill in the art would understand that this mapping is just a variation of the normal mapping.

An exemplary system for implementing the invention includes a computing device or a network of computing devices. In a basic configuration, computing device may include any type of stationary computing device or a mobile computing device, including but not limited to the computer system as discussed below in reference to FIG. 30 and/or the chip set as discussed below with reference to FIG. 31 and/or the mobile device as discussed below with reference to FIG. 32. Computing device typically includes at least one processing unit and system memory. Computing device may also have input device(s) such as a keyboard, mouse, pen, voice input device, touch input device, etc. Output device(s) such as a display, speakers, printer, etc. may also be included. A computing device also contains communication connection(s) that allow the device to communicate with other computing devices and the PVP system, for example over a network or a wireless network.

A number of different configurations of the described embodiments exist. For example, the core elements of the disclosed PVP system (device/apparatus, method, computer readable medium) can be realized in other physical configurations or arrangements beyond that associated with a bed. For example, the same elements could be used in chair-like (seated patient), standing, or other postural embodiments appropriate for the training application. In yet another example, the same elements could be used to flip the shell on its front side so that the back side (e.g. back area, back of head, back of legs, etc) can be viewed. This could support more realistic simulations of such scenarios as preliminary exams and even blood tests, where a patient is typically sitting upright; testicular or other exams where the patient is typically standing; or prostate exams where a patient might be bending over, or on their side for example. Other configurations are contemplated herein that would be evident to a person of ordinary skill in the art.

Figure 26:
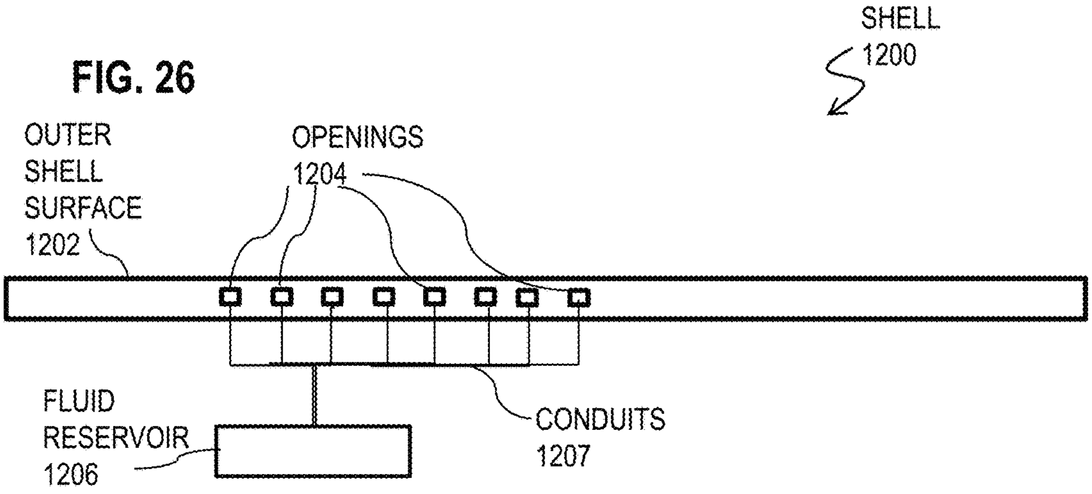
FIG. 26 is an image that illustrates an example of a plurality of openings defined by the outer surface of the shell and a fluid reservoir communicatively coupled to the openings, according to an embodiment.

In another example, hybrid combinations of the described embodiments with elements of other training body parts may be provided. The elements of the disclosed PVP system (device/apparatus, method, computer readable medium) can be combined with other training-related human body elements in a hybrid fashion. For example, a portion of the human body shell corresponding to the upper arm could be replaced with a replica arm designed for practicing the insertion and removal of intravenous lines. Examples of such arms include the "Multi-Venous IV Training Arm" and the "Arterial Arm Stick Kit" offered by Laerdal Medical. Similarly, the entire projected torso of the disclosed embodiments could be replaced by a training torso such as the "Laerdal IV Torso" (also offered by Laerdal Medical). Such hybrid configurations would result in systems that can be used to train medical tasks that are specific to a particular body part (e.g., insertion and removal of intravenous lines) while the remainder of the patient is illuminated with computer graphics depicting other symptoms, patient behavior, emotion, etc. as described herein. In one embodiment 111 shown in FIG. 11, a hybrid system is shown comprising a PV human body shell 115 onto which images may be projected that also has a replica arm 112, that is suitable for practicing injections or blood removal. FIG. 26 is an image that illustrates an example of a plurality of openings 1204 defined by the outer surface of the shell 1200 and a fluid reservoir 1206 communicatively coupled to the openings, according to an embodiment. In an embodiment, the outer surface 1202 of the shell 1200 defines a plurality of openings 1204 and the interface devices includes a fluid reservoir 1206 that is communicatively coupled to the plurality of openings with a respective plurality of conduits 1207. The fluid reservoir 1206 is configured to transmit fluid (e.g. liquid, gas, etc.) through the plurality of openings 1204 in the outer surface based on a signal received from the computing unit 16. In an embodiment, the fluid reservoir 1206 is a reservoir of simulated blood that is configured to transmit simulated blood through the conduits 1207 and through the plurality of openings 1204 based on the signal received from the computing unit 16. In another embodiment, the fluid reservoir 1206 is a reservoir of gas that simulates a biological process (e.g. decaying flesh, sweat, body odor, urination and/or flatulence, etc.) involving the human body. The fluid reservoir 1206 is configured to transmit the gas through the conduits 1207 and the plurality of openings 1204 based on the signal received from the computing unit 16. In an example embodiment, specific training simulations are provided that determine an output of the fluids, e.g. to simulate a patient that is hypotensive, a decreased urine output is simulated. In yet another example embodiment, a drop in blood pressure can be calculated based on the amount of virtual blood that is output through the openings 1204. In a further example embodiment, a standard wound diagnostic task is provided that simulates how "wound rot" smells like. In still other embodiments, larger sized holes may be provided over the outer surface of the shell 10 (e.g. arteries) to simulate the spurting of blood from these regions of the patient's body.

Figure 11:
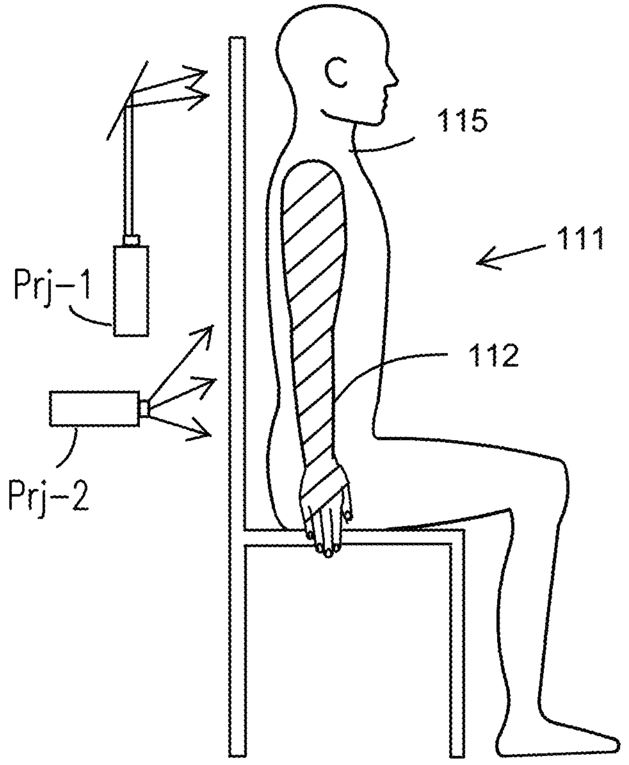
FIG. 11 shows a diagram of a hybrid system embodiment that includes a Physical Virtual (PV) human body shell onto which images may be projected that also has a replica arm that is suitable for practicing injections or blood removal.
Figure 12:
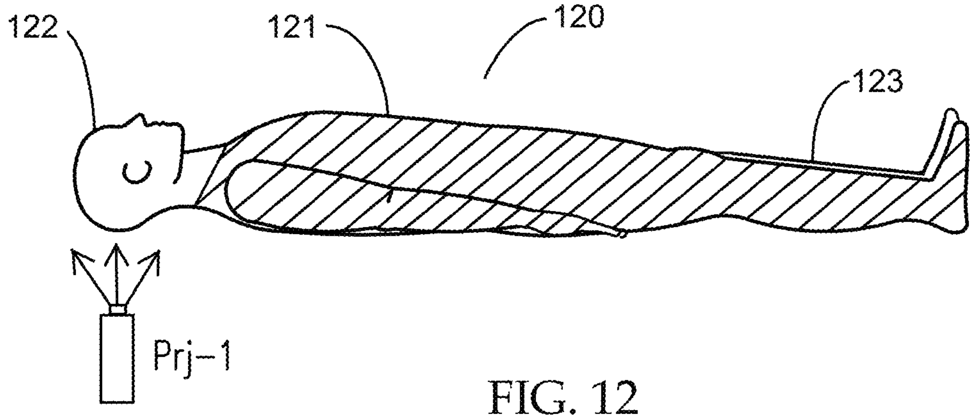
FIG. 12 shows a patient simulator mannequin embodiment that has been modified to replace the head portion with a PV head shell component onto which images can be projected.
Figure 16A:
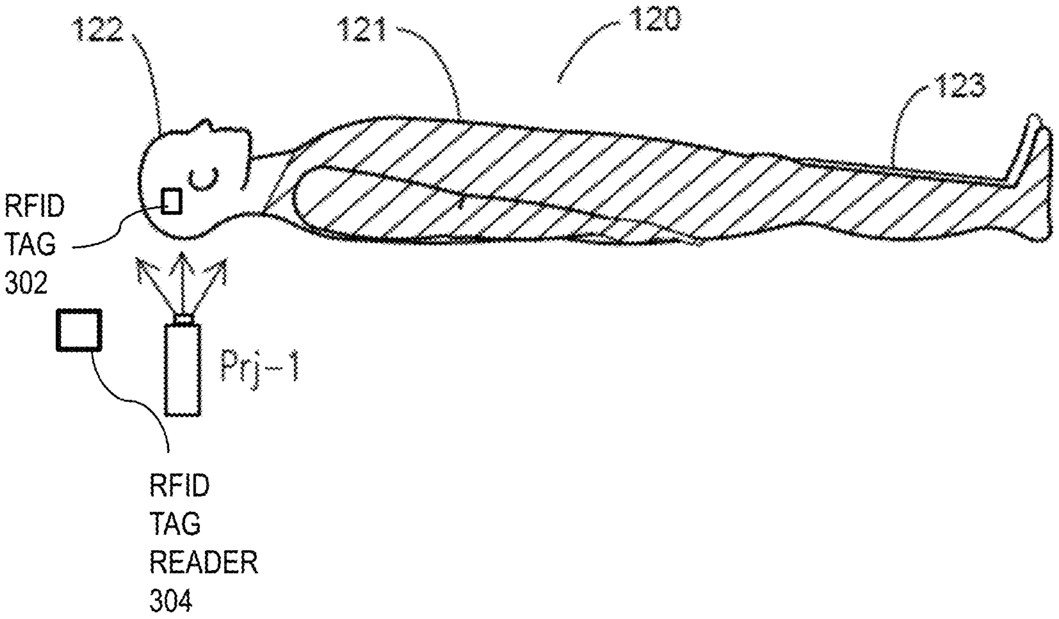
FIGS. 16A-16B are images that illustrate an example of a reconfigurable or alternate configuration part (e.g., prone or seated) with identifying indicia, according to an embodiment.
Figure 16B:
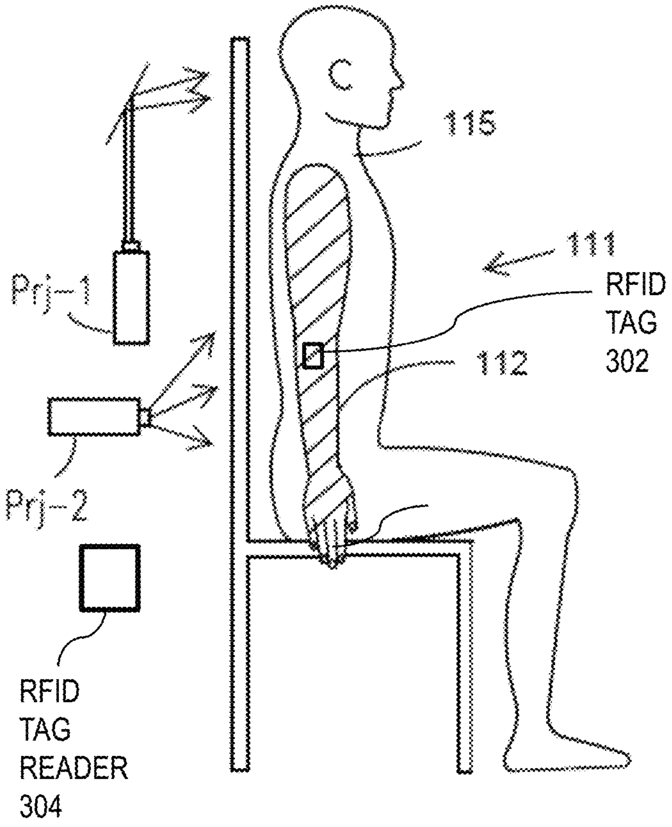

Alternatively, other training-related human forms could be combined with core body elements of the disclosed PVP system in a hybrid fashion. For example, the head of a Laerdal patient simulator (also known as a "mannequin" or "manikin") could be removed and replaced by a PVP head element to simulate a combination of body physiology from the mannequin body with facial expressions, temperature, and touch sensing (for example) from the PVP head. Similarly, a real human patient actor (e.g., a "standardized patient") could hide their arm behind their body to allow it to, in effect, be replaced by a PVP arm, allowing their arm to exhibit dynamic visual and temperature symptoms, for example. Such hybrid configurations would result in systems that can be used to train full-body medical tasks that would benefit from the complex simulation of conventional mannequins while the head of the patient is illuminated with computer graphics to depict speaking, facial expressions, emotion, visual/temperature symptoms related to the face as described herein. In one embodiment 120, as shown in FIG. 12, a patient simulator mannequin 121 has been modified to replace the head portion with a PV head shell component 122, onto which images can be projected. In an embodiment, as depicted in FIGS. 11-12, the shell is a patient virtual overlay adapted for overlaying a replica or real body part (e.g. PV head shell component 122). In an example embodiment, real body parts from a cadaver can be integrated into the PVP (e.g., with front projection). In still other embodiments, as depicted in FIGS. 11-12, the system includes a mannequin 121 replicating a patient body including the shell of at least one body part (e.g. replica arm 112). In one example embodiment, the system can be used for "reverse" body part modularity (e.g. use PV for part of an existing/modular manikin/simulator). FIGS. 16A-16B are images that illustrate an example of an interchangeable part (e.g. replica arm 121) with identifying indicia used in the shell 10 of the bed system 5 of FIG. 3 according to an embodiment. In one embodiment, the shell 10 includes one or more interchangeable parts and each interchangeable part has identifying indicia such that one or more interface devices are configured to read the identifying indicia when the interchangeable part is connected to the shell 10. In some embodiments, an input sensor detects when a part is connected to a shell. In one embodiment, the input sensor triggers the RFID reader 304. In another embodiment, the RFID reader 304 is constantly scanning to detect for a signal from the input sensor indicating that the part is connected to the shell. In another embodiment, the interface device is further configured to transmit a signal to the computing unit 16 with the read identifying indicia. In an example embodiment, the identifying indicia is one of an optical tag or RFID tag (Radio Frequency Identification) tag 302 and the interface device is a reader 304 of the optical tag and RFID tag 302. In another example embodiment, automatic detection or identification of hybrid parts and/or pieces can be used for integrated behavior, appearance, etc.

The above embodiments are merely a few examples wherein many similar hybrid combinations could be realized and are contemplated herein. Similarly, there are many application areas that are contemplated herein, including for example breast exams (e.g., a PVP incorporating a physical breast replica with pressure sensors such as disclosed by Kotranza, Lind, and Lok) being able to detect nodules, lumps, tumors and/or masses; abdominal exams; testicular exams; gynecological exams; prostate exams; catheter insertions; and treatment associated with severed or amputated/missing limbs.

In a further example embodiment, Physical-Virtual Overlay Shells for Humans or Mannequins may be provided. Herein, the core elements of the disclosed Physical-Virtual Patient (PVP) system (device/apparatus, method, computer readable medium) can be realized in relatively thin PV structures that are formed (roughly or precisely) to conform over or around a body part of a real human or a physical patient simulator (also known as a "mannequin" or "manikin"), resembling for example a shin pad or knee pad. For example, the embodiment of 120 also comprises a PV overlay shell 123 over the shin of the mannequin 121. Such PV overlay shells could be worn or placed over (e.g., on top of) a corresponding body part such as an arm, hand leg, foot, torso, or head. The visual aspects of such PV overlay shells could be realized in various ways, for example using projectors in a "front projection" configuration or flexible emissive displays, e.g., flexible OLED displays. The temperature effects and touch sensing could also be realized in various mechanisms including, for example, heating/cooling pipes and light pipes. Microphones, surface-mount slim speakers, and other miniature audio components could provide sound input and output, and tactile feedback. Such PV overlay shells would support the combination of sophisticated mannequins (e.g., from Laerdal Medical) or real humans with PV effects, without otherwise requiring modification of the patient simulator or uncomfortable body contortions of the human. There are many such approaches to realizing display and sensing overlay structures that are contemplated herein.

In a further example embodiment, herein the core elements of the disclosed Physical-Virtual Patient (PVP) system (device/apparatus, method, computer readable medium) can be realized in combination with actuated body components such as limbs (e.g., arms/hands or legs/feet), where the actuation is designed to simulate more realistic and challenging patient movement, both voluntary and involuntary, for scenarios such as gynecological exams or urinary catheter insertions. In a further example embodiment, the system can simulate the body being positioned in a lithotomy position for gynecological exams (e.g. the AR headset being attached to the speculum (be able to see the cervix)). This can be achieved using actively actuated joints (i.e. via motors/pneumatics or other such powered actuators) or passively actuated joints (i.e unpowered via coupling/transmission/using passive elements) (including hybrid combinations of both) whose responses can be tuned to follow complex position-force relationships (variable stiffness/impedance/admittance). The actuation could be applied to PV elements (e.g., a PV head), physical elements (e.g., rubber legs or arms), PV overlay shells, or hybrid combinations. There are many such approaches to adding actuation to the core elements that are contemplated herein.

In a further example embodiment, a Mobile Physical-Virtual Patient Systems is provided. Any of the previously described embodiments, configurations, or hybrid combinations of PV, physical, or real simulated patients could be mounted on a mobile platform, or equipped with actuated legs, to allow realistic movement (e.g., translation, rotation, or walking) around the scenario space. This would support, for example, the simulation of a patient who is pacing, or moving in an agitated manner. There are many such approaches to adding mobility to the core elements of the invention that are contemplated herein.

In addition, other embodiments of the PVBP system are configured for veterinary applications. Accordingly, the body components of the system are configured to resemble that of animals, such as dogs, cats, horses, cows, etc.

Figure 3:
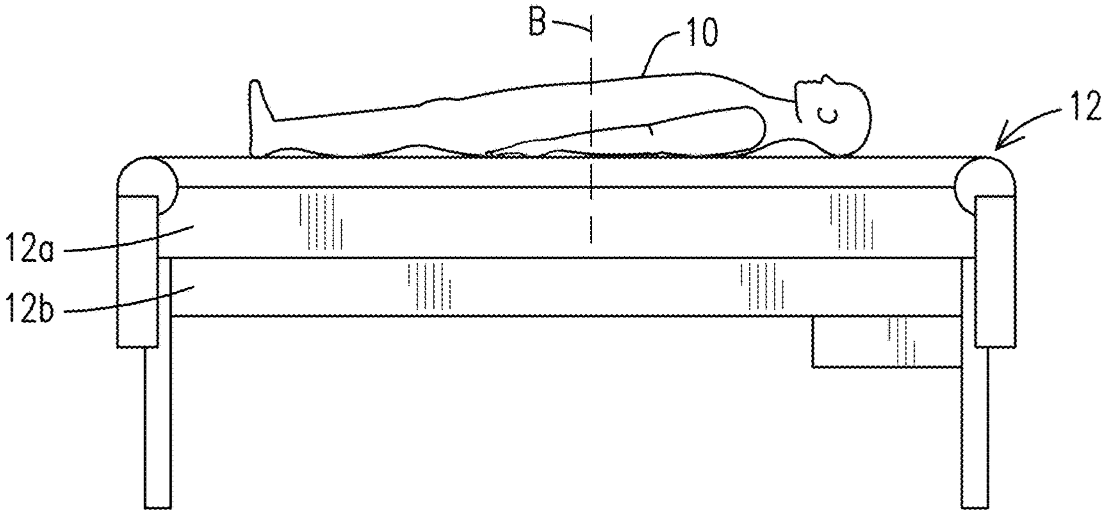
FIG. 3 is an illustration of a bed system of an embodiment of the invention.
Figure 15A:
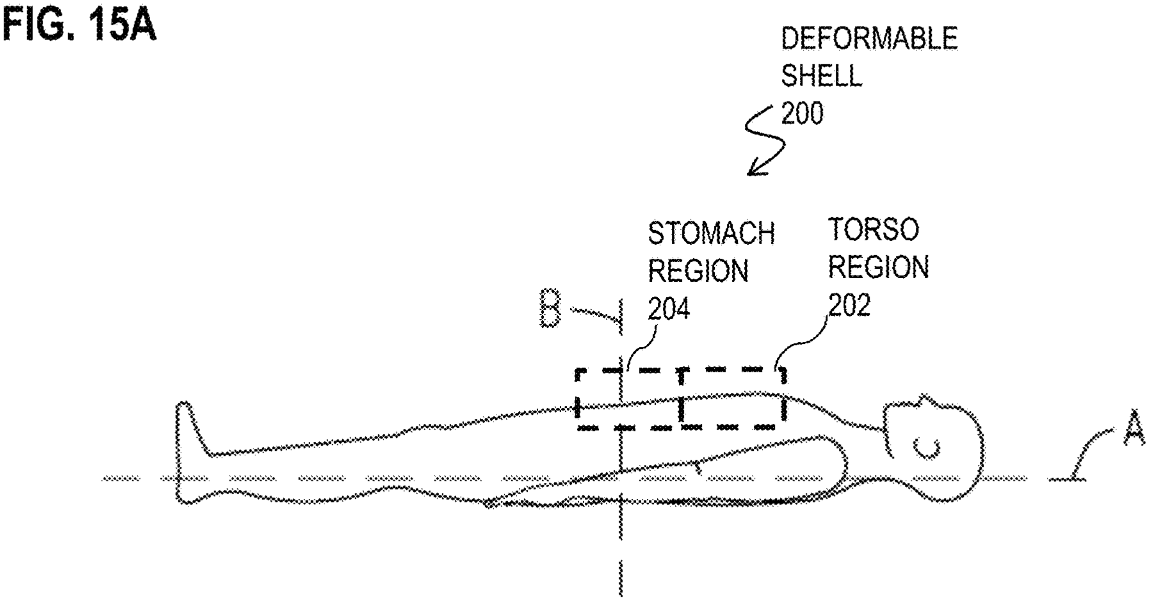
FIG. 15A is an image that illustrates an example of side view of a deformable shell, according to one embodiment.
Figure 15B:
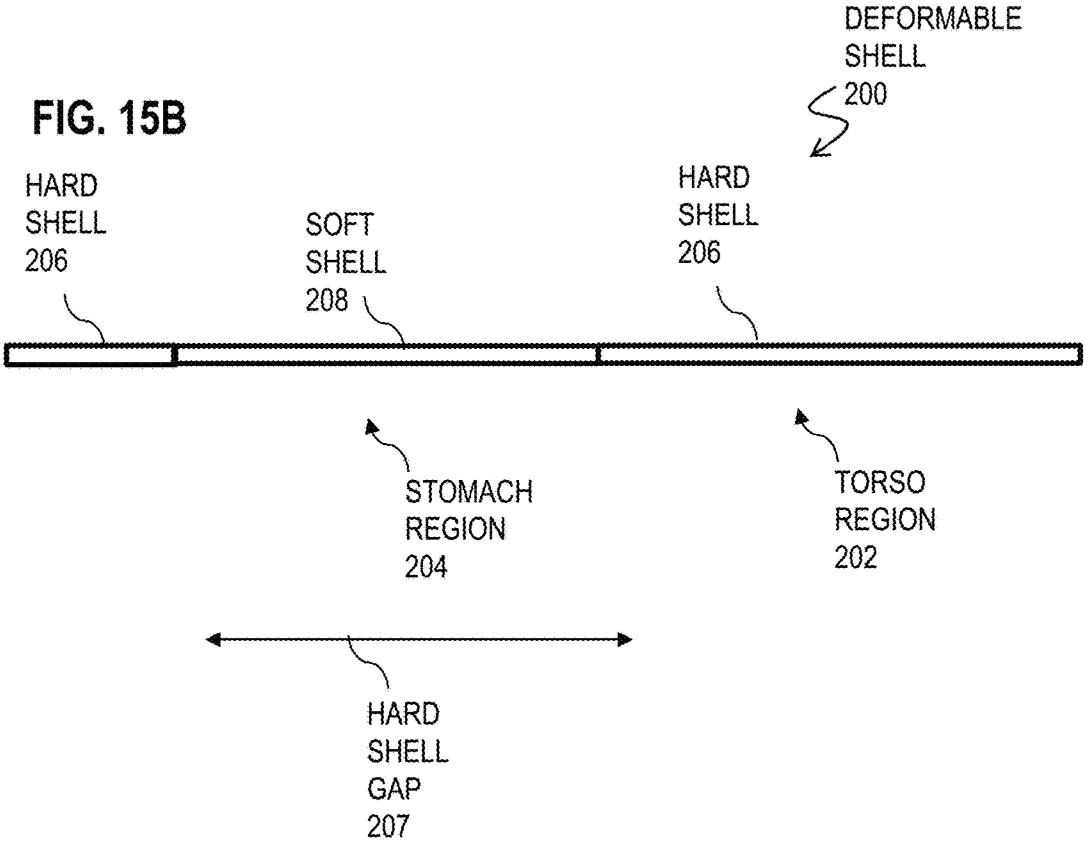
FIG. 15B is a cross-sectional view of the outer surface of the deformable shell of FIG. 15A across multiple regions of the patient body, according to one embodiment.

FIG. 15A is an image that illustrates an example of side view of a deformable shell 200 used in the bed system 5 of FIG. 3, according to one embodiment. FIG. 15B is a cross-sectional view of the outer surface of the deformable shell 200 of FIG. 15A across multiple regions 202, 204 of the patient body, according to one embodiment. In one embodiment, the shell 200 is deformable with a first region 202 having a first level of deformity over a first portion (e.g. torso) of the patient's body and a second region 204 having a second level of deformity over a second portion (e.g. stomach) of the patient's body. In an example embodiment, the first region 202 is a torso region of the shell 200 with a lower level of deformity (harder shell) than the second region 204 that is a stomach region of the shell 200 with a higher level of deformity (softer shell). In an example embodiment, FIG. 15B depicts in one embodiment that the first region 202 includes hard shell 206 material whereas the second region 204 includes soft shell 208 material (e.g. in a gap 207 in the hard shell 206 material of the deformable shell 200 and/or adjacent the second region 204). In other embodiments, the shell 200 is a deformable hybrid shell where the hard shell can have more than one gap (e.g. gap 207) allowing for a mix between hard and soft shells. In still other embodiments, the interactive devices in the lower assembly 12*b* include an air blower that directs air on the soft shell 208 material and/or through a gap to deform the soft shell 208 material and simulate a breathing torso. In some embodiments, gaps are provided in the hard shell 206. In other embodiments, the soft materials 208 could also be mixed with the hard shell 206 material in certain regions of the shell 200. In still other embodiments, some materials of the shell 20 are configured to turn from hard shell 206 material to soft shell 208 material, depending on factors (e.g. heat and/or low currents applied to the shell 200).

Figure 21A:
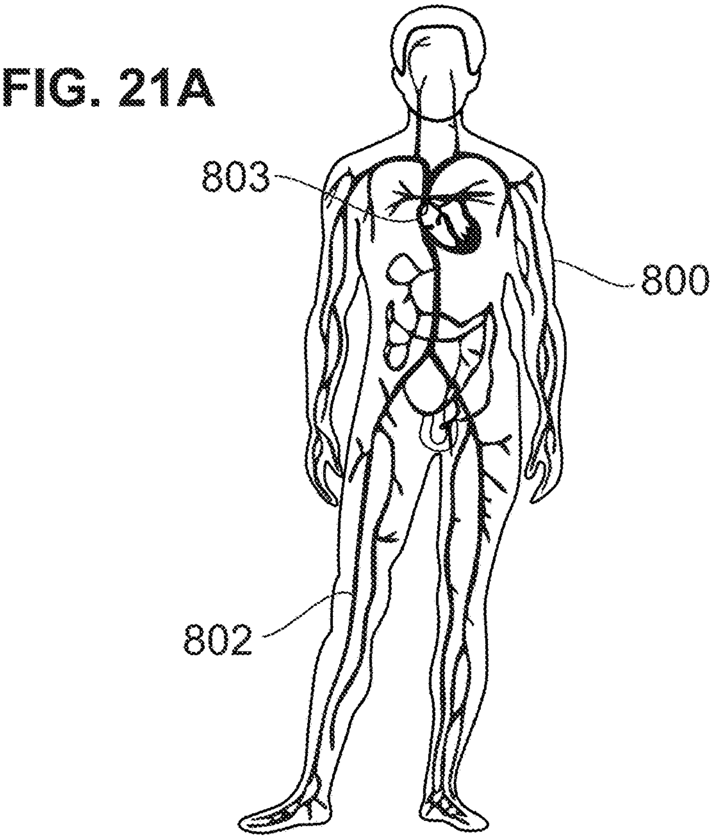
FIG. 21A is an image that illustrates an example of the shell of FIG. 2 with one or more dynamic images including a human venous system, according to an embodiment.
Figure 21B:
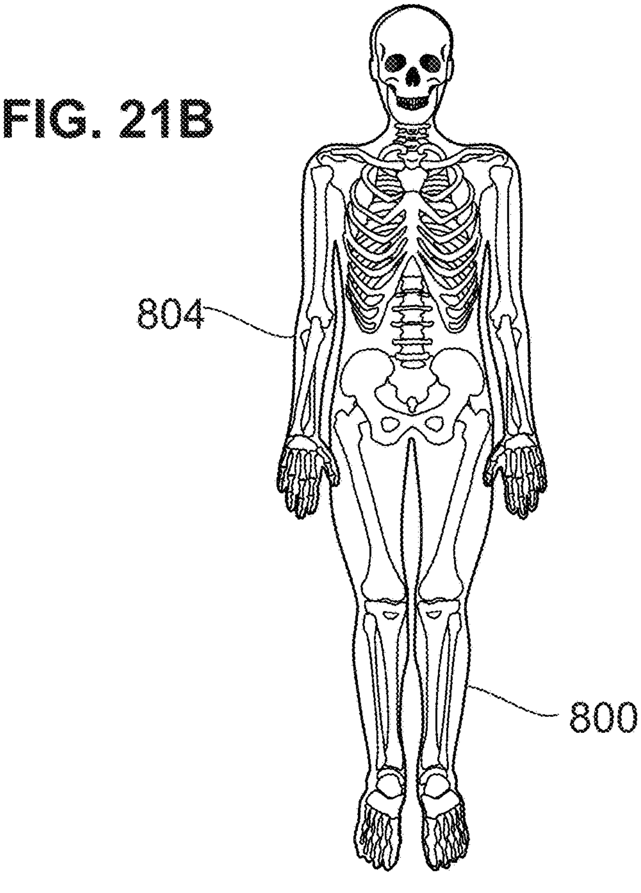
FIG. 21B is an image that illustrates an example of the shell of FIG. 2 with one or more dynamic images including a human skeletal system, according to an embodiment.

FIG. 21A is an image that illustrates an example of the shell 800 of FIG. 2 with one or more dynamic images including a human venous system 802, according to an embodiment. FIG. 21B is an image that illustrates an example of the shell 800 of FIG. 2 with one or more dynamic images including a human skeletal system 804, according to an embodiment. In an embodiment, the imaging devices 20 are configured to render the one or more dynamic images including the underlying venous system 802 and/or underlying organ 803 structures of the patient's body and/or one or more underlying bone structures (e.g. skeletal system 804) of the patient's body. In still other embodiments, one or more of color tone and/or ability to change and add different gradients could also be displayed with the dynamic images. Although FIGS. 21A-21B depict human venous system and/or human skeletal system, the embodiments of the invention are not limited to this particular embodiment and can depict non-human venous system, non-human skeletal systems, etc. In yet another embodiment, the computing unit 16 and imaging unit 20 are configured to project the underlying venous system and/or skeletal system based on one or more parameters (e.g. length, width, thickness, etc) of the shell 10 and thus, the projected venous system and/or skeletal system are sized based on the size of the shell 10.

Figure 24:
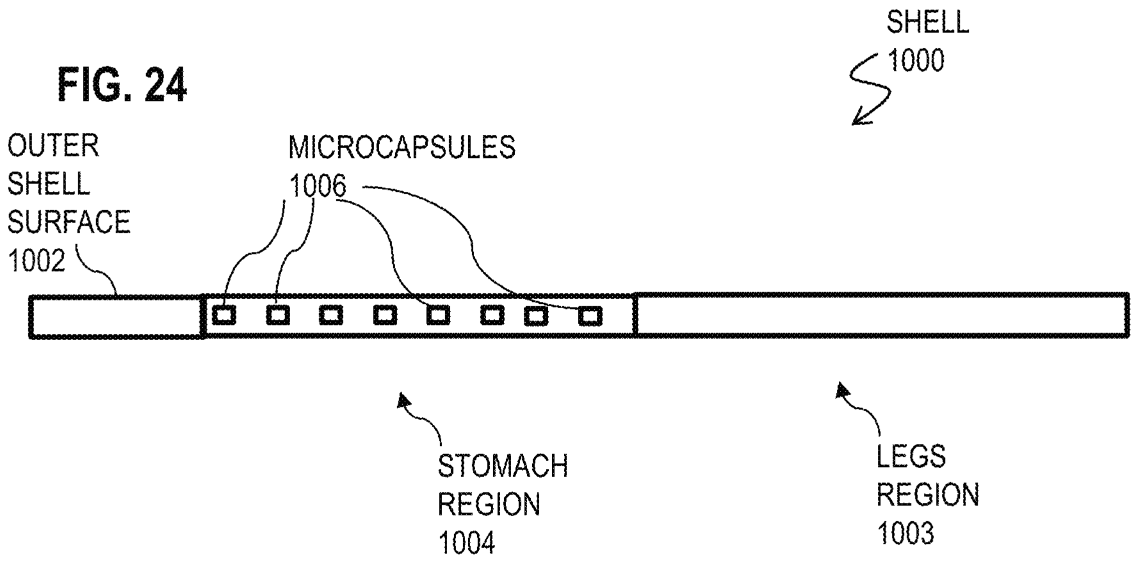
FIG. 24 is an image that illustrates an example of microcapsules within the outer surface of the shell of FIG. 2 to change a reflective property of the shell, according to an embodiment.

FIG. 24 is an image that illustrates an example of microcapsules 1006 within the outer surface 1002 of the shell 1000 of FIG. 2 to change a reflective property of the shell, according to an embodiment. In one embodiment, an example of the effect achieved by the microcapsules 1006 is disclosed in U.S. Pat. No. 10,321,107, which is incorporated by reference herein. In some embodiments, the microcapsules 1006 are embedded in the outer surface 1002 (or inner surface, see embodiments discussed below with respect to FIGS. 33-34) of the shell 1000. The microcapsules 1006 are configured to change a reflective property of the outer surface 1002 (or inner surface, see embodiments discussed below with respect to FIGS. 33-34). of the shell 1000 based on a signal received from the computing unit 16. In an example embodiment, the microcapsules 1006 operate similar to an E-ink system (e.g. Kindle®) and based on the signal received from the computing 16, vary the reflective property (e.g. brightness or color) of the outer surface 1002 to create one or more dynamic images. In one example embodiment, the microcapsules 1006 create the dynamic images with or without assistance of the imaging devices 20. In one embodiment, some of the dynamic images on the outer surface of the shell 1000 are provided by the microcapsules 1006 and other dynamic images on the outer surface of the shell 1000 are provided by the imaging devices 20. In an example embodiment, the described system depends on added light (using the projectors) but does not leverage the light that is already there in the environment. Consequently, in this embodiment, it may need a dark room which may cause the dynamic images to "glow" compared to the environment. In one embodiment, the microcapsules 1006 embedded in the surface changes the reflective properties of the surface without emitting any light. In an example embodiment, for the patient bed, the projectors could still act as a backlight if needed, but that the surface reflectance parameters would be controlled by the computer unit 16 and microcapsules 1006. This could be tuned to realistic reflectance properties of the surface to match the material properties of the simulated patient (e.g., skin, wounds, clothes). In yet another embodiment, this could extend to more than just RGB light reflectance but include sub-surface scattering, realistic 3D wound layers, visible blood capillaries underneath the outer skin layers, etc.

Figure 29:
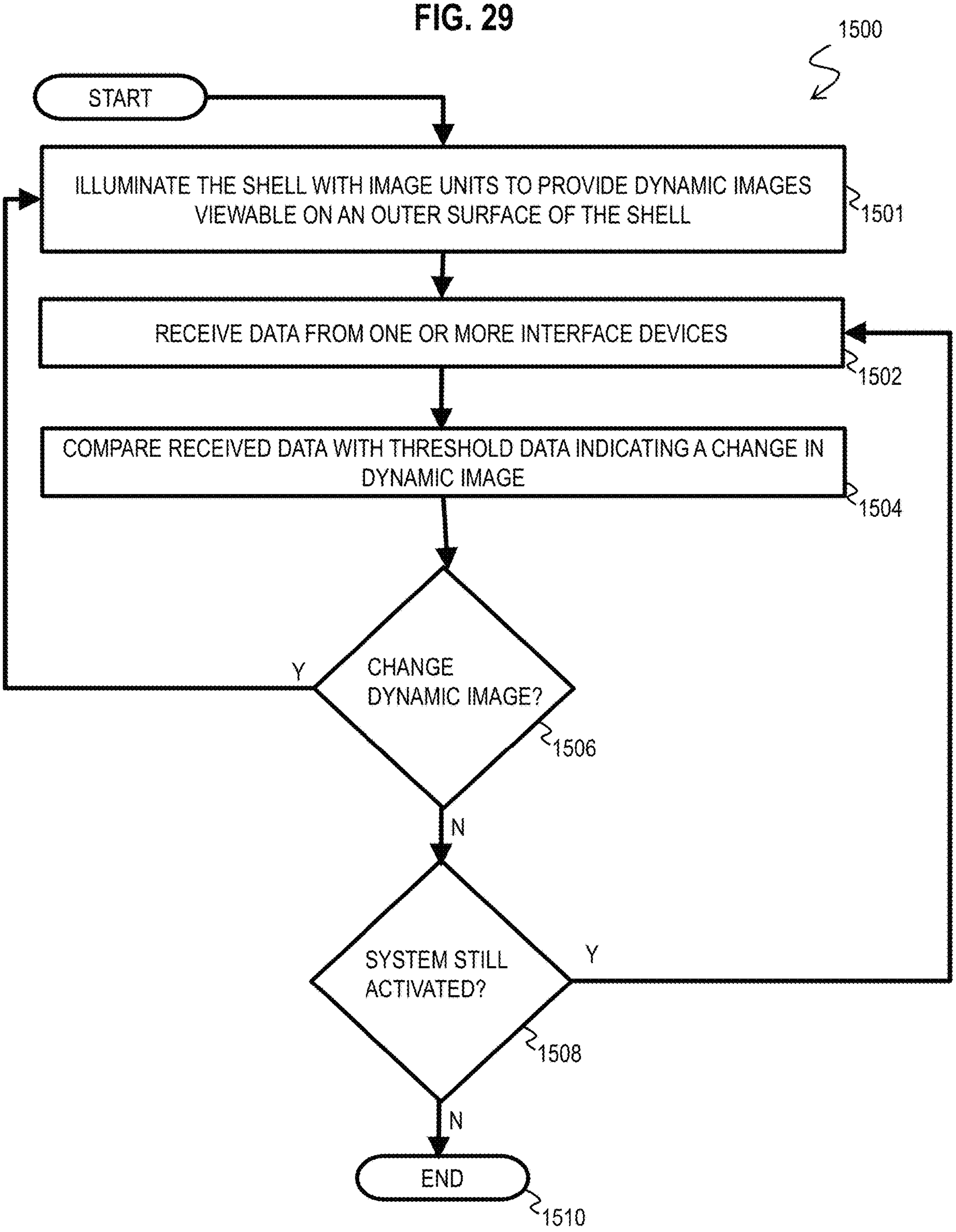
FIG. 29 is a flow diagram that illustrates an example of a method for displaying dynamic images on the shell of FIG. 1, according to an embodiment.

Although steps are depicted in FIG. 29, in other embodiments, one or more steps, or portions thereof, are performed in a different order, or overlapping in time, in series or in parallel, or are omitted, or one or more additional steps are added, or the method is changed in some combination of ways. In step 1501, the shell 10 is illuminated with the image units 20 to provide dynamic images viewable on the outer surface of the shell 10. In one embodiment, in step 1501 a user provides user input through one or more input devices to activate the interactive simulation for medical training (e.g. selecting a difficulty level, AI level of the patient, etc.). In another embodiment, in step 1501 the computing unit 16 transmits one or more signals to the imaging devices 20 based on the module 17, so that the imaging devices 20 transmit the dynamic images to the shell 10 and/or to the outer surface of the shell 10 (e.g. at different time increments). In an example embodiment, in step 1501 the computing unit 16 transmits the signal to the imaging devices 20 to transmit the dynamic image to the shell 10 based on any of the embodiments and/or examples discussed herein. In other embodiments, in step 1501 the computing unit 16 transmits one or more signals to output devices other than the imaging device 20 to provide output other than visual output (e.g. tactile display, aural/audio output devices, fluid reservoir 1206, etc.)

In step 1502, after the dynamic images are projected by the imaging devices 20 onto the shell 10 and/or outer surface of the shell 10, the interface devices (e.g. sensor devices 22, interactive devices 24) receive data. In one embodiment, in step 1502 the interface devices receive data based on input from a user (e.g. touching the shell or skin, hovering within a proximal distance of the shell or skin, contacting a part of the body with medical equipment such as the stethoscope on the stomach/chest or the pulse oximeter on the finger, etc.). In an example embodiment, after step 1502 a physiological model of the patient is checked against the received data in step 1502 (e.g. pulse rate is checked with a pulse rate from a physiological model, Sp02 measured level is checked with a level from a physiological model, etc.) and based on this step the dynamic image on the shell 10 is modified (e.g. if the temperature of the patient is above a normal temperature in the physiological mode, the dynamic image on the shell 10 is modified to indicate a fever by changing the color of the skin, etc.).

In step 1504, the computing unit 16 receives the data from the interactive devices in step 1502 and compares the received data with threshold data to indicate a change in the dynamic image and/or a change in movement of a physical part of the patient's body and/or a change in some parameter of the system. In one embodiment in step 1504, the computing unit 16 determines whether a detected pressure from a sensor device 22 exceeds a pressure threshold indicating a change in the dynamic image (e.g. move eyes of patient, open mouth of patient, etc). In another embodiment, in step 1504, the computing unit 16 determines whether medical equipment (e.g. stethoscope) has engaged a certain region (e.g. chest) of the patient body so to change a parameter of the system (e.g. transmit a signal to the audio source adjacent the chest so that the stethoscope can detect an audio sound from the audio source). In one embodiment in step 1504, the computing unit 16 determines whether a detected pressure from a sensor device 22 exceeds a pressure threshold indicating that a part of the patient's body should be moved (e.g. transmit a signal to a motor to move the right arm from a first position to a second position to manifest detection of the pressure). Other embodiments of step 1504 can be performed based on the teachings in other embodiments discussed herein. In an example embodiment, after step 1504 a behavioral model of the patient is checked against the received data in step 1504 (e.g. detected pressure from pressure sensor 22 is compared with the behavioral model that provides the pressure threshold that indicates a certain action of the patient such as opening of the eyes, opening of mouth, etc.) and based on this step the dynamic image on the shell 10 is modified (e.g. if the pressure is above the pressure threshold of the behavioral model, the dynamic image on the shell 10 is modified to open the mouth of the patient and/or open the eyes of the patient, etc.).

In step 1506, it is determined whether to change the dynamic image and/or the movement of a physical part of the patient's body and/or a parameter of the system, based on step 1504. If the determination in step 1506 is affirmative, the method 1500 proceeds back to step 1501 and the dynamic image is changed and/or the physical part of the patient body is moved and/or the parameter of the system is modified, as determined in step 1504. If the determination in step 1506 is negative, the method 1500 proceeds to step 1508 and it is determined whether the system is still activated. If this determination is affirmative then the method 1500 proceeds back to step 1502 and if the determination is negative the method 1500 ends at block 1510.

Figure 30:
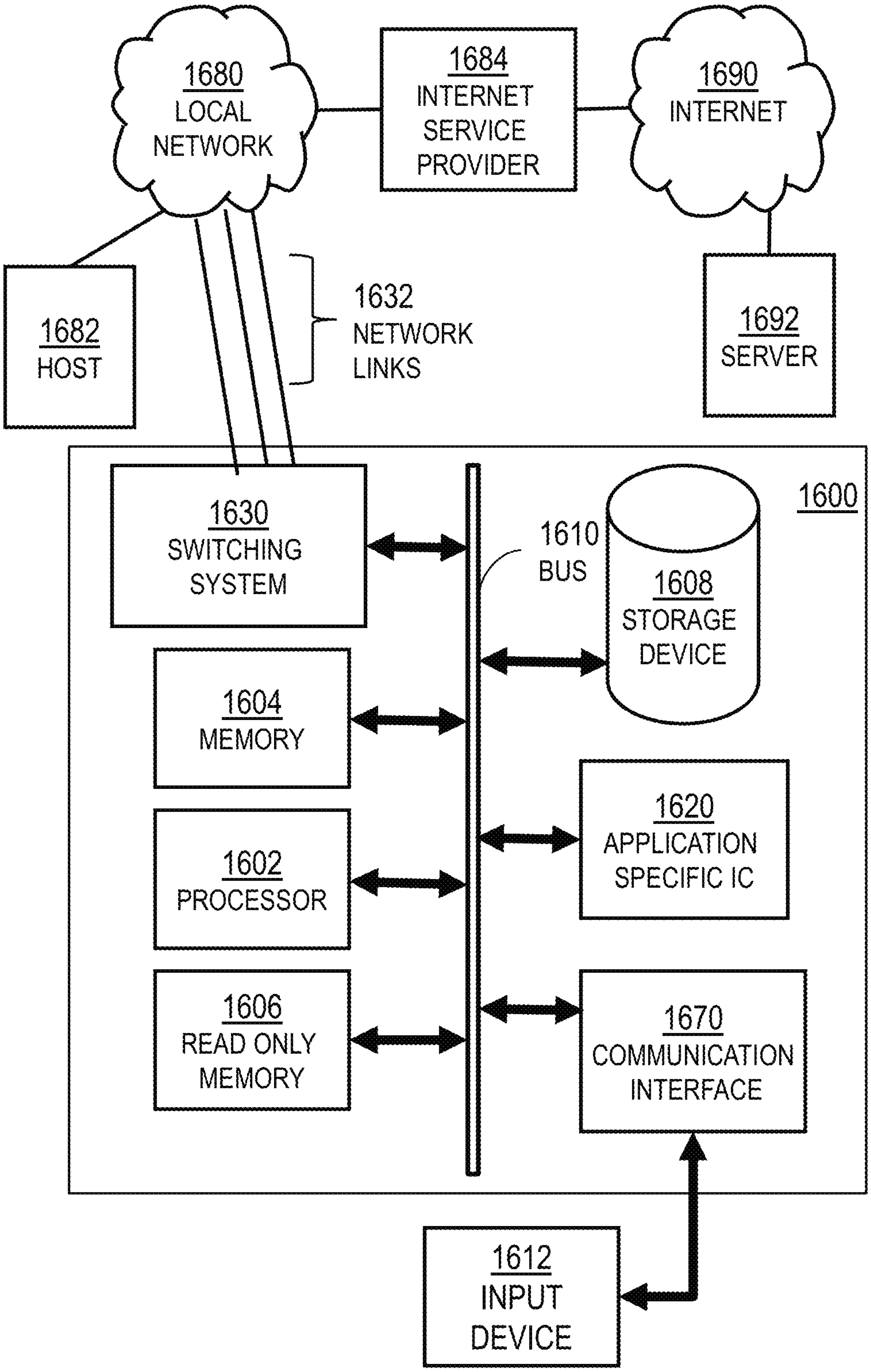
FIG. 30 is a block diagram that illustrates a computer system upon which an embodiment of the invention may be implemented.

FIG. 30 is a block diagram that illustrates a computer system 1600 upon which an embodiment of the invention may be implemented. Computer system 1600 includes a communication mechanism such as a bus 1610 for passing information between other internal and external components of the computer system 1600. Information is represented as physical signals of a measurable phenomenon, typically electric voltages, but including, in other embodiments, such phenomena as magnetic, electromagnetic, pressure, chemical, molecular atomic and quantum interactions. Computer system 1600, or a portion thereof, constitutes a means for performing one or more steps of one or more methods described herein.

A sequence of binary digits constitutes digital data that is used to represent a number or code for a character. A bus 1610 includes many parallel conductors of information so that information is transferred quickly among devices coupled to the bus 1610. One or more processors 1602 for processing information are coupled with the bus 1610. A processor 1602 performs a set of operations on information. The set of operations include bringing information in from the bus 1610 and placing information on the bus 1610. The set of operations also typically include comparing two or more units of information, shifting positions of units of information, and combining two or more units of information, such as by addition or multiplication. A sequence of operations to be executed by the processor 1602 constitutes computer instructions.

Computer system 1600 also includes a memory 1604 coupled to bus 1610. The memory 1604, such as a random access memory (RAM) or other dynamic storage device, stores information including computer instructions. Dynamic memory allows information stored therein to be changed by the computer system 1600. RAM allows a unit of information stored at a location called a memory address to be stored and retrieved independently of information at neighboring addresses. The memory 1604 is also used by the processor 1602 to store temporary values during execution of computer instructions. The computer system 1600 also includes a read only memory (ROM) 1606 or other static storage device coupled to the bus 1610 for storing static information, including instructions, that is not changed by the computer system 1600. Also coupled to bus 1610 is a non-volatile (persistent) storage device 1608, such as a magnetic disk or optical disk, for storing information, including instructions, that persists even when the computer system 1600 is turned off or otherwise loses power.

Information, including instructions, is provided to the bus 1610 for use by the processor from an external input device 1612, such as a keyboard containing alphanumeric keys operated by a human user, or a sensor. A sensor detects conditions in its vicinity and transforms those detections into signals compatible with the signals used to represent information in computer system 1600. Other external devices coupled to bus 1610, used primarily for interacting with humans, include a display device 1614, such as a cathode ray tube (CRT) or a liquid crystal display (LCD), for presenting images, and a pointing device 1616, such as a mouse or a trackball or cursor direction keys, for controlling a position of a small cursor image presented on the display 1614 and issuing commands associated with graphical elements presented on the display 1614.

In the illustrated embodiment, special purpose hardware, such as an application specific integrated circuit (IC) 1620, is coupled to bus 1610. The special purpose hardware is configured to perform operations not performed by processor 1602 quickly enough for special purposes. Examples of application specific ICs include graphics accelerator cards for generating images for display 1614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1600 also includes one or more instances of a communications interface 1670 coupled to bus 1610. Communication interface 1670 provides a two-way communication coupling to a variety of external devices that operate with their own processors, such as printers, scanners and external disks. In general, the coupling is with a network link 1678 that is connected to a local network 1680 to which a variety of external devices with their own processors are connected. For example, communication interface 1670 may be a parallel port or a serial port or a universal serial bus (USB) port on a personal computer. In some embodiments, communications interface 1670 is an integrated service digital network (ISDN) card or a digital subscriber line (DSL) card or a telephone modem that provides an information communication connection to a corresponding type of telephone line. In some embodiments, a communication interface 1670 is a cable modem that converts signals on bus 1610 into signals for a communication connection over a coaxial cable or into optical signals for a communication connection over a fiber optic cable. As another example, communications interface 1670 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1670 sends and receives electrical, acoustic or electromagnetic signals, including infrared and optical signals, that carry information streams, such as digital data.

The term computer-readable medium is used herein to refer to any medium that participates in providing information to processor 1602, including instructions for execution. Such a medium may take many forms, including, but not limited to, non-volatile media, volatile media and transmission media. Non-volatile media include, for example, optical or magnetic disks, such as storage device 1608. Volatile media include, for example, dynamic memory 1604. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1602, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1602, except for carrier waves and other signals.

Logic encoded in one or more tangible media includes one or both of processor instructions on a computer-readable storage media and special purpose hardware, such as ASIC *1620.

Network link 1678 typically provides information communication (e.g. wired or wireless using different protocols, such as WI-FI®, BLUETOOTH®, BLER, IoT®, 5G®, etc.) through one or more networks to other devices that use or process the information. For example, network link 1678 may provide a connection through local network 1680 to a host computer 1682 or to equipment 1684 operated by an Internet Service Provider (ISP). ISP equipment 1684 in turn provides data communication services through the public, world-wide packet-switching communication network of networks now commonly referred to as the Internet 1690. A computer called a server 1692 connected to the Internet provides a service in response to information received over the Internet. For example, server 1692 provides information representing video data for presentation at display 1614.

The invention is related to the use of computer system 1600 for implementing the techniques described herein. According to one embodiment of the invention, those techniques are performed by computer system 1600 in response to processor 1602 executing one or more sequences of one or more instructions contained in memory 1604. Such instructions, also called software and program code, may be read into memory 1604 from another computer-readable medium such as storage device 1608. Execution of the sequences of instructions contained in memory 1604 causes processor 1602 to perform the method steps described herein. In alternative embodiments, hardware, such as application specific integrated circuit 1620, may be used in place of or in combination with software to implement the invention. Thus, embodiments of the invention are not limited to any specific combination of hardware and software.

The signals transmitted over network link 1678 and other networks through communications interface 1670, carry information to and from computer system 1600. Computer system 1600 can send and receive information, including program code, through the networks 1680, 1690 among others, through network link 1678 and communications interface 1670. In an example using the Internet 1690, a server 1692 transmits program code for a particular application, requested by a message sent from computer 1600, through Internet 1690, ISP equipment 1684, local network 1680 and communications interface 1670. The received code may be executed by processor 1602 as it is received, or may be stored in storage device 1608 or other non-volatile storage for later execution, or both. In this manner, computer system 1600 may obtain application program code in the form of a signal on a carrier wave.

Various forms of computer readable media may be involved in carrying one or more sequence of instructions or data or both to processor 1602 for execution. For example, instructions and data may initially be carried on a magnetic disk of a remote computer such as host 1682. The remote computer loads the instructions and data into its dynamic memory and sends the instructions and data over a telephone line using a modem. A modem local to the computer system 1600 receives the instructions and data on a telephone line and uses an infra-red transmitter to convert the instructions and data to a signal on an infra-red a carrier wave serving as the network link 1678. An infrared detector serving as communications interface 1670 receives the instructions and data carried in the infrared signal and places information representing the instructions and data onto bus 1610. Bus 1610 carries the information to memory 1604 from which processor 1602 retrieves and executes the instructions using some of the data sent with the instructions. The instructions and data received in memory 1604 may optionally be stored on storage device 1608, either before or after execution by the processor 1602.

Figure 31:
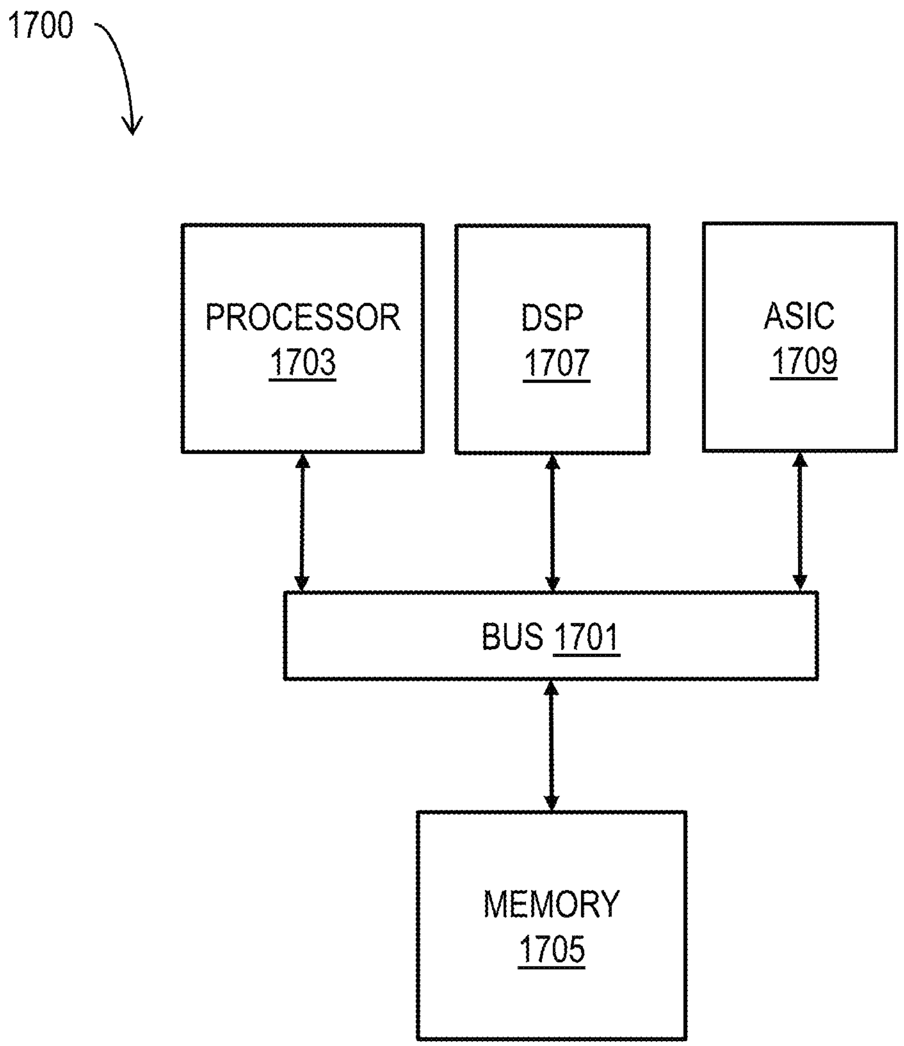
FIG. 31 is a block diagram that illustrates a chip set upon which an embodiment of the invention may be implemented.

FIG. 31 illustrates a chip set 1700 upon which an embodiment of the invention may be implemented. Chip set 1700 is programmed to perform one or more steps of a method described herein and includes, for instance, the processor and memory components described with respect to FIG. 16 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1700, or a portion thereof, constitutes a means for performing one or more steps of a method described herein.

In one embodiment, the chip set 1700 includes a communication mechanism such as a bus 1701 for passing information among the components of the chip set 1700. A processor 1703 has connectivity to the bus 1701 to execute instructions and process information stored in, for example, a memory 1705. The processor 1703 may include one or more processing cores with each core configured to perform independently. A multi-core processor enables multiprocessing within a single physical package. Examples of a multi-core processor include two, four, eight, or greater numbers of processing cores. Alternatively or in addition, the processor 1703 may include one or more microprocessors configured in tandem via the bus 1701 to enable independent execution of instructions, pipelining, and multithreading. The processor 1703 may also be accompanied with one or more specialized components to perform certain processing functions and tasks such as one or more digital signal processors (DSP) 1707, or one or more application-specific integrated circuits (ASIC) 1709. A DSP 1707 typically is configured to process real-world signals (e.g., sound) in real time independently of the processor 1703. Similarly, an ASIC 1709 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1703 and accompanying components have connectivity to the memory 1705 via the bus 1701. The memory 1705 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1705 also stores the data associated with or generated by the execution of one or more steps of the methods described herein.

Figure 32:
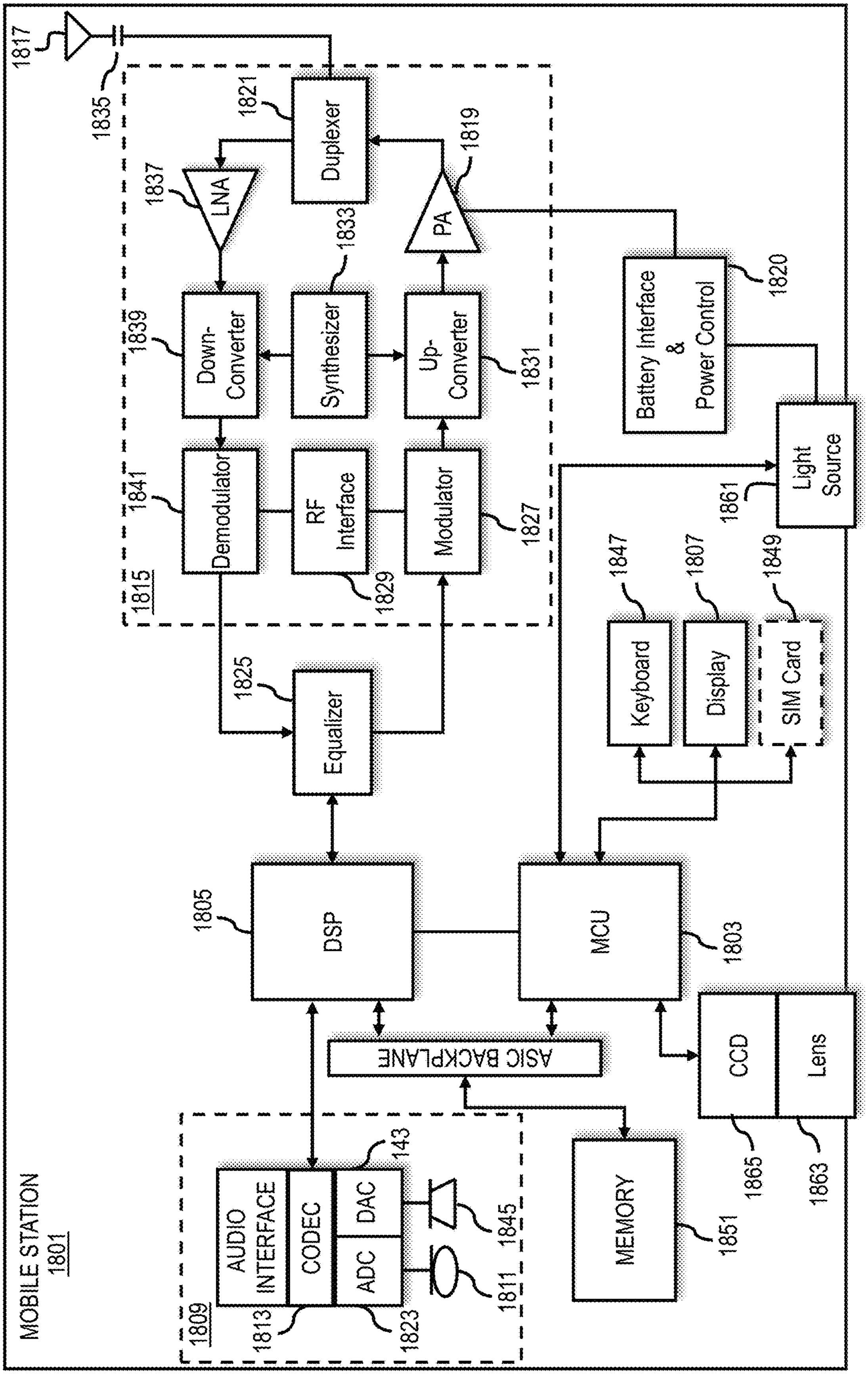
FIG. 32 is a block diagram that illustrates a mobile device upon which an embodiment of the invention may be implemented.

FIG. 32 is a diagram of exemplary components of a mobile device 1800 (e.g., cell phone handset) for communications, which is capable of operating in the system of FIG. 2C, according to one embodiment. In some embodiments, mobile device 1801, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1803, a Digital Signal Processor (DSP) 1805, and a receiver/transmitter unit including a microphone gain control unit and a speaker gain control unit. A main display unit 1807 provides a display to the user in support of various applications and mobile device functions that perform or support the steps as described herein. The display 1807 includes display circuitry configured to display at least a portion of a user interface of the mobile device (e.g., mobile telephone). Additionally, the display 1807 and display circuitry are configured to facilitate user control of at least some functions of the mobile device. An audio function circuitry 1809 includes a microphone 1811 and microphone amplifier that amplifies the speech signal output from the microphone 1811. The amplified speech signal output from the microphone 1811 is fed to a coder/decoder (CODEC) 1813.

A radio section 1815 amplifies power and converts frequency in order to communicate with a base station, which is included in a mobile communication system, via antenna 1817. The power amplifier (PA) 1819 and the transmitter/modulation circuitry are operationally responsive to the MCU 1803, with an output from the PA 1819 coupled to the duplexer 1821 or circulator or antenna switch, as known in the art. The PA 1819 also couples to a battery interface and power control unit 1820.

In use, a user of mobile device 1801 speaks into the microphone 1811 and his or her voice along with any detected background noise is converted into an analog voltage. The analog voltage is then converted into a digital signal through the Analog to Digital Converter (ADC) 1823. The control unit 1803 routes the digital signal into the DSP 1805 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1825 for compensation of any frequency-dependent impairments that occur during transmission though the air such as phase and amplitude distortion. After equalizing the bit stream, the modulator 1827 combines the signal with a RF signal generated in the RF interface 1829. The modulator 1827 generates a sine wave by way of frequency or phase modulation. In order to prepare the signal for transmission, an up-converter 1831 combines the sine wave output from the modulator 1827 with another sine wave generated by a synthesizer 1833 to achieve the desired frequency of transmission. The signal is then sent through a PA 1819 to increase the signal to an appropriate power level. In practical systems, the PA 1819 acts as a variable gain amplifier whose gain is controlled by the DSP 1805 from information received from a network base station. The signal is then filtered within the duplexer 1821 and optionally sent to an antenna coupler 1835 to match impedances to provide maximum power transfer. Finally, the signal is transmitted via antenna 1817 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile device 1801 are received via antenna 1817 and immediately amplified by a low noise amplifier (LNA) 1837. A down-converter 1839 lowers the carrier frequency while the demodulator 1841 strips away the RF leaving only a digital bit stream. The signal then goes through the equalizer 1825 and is processed by the DSP 1805. A Digital to Analog Converter (DAC) 1843 converts the signal and the resulting output is transmitted to the user through the speaker 1845, all under control of a Main Control Unit (MCU) 1803 which can be implemented as a Central Processing Unit (CPU) (not shown).

The MCU 1803 receives various signals including input signals from the keyboard 1847. The keyboard 1847 and/or the MCU 1803 in combination with other user input components (e.g., the microphone 1811) comprise a user interface circuitry for managing user input. The MCU 1803 runs a user interface software to facilitate user control of at least some functions of the mobile device 1801 as described herein. The MCU 1803 also delivers a display command and a switch command to the display 1807 and to the speech output switching controller, respectively. Further, the MCU 1803 exchanges information with the DSP 1805 and can access an optionally incorporated SIM card 1849 and a memory 1851. In addition, the MCU 1803 executes various control functions required of the mobile device. The DSP 1805 may, depending upon the implementation, perform any of a variety of conventional digital processing functions on the voice signals. Additionally, DSP 1805 determines the background noise level of the local environment from the signals detected by microphone 1811 and sets the gain of microphone 1811 to a level selected to compensate for the natural tendency of the user of the mobile device 1801.

The CODEC 1813 includes the ADC 1823 and DAC 1843. The memory 1851 stores various data including call incoming tone data and is capable of storing other data including music data received via, e.g., the global Internet. The software module could reside in RAM memory, flash memory, registers, or any other form of writable storage medium known in the art. The memory device 1851 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1849 carries, for instance, important information, such as the cellular phone number, the carrier supplying service, subscription details, and security information. The SIM card 1849 serves primarily to identify the mobile device 1801 on a radio network. The card 1849 also contains a memory for storing a personal telephone number registry, text messages, and user specific mobile device settings.

In some embodiments, the mobile device 1801 includes a digital camera comprising an array of optical detectors, such as charge coupled device (CCD) array 1865. The output of the array is image data that is transferred to the MCU for further processing or storage in the memory 1851 or both. In the illustrated embodiment, the light impinges on the optical array through a lens 1863, such as a pin-hole lens or a material lens made of an optical grade glass or plastic material. In the illustrated embodiment, the mobile device 1801 includes a light source 1861, such as a LED to illuminate a subject for capture by the optical array, e.g., CCD 1865. The light source is powered by the battery interface and power control module 1820 and controlled by the MCU 1803 based on instructions stored or loaded into the MCU 1803.

It should be understood that the examples and embodiments described herein are for illustrative purposes only and that various modifications or changes in light thereof will be suggested to persons skilled in the art and are to be included within the spirit and purview of this application.

REFERENCES

[1] Bourke, Paul, "Spherical Mirror: A New Approach to Hemispherical Dome Projection", *Planetarian* December 2005 p. 6-9.

[2] Bourke, Paul, "Spherical Mirror: A New Approach to Hemispherical Dome Projection", Proceedings of the 3rd International Conference on Computer Graphics and Interactive Techniques in Australasia and Southeast Asia 2005, Dunedin, New Zealand, Nov. 29-Dec. 2, 2005.

[3] https://inspace.pro/fisheye-vs-spherical-mirror-projection-for-portable-domes

[4] C. Cruz-Neira, D. J. Sandin, T. A. DeFanti, R. V. Kenyon, and J. C. Hart. The CAVE: audio visual experience automatic virtual environment. Commun. ACM, 35 (6): 64-72, June 1992

[5] V. Nalwa. A true omnidirectional viewer. Technical report, Bell Laboratories, Holmdel, NJ 07733, February 1996

[6] J. Underkoffler. A View From the Luminous Room. Personal Technologies, 1 (2): 49-59, June 1997.

What is claimed is:

1. A patient simulation system for medical training, comprising:

a shell comprising a physical anatomical model of at least a portion of a patient's body, the shell adapted to be illuminated to provide one or more dynamic images viewable on the outer surface of the shell;

an image system comprising one or more omnidirectional image devices adapted to render the one or more dynamic images viewable on the shell;

one or more interface devices located about the patient system to receive input and/or provide output; and one or more computing units in communication with the image units and interface devices, the computing units adapted to provide an interactive simulation for medical training.

2. The patient simulated system of claim 1, wherein the one or more omnidirectional image devices are enclosed by the shell.

3. The patient simulated system of claim 1, wherein the image devices include an omnidirectional projector.

4. The patient simulated system of claim 1, wherein the interface devices include an omnidirectional camera.

5. The patient simulated system of claim 1, wherein the image units include an omnidirectional projector and an omnidirectional mirror.

6. The patient simulated system of claim 5, wherein the image devices include a pair of omnidirectional projectors and an omnidirectional mirror, wherein the pair of omnidirectional projectors are mounted on opposite sides of the omnidirectional mirror.

7. The patient simulated system of claim 1, wherein the one or more omnidirectional image devices are positioned outside the shell.

8. The patient simulated system of claim 2, wherein a first omnidirectional mirror is positioned in a first region of the shell;

wherein a first omnidirectional projector is positioned within the shell and is oriented to direct light at the first omnidirectional mirror so that the incident light reflected off the first omnidirectional mirror renders one or more dynamic images on the first region of the shell.

9. The patient simulated system of claim 8, wherein a second omnidirectional mirror is positioned in a second region of the shell different from the first region;

and wherein a second omnidirectional projector is positioned within the shell and is oriented to direct light at the second omnidirectional mirror so that incident light reflected off the second omnidirectional mirror renders one or more dynamic images on the second region of the shell.

10. The patient simulated system of claim 9, wherein the first region of the shell is one of a head region, a torso region, an abdomen region, a thigh region, a leg region and a foot region of the shell and wherein the second region is one of the head region, the torso region, the abdomen region, the thigh region, the leg region and the foot region of the shell that is different from the first region.

11. The patient simulated system of claim 5, wherein the image devices include a first pair of omnidirectional projectors in an upper region of the shell and a second pair of omnidirectional projectors in a lower region of the shell, wherein each pair of omnidirectional projectors include a first projector and a second projector that are configured to direct light in opposite directions.

12. The patient simulated system of claim 11, wherein the image devices include a first pair of omnidirectional mirrors that are spaced apart in the upper region so that the first pair of omnidirectional projectors are positioned between the first pair of omnidirectional projectors;

and wherein the image devices include a second pair of omnidirectional mirrors that are spaced apart in the lower region so that the second pair of omnidirectional projectors are positioned between the second pair of omnidirectional projectors.

13. The patient simulated system of claim 7, wherein the one or more omnidirectional image devices include an omnidirectional projector and an omnidirectional mirror, wherein the omnidirectional projector is configured to output incident light that is reflected off the omnidirectional mirror into a cone of reflected light to project the one or more dynamic images onto the shell.

14. The patient simulated system of claim 2, wherein the one or more omnidirectional image devices comprise an omnidirectional projector and an omnidirectional mirror, wherein the omnidirectional projector is configured to generate an optical signal that is reflected or refracted by the omnidirectional mirror to an inner surface of the shell to project the one or more dynamic images onto the inner surface of the shell that are viewable on an outer surface of the shell.

15. The patient simulated system of claim 14, wherein the omnidirectional mirror is configured to reflect the optical signal in multiple directions so that a collective reflected light from the omnidirectional mirror projects the one or more dynamic images onto a first region or a second region of the inner surface of the shell.

16. The patient simulated system of claim 2, wherein the one or more omnidirectional image devices are configured to project a first dynamic image of the one or more dynamic images on an inner surface of the shell in a first region of the shell and is further configured to project a second dynamic image of the one or more dynamic images on the inner surface of the shell in a second region of the shell.

17. The patient simulated system of claim 16, wherein the one or more omnidirectional image devices include a first omnidirectional device enclosed by the first region of the shell that is configured to project the first dynamic image on the inner surface in the first region of the shell so that the first dynamic image is viewable from the outer surface of the shell and a second omnidirectional device enclosed by the second region of the shell that is configured to project the second dynamic image on the inner surface in the second region of the shell so that the second dynamic image is viewable from the outer surface of the shell.

18. The patient simulated system of claim 2, wherein the one or more omnidirectional image devices is configured to project the one or more dynamic images onto an inner surface of the shell and where the omnidirectional image device is the one or more interface device that is configured to receive the input based on detection of a presence of nearby objects to the shell based on detection of a reflection of incident light from the nearby object.

19. The patient simulated system of claim 1, wherein the one or more omnidirectional image devices are adapted to render the one or more dynamic images on an inner surface of the shell such that the one or more dynamic images are viewable on an outer surface of the shell.

20. A patient simulation system for medical training, comprising:

a shell comprising a physical anatomical model of at least a portion of a patient's body, the shell adapted to be illuminated to provide one or more images viewable on the outer surface of the shell;

an image system comprising one or more omnidirectional image devices adapted to render the one or more dynamic images viewable on the shell; and one or more computing units in communication with the image units, the computing units adapted to provide an interactive simulation for medical training;

wherein the one or more omnidirectional image devices are adapted to render the one or more dynamic images on an inner surface of the shell such that the one or more dynamic images are viewable on an outer surface of the shell.

* * * * *